US008293772B2

(12) United States Patent
Ottosen

(10) Patent No.: US 8,293,772 B2
(45) Date of Patent: Oct. 23, 2012

(54) TRIAZOLE SUBSTITUTED AMINOBENZOPHENONE COMPOUNDS

(75) Inventor: Erik Rytter Ottosen, Ølstykke (DK)

(73) Assignee: Leo Pharma A/S, Ballerup (DK)

( * ) Notice: Subject to any disclaimer, the term of this patent is extended or adjusted under 35 U.S.C. 154(b) by 0 days.

(21) Appl. No.: 11/292,064

(22) Filed: Dec. 2, 2005

(65) Prior Publication Data
US 2006/0128766 A1 Jun. 15, 2006

Related U.S. Application Data

(60) Provisional application No. 60/635,000, filed on Dec. 13, 2004.

(51) Int. Cl.
A61K 31/4192 (2006.01)
C07D 249/04 (2006.01)
C07D 403/02 (2006.01)

(52) U.S. Cl. ..................... 514/359; 548/255

(58) Field of Classification Search .......... None
See application file for complete search history.

(56) References Cited

U.S. PATENT DOCUMENTS
2006/0166990 A1* 7/2006 Ottosen et al. ............ 514/237.5

FOREIGN PATENT DOCUMENTS

| WO | WO 98/32730 A | 7/1998 |
| WO | WO-01/05744 A | 1/2001 |
| WO | WO-01/05745 A | 1/2001 |
| WO | WO-01/05746 A | 1/2001 |
| WO | WO-01/05749 A | 1/2001 |
| WO | WO-01/05751 A | 1/2001 |
| WO | WO-01/42189 A | 6/2001 |
| WO | WO-01/90074 A2 | 11/2001 |
| WO | WO-02/076447 A1 | 10/2002 |
| WO | WO-02/083622 A | 10/2002 |
| WO | WO-03/018535 A | 3/2003 |
| WO | WO-2004/056762 A2 | 7/2004 |
| WO | WO-2005/009940 A1 | 2/2005 |

OTHER PUBLICATIONS

Barnes, P.J.; "Mediators of Chronic Obstructive Pulmonary Disease", Pharmacol. Rev. (2004), vol. 56, p. 515-548.*
Kay, A.B.; "Allergy and Allergic Diseases, First of Two Parts", N. Engl. J. Med. (2001), vol. 344, p. 30-37.*
Singh et al. "Differential Expression of Inflammatory Cytokines and Chemokines Genes by Homocystein in the Human Retinal Pigmented Epithelial Cells", The FASEB Journal (2006), vol. 20, p. A719, (abstract only.).*
McCulloch et al. "Signalling Platforms that Modulate the Inflammatory Response: New Targets for Drug Development", Nature Reviews Drug Discovery (2006), vol. 5, p. 864-876.*
Shacter et al., "Chronic Inflammation and Cancer", Oncology (2002), vol. 16, p. 217-232.*
Sabat et al., "The development of novel c-2, c-8 and n-9 trisubstituted purines a inhibitors of TNF-a production", Bioorg. Med Chem. Lett, 16, 2006, 4360-4365.*
Chawla et al., "Challenges in Polymorphism of Pharmaceuticals", CRIPS vol. 5, No. 1, Jan.-Mar. 2004 (4 Pages).*
Newman et al., "Solid-state analysis of the active pharmaceutical ingredient in drug products", DDT vol. 8, No. 19, Oct. 2003, p. 898-905.*

Madhusudan et al., Clinical Biochemistry, 2004, 37, 618-635.*
Fischer et al., Cancer Treatment Reviews 2007, 33, 391-406.*
Miss Madhury D. Bhavsar et al., "Synthesis of Diarylamine Derivatives", Man-Made Textiles, Jun. 1987, No. 30, vol. 6, p. 275-276.
Miss Madhury D. Bhavsar et al., Synthesis of Diarylamine Derivatives and 9-Arylacridines, ManMade Textile in India, May 1986, No. 29, vol. 5, p. 224-230.
Miss Madhury D. Bhavsar et al., "Synthesis of Diarylamine Derivatives", Man Made Textiles In India, Nov. 1985, No. 28, vol. 11, p. 425-431.
Barnes, "Cytokine-directed therapies in asthma," Allergology International, vol. 52, 2003, pp. 53-63.
Fleisher et al., "Synergistic Uveitic Effects of Tumor Necrosis Factor-a and Interleukin-1B," Investigative Ophthalmology & Visual Science, vol. 33, No. 7, Jun. 1992, pp. 2120-2127.
Junghans et al., "Epidermal Cytokines IL-1B, TNF-a, and IL-12 in Patients with Atopic Dermatitis: Response to Application of House Dust Mite Antigens," The Society for Investigative Dermatology, The Journal of Investigative Dermatology, vol. 111, No. 6, Dec. 1998, pp. 1184-1188.
Oh et al., "The Potential Angiogenic Role of Macrophages in the Formation of Choroidal Neovascular Membranes," Investigative Ophthalmology & Visual Science, Aug. 1999, vol. 40, No. 9, pp. 1891-1898.
Revesz et al., "SAR of benzoylpyridines and benzophenones as p38a MAP kinase inhibitors with oral activity," Bioorganic & Medicinal Chemistry Letters, vol. 14, Jul. 5, 2004, XP-002362314, pp. 3601-3605.
Weinstein et al, "Therapy of Moderate-to-Severe Psoriasis," Immunobiologicals as Pathogenic Probes, ISBN: 0-8247-4116-1, 2003, pp. 246-259.

* cited by examiner

Primary Examiner — Sun Jae Loewe
(74) Attorney, Agent, or Firm — Birch, Stewart, Kolasch & Birch, LLP

(57) ABSTRACT

The invention relates to novel compounds according to formula Ia and Ib,

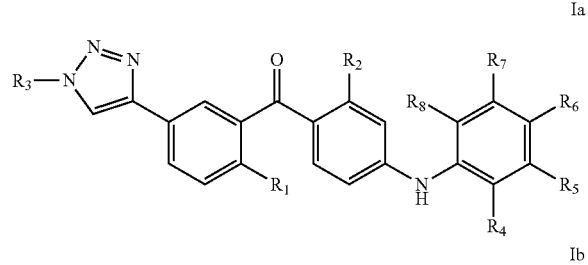

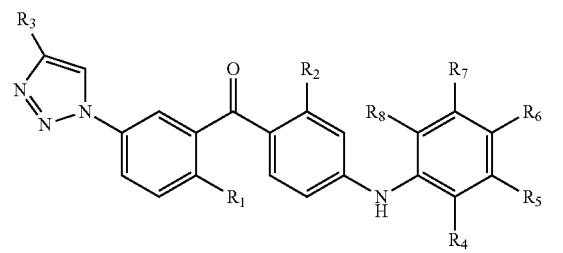

said compounds being useful, e.g. in the treatment of inflammatory, ophthalmic diseases, or cancer.

18 Claims, No Drawings

TRIAZOLE SUBSTITUTED AMINOBENZOPHENONE COMPOUNDS

This Nonprovisional application claims priority under 35 U.S.C. §119(e) on U.S. Provisional Application No(s). 60/635,000 filed on Dec. 13, 2004, the entire contents of which are hereby incorporated by reference.

FIELD OF THE INVENTION

The present invention relates to a novel type of triazole substituted aminobenzophenones and to their use in therapy.

BACKGROUND OF THE INVENTION

Aminobenzophenones are known from the scientific as well as the patent literature. For example, WO 98/32730, WO 01/05746, WO 01/05749, WO 01/05751, WO 01/05744 and WO 01/05745 all disclose compounds with the common core structure

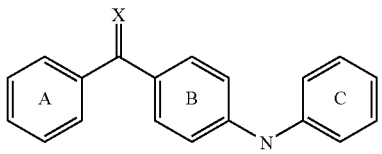

wherein the phenyl ring C is substituted by amine derivatives. Moreover, WO 01/42189 and WO 02/076447 disclose compounds with a similar structure, but with no nitrogen substituent in phenyl ring C. Finally, WO 01/90074 and WO 02/083622 disclose compounds where the phenyl rings A and C respectively are replaced by heterocycles. The compounds disclosed in these patent application are indicated to be inhibitors of interleukin 1β (IL-1β) and tumour necrosis factor α (TNF-α) secretion in vitro, which makes the compounds potentially useful in the treatment of inflammatory diseases where the production of cytokines is involved in the pathogenesis. Allegedly, aminobenzophenones exert their effect by inhibiting the p38 MAP kinase, which in turn inhibits the production of IL-1β and TNF-α.

The preparation of structurally related aminobenzophenones useful as dyes for textiles is disclosed in Man-Made Text. India (1987), 30(6), 275-6, Man-Made Text. India (1986), 29(5), 224-30, and Man-Made Text. India (1985), 28(11), 425, 427-9, 431.

SUMMARY OF THE INVENTION

It has surprisingly been found that novel triazole substituted aminobenzophenone derivatives are potent inhibitors of interleukin 1β (IL-1β) and tumour necrosis factor α (TNF-α) secretion in vitro and in vivo, suggesting their utility in the treatment and/or prevention of inflammatory diseases and other conditions where the secretion and modulation of proinflammatory cytokines is involved in the pathogenesis. It has been found that triazole substituted aminobenzophenone derivatives of the present invention exert their anti-inflammatory effect by inhibiting or downregulating MAP kinases, more specifically the p38 MAP kinase, a stress-activated protein which is an important element of the signal transduction pathway leading to the production of proinflammatory cytokines.

The triazole substituted aminobenzophenone derivatives of the present invention may furthermore be useful in the treatment of cancer or ophthalmic diseases or conditions.

Accordingly, the present invention relates to a compound of general formula Ia or Ib

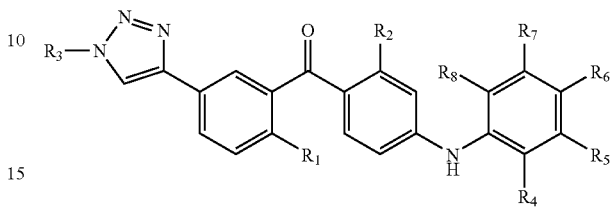

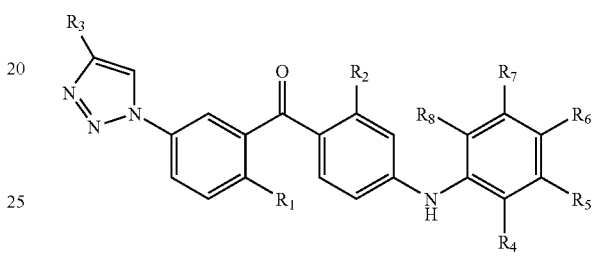

wherein
$R_1$ is methyl, chloro, bromo, or methoxy;
$R_2$ is chloro or methyl;
$R_3$ represents $C_{1-6}$alkyl, $C_{2-6}$alkenyl, $C_{2-6}$alkynyl, $C_{1-6}$hydroxyalkyl, $C_{1-6}$haloalkyl, $C_{1-6}$alkoxy, $C_{1-6}$alkoxycarbonyl, $C_{1-6}$amino, ureido, thioureido, $C_{1-6}$alkylcarbonyloxy, $C_{1-6}$alkylcarbonyl, $C_{1-6}$alkoxycarbonyloxy, $C_{1-6}$alkoxysulfonyloxy, $C_{1-6}$alkoxycarbamoyl, or $C_{1-6}$aminocarbonyl,
each of which is optionally substituted with one or more, same or different substituents selected from the group consisting of halogen, hydroxy, mercapto, trifluoromethyl, cyano, carboxy, $CONH_2$, nitro, oxo, $—S(O)_2NH_2$, $C_{1-4}$alkyl, $C_{2-4}$alkenyl, $C_{2-4}$alkynyl, $C_{1-4}$hydroxyalkyl, $C_{1-6}$haloalkyl, $C_{1-4}$alkoxy, $C_{1-4}$alkoxycarbonyl, ureido, thioureido, $C_{1-4}$alkylcarbonyloxy, $C_{1-4}$alkoxycarbonyloxy, $C_{1-4}$alkoxysulfonyloxy, $C_{1-4}$alkoxycarbamoyl, $C_{1-4}$aminocarbonyl, $C_{1-4}$alkylthio, $C_{3-6}$cycloalkyl, $C_{3-6}$cycloalkenyl, amino, imino, $C_{1-4}$aminosulfonyl, $C_{1-4}$aminocarbonyloxy, $C_{1-4}$alkylsulfonylamino, $C_{1-4}$alkoxyimino, $C_{1-4}$alkylcarbonylamino, $C_{1-4}$alkylsulfonyl, $C_{1-6}$heteroaryl, $C_{1-6}$heterocycloalkyl, or $C_{2-6}$heterocycloalkenyl,
wherein said $C_{1-4}$alkyl, $C_{2-4}$alkenyl, $C_{2-4}$alkynyl, $C_{1-4}$hydroxyalkyl, $C_{1-6}$haloalkyl, $C_{1-4}$alkoxy, $C_{1-4}$alkoxycarbonyl, ureido, thioureido, $C_{1-4}$alkylcarbonyloxy, $C_{1-4}$alkoxycarbonyloxy, $C_{1-4}$alkoxysulfonyloxy, $C_{1-4}$alkoxycarbamoyl, $C_{1-4}$aminocarbonyl, $C_{1-4}$alkylthio, $C_{3-6}$cycloalkyl, $C_{3-6}$cycloalkenyl, amino, imino, $C_{1-4}$aminosulfonyl, $C_{1-4}$aminocarbonyloxy, $C_{1-4}$alkylsulfonylamino, $C_{1-4}$alkoxyimino, $C_{1-4}$alkylcarbonylamino, $C_{1-4}$alkylsulfonyl, $C_{1-6}$heteroaryl, $C_{1-6}$heterocycloalkyl, or $C_{2-6}$heterocycloalkenyl, are optionally further substituted with one or more, same or different substituents selected from the group consisting of halogen, hydroxy, $—NH_2$, mercapto, trifluoromethyl, cyano, carboxy, $CONH_2$, nitro, oxo, $—S(O)_2NH_2$, $C_{1-4}$alkyl, or $C_{1-4}$hydroxyalkyl,
or $R_3$ represents hydrogen, hydroxy, or carboxy;
$R_4$, $R_5$, $R_6$, $R_7$, and $R_8$ independently of each other represent hydrogen, halogen, $—NH_2$, hydroxy, trifluoromethyl, methoxy, ethoxy, cyano, acetyl, acetamido, methyl, or ethyl;

provided that the compound is not [4-(2-aminophenyl) amino)-2-chlorophenyl]-[2-methyl-5-[1-[2-[(tetrahydro-2H-pyran-2-yl)oxy]ethyl]-1H-1,2,3-triazol-4-yl]-phenyl]-methanone or [4-[(2-aminophenyl)amino]-2-chlorophenyl]-[5-[1-(2-hydroxyethyl)-1H-1,2,3-triazol-4-yl]-2-methylphenyl]-methanone;
or a pharmaceutically acceptable salt, solvate, or ester thereof.

In another aspect, the invention relates to a pharmaceutical composition comprising a compound of formula Ia or Ib or a pharmaceutically acceptable salt, solvate, or ester thereof together with a pharmaceutically acceptable excipient or vehicle.

In a further aspect, the invention relates to a method of preventing, treating or ameliorating inflammatory diseases or conditions, or ophthalmic diseases or conditions, the method comprising administering to a patient in need thereof an effective amount of a compound of formula Ia or Ib.

In a further aspect, the invention relates to a method of treating or ameliorating cancer, the method comprising administering to a patient in need thereof an effective amount of a compound of formula Ia or Ib.

In a still further aspect, the invention relates to the use of a compound of formula Ia or Ib for the manufacture of a medicament for the prophylaxis, treatment or amelioration of inflammatory diseases or conditions, or ophthalmic diseases or conditions.

In a still further aspect, the invention relates to the use of a compound of formula Ia or Ib for the manufacture of a medicament for the treatment or amelioration of cancer.

DETAILED DESCRIPTION OF THE INVENTION

Definitions

In the present context, the term "alkyl" is intended to indicate the radical obtained when one hydrogen atom is removed from a hydrocarbon. Said alkyl comprises 1-6, preferably 1-4, such as 2-3, carbon atoms. The term includes the subclasses normal alkyl (n-alkyl), secondary and tertiary alkyl, such as methyl, ethyl, n-propyl, isopropyl, n-butyl, isobutyl, sec.-butyl, tert.-butyl, pentyl, isopentyl, hexyl and isohexyl.

The term "cycloalkyl" is intended to indicate a saturated cycloalkane radical, comprising 3-6 carbon atoms, such as 4-5 carbon atoms, e.g. cyclopropyl, cyclobutyl, cyclopentyl, and cyclohexyl.

The term "cycloalkenyl" is intended to indicate mono-, or di-unsaturated non-aromatic cyclic hydrocarbonsradicals, comprising 3-6 carbon atoms, such as 4-5 carbon atoms, e.g. cyclopropenyl, cyclobutenyl, cyclopentenyl, or cyclohexenyl.

The term "heteroaryl" is intended to include radicals of heterocyclic aromatic rings, comprising 1-4 heteroatoms (selected from O, S and N) and 1-6 carbon atoms, such as 1-3 heteroatoms and 1-6 carbon atoms, such as 1-2 heteroatoms and 1-5 carbon atoms, such as 1-2 heteroatoms and 2-4 carbon atoms, in particular 5- or 6-membered rings with 1-4 heteroatoms or 1-2 heteroatoms selected from O, S and N, e.g. pyridyl, tetrazolyl, thiazolyl, imidazolyl, pyrazolyl, oxazolyl, oxadiazolyl, thiophenyl, 1,2,4-triazolyl, isoxazolyl, pyrrolidinyl, thienyl, pyrazinyl, pyrimidinyl, [1,2,3]triazolyl, or isothiazolyl.

The term "heterocycloalkyl" is intended to indicate a cycloalkyl radical as defined above, in particular 5- or 6-membered rings, including polycyclic radicals, comprising 1-4 heteroatoms, preferably 1-3 heteroatoms, selected from O, N, or S, e.g. tetrahydropyranyl, morpholine, imidazolidinyl, dioxolanyl or piperidinyl.

The term "heterocycloalkenyl" is intended to indicate a cycloalkenyl radical as defined above, including polycyclic radicals, comprising 1-4 heteroatoms, preferably 1-3 heteroatoms, selected from O, N, or S, e.g. 1,6-dihydropyridinyl, 4,5-dihydro-1H-[1,2,4]-triazolyl, 4,5-dihydro-oxazolyl, 1-H-pyrazolyl, or 4,5-dihydro-isoxazolyl.

The term "alkenyl" is intended to indicate a mono-, di-, or triunsaturated hydrocarbon radical comprising 2-6 carbon atoms, in particular 2-4 carbon atoms, such as 2-3 carbon atoms, e.g. ethenyl, allyl, propenyl, butenyl, pentenyl, or hexenyl.

The term "alkynyl" is intended to indicate an hydrocarbon radical comprising 1-5 C-C triple bonds, e.g. 2 or 3 triple bonds, and 2-6 carbon atoms, the alkane chain typically comprising 2-5 carbon atoms, in particular 2-4 carbon atoms, such as 2-3 carbon atoms, e.g. ethynyl, propynyl, butynyl, pentynyl, or hexynyl.

The term "halogen" is intended to indicate a substituent form the $7^{th}$ main group of the periodic table, preferably fluoro, chloro and bromo.

The term "hydroxyalkyl" is intended to indicate an alkyl radical as defined above, wherein one or more hydrogen atoms are replaced by hydroxy.

The term "haloalkyl" is intended to indicate an alkyl radical as defined above, wherein one or more hydrogen atoms are replaced by halogen, same or different, such as bromo, iodo, chloro and/or fluoro.

The term "amino" is intended to indicate a radical of the formula —$NR_2$, wherein each R independently represents hydrogen, alkyl, alkenyl, or cycloalkyl, as indicate above, e.g. —$NH_2$, methylamino, diethylamino, cyclohexylamino, tert-butylamino, or ethylamino.

The term "imino" is intended to indicate a radical of the formula =N—R, wherein R represents hydrogen or alkyl as indicated above.

The term "alkoxy" is intended to indicate a radical of the formula —OR, wherein R is alkyl or alkenyl as indicated above, e.g. methoxy, ethoxy, n-propoxy, isopropoxy, butoxy, etc.

The term "alkylthio" is intended to indicate a radical of the formula —S—R, wherein R is alkyl as indicated above.

The term "alkoxycarbonyl" is intended to indicate a radical of the formula —C(O)—O—R, wherein R is alkyl as indicated above, e.g. methoxycarbonyl, ethoxycarbonyl, n-propoxycarbonyl, isopropoxycarbonyl, etc.

The term "alkylcarbonyloxy" is intended to indicate a radical of the formula —O—C(O)—R, wherein R is alkyl as indicated above, e.g. methylcarbonyloxy, or ethylcarbonyloxy.

The term "alkoxycarbonyloxy" is intended to indicate a radical of the formula —O—C(O)—O—R, wherein R is alkyl as indicated above.

The term "alkylcarbonyl" is intended to indicate a radical of the formula "—C(O)—R, wherein R is alkyl as indicated above, e.g. acetyl.

The term "ureido" is intended to indicate a radical of the formula "—NR'—C(O)—NH—R, wherein R' is hydrogen or alkyl as indicated above, and R is hydrogen, alkyl, alkenyl, alkynyl, or cycloalkyl as indicated above, e.g. —NH—C(O)—$NH_2$, methylureido, ethylureido, tert-butylureido, cyclohexylureido, methylthioureido, isopropylureido, or n-propylureido.

The term "thioureido" is intended to indicate a radical of the formula "—NR'—C(S)—NH—R, wherein R' is hydrogen or alkyl as indicated above, and R is hydrogen, alkyl, or cycloalkyl as indicated above, e.g. —NH—C(S)—$NH_2$.

The term "alkoxysulfonyloxy" is intended to represent a radical of the formula —O—S(O)$_2$—O—R, wherein R is alkyl as indicated above.

The term "aminosulfonyl" is intended to indicate a radical of the formula —S(O)$_2$—NR$_2$, wherein each R independently represents hydrogen, or alkyl as indicated above.

The term "aminocarbonyloxy" is intended to indicate a radical of the formula —NR'—C(O)—O—R, wherein R' is hydrogen or alkyl as indicated above, and R is alkyl as indicated above, e.g. aminocarbonyl-tert-butoxy.

The term "alkylsulfonylamino" is intended to indicate a radical of the formula —NR'—S(O)$_2$—R, wherein R is alkyl as indicated above, and R' is hydrogen or alkyl as indicated above, e.g. methylsulfonylamino.

The term "alkoxyimino" intended to indicate a radical of the formula =N—O—R, wherein R is hydrogen or alkyl as indicated above, e.g. methoxyimino.

The term "alkoxycarbamoyl" intended to indicate a radical of the formula —C(O)NR'—O—R, wherein R' is hydrogen or alkyl as indicated above, and R is alkyl as indicated above.

The term "aminocarbonyl" is intended to indicate a radical of the formula —C(O)—NR'$_2$, wherein each R' is independently hydrogen, alkyl, or alkenyl as indicated above, e.g. carbamoyl, methylaminocarbonyl, ethylaminocarbonyl, propylaminocarbonyl, or butylaminocarbonyl.

The term "alkylcarbonylamino" is intended to indicate a radical of the formula —NR'—C(O)—R, wherein R' is hydrogen or alkyl as indicated above, and R is alkyl as indicated above, e.g. acetylamino.

The term "pharmaceutically acceptable salt" is intended to indicate salts prepared by reacting a compound of formula I with a suitable inorganic or organic acid, such as hydrochloric, hydrobromic, hydroiodic, sulfuric, nitric, phosphoric, formic, acetic, 2,2-dichloroaetic, adipic, ascorbic, L-aspartic, L-glutamic, galactaric, lactic, maleic, L-malic, phthalic, citric, propionic, benzoic, glutaric, gluconic, D-glucuronic, methanesulfonic, salicylic, succinic, malonic, tartaric, benzenesulfonic, ethane-1,2-disulfonic, 2-hydroxy ethanesulfonic acid, toluenesulfonic, sulfamic or fumaric acid. Pharmaceutically acceptable salts of compounds of formula I may also be prepared by reaction with a suitable base such as sodium hydroxide, potassium hydroxide, magnesium hydroxide, calcium hydroxide, ammonia, or suitable non-toxic amines, such as lower alkylamines, for example triethylamine, hydroxy-lower alkylamines, for example 2-hydroxyethylamine, bis-(2-hydroxyethyl)-amine, cycloalkylamines, for example dicyclohexylamine, or benzylamines, for example N,N'-dibenzylethylenediamine, and dibenzylamine, or L-arginine or L-lysine.

The term "solvate" is intended to indicate a species formed by interaction between a compound, e.g. a compound of formula I, and a solvent, e.g. alcohol, glycerol or water, wherein said species are in a solid form. When water is the solvent, said species is referred to as a hydrate.

The term "pharmaceutically acceptable ester" is intended to indicate easily hydrolysable esters such as alkanoyloxyalkyl, aralkanoyloxyalkyl, aroyloxyalkyl, e.g. acetoxymethyl, pivaloyloxymethyl, benzoyloxymethyl esters and the corresponding 1'-oxyethyl derivatives, or alkoxycarbonyloxyalkyl esters, e.g. methoxycarbonyloxymethyl esters and ethoxycarbonyloxymethyl esters and the corresponding 1'-oxyethyl derivatives, or lactonyl esters, e.g. phthalidyl esters, or dialkylaminoalkyl esters, e.g. dimethylaminoethyl esters. Easily hydrolysable esters include in vivo hydrolysable esters of the compounds of formula I. Such esters may be prepared by conventional methods known to persons skilled in the art, such as method disclosed in GB patent No. 1 490 852 incorporated herein by reference.

The term compound I, or a compound of formula I includes both compound Ia and Ib.

"p38 MAP kinase" is a stress-activated protein kinase existing in several isoforms (p38α, p38β, p38β2, p38γ and p38δ). The p38 MAP kinase is activated by different stimuli including heat, chemical, osmotic, pH and oxidative stress, growth factor withdrawal, high or low glucose and ultraviolet radiation. p38 is also stimulated by agents that mediate the initial physiological response to injury, infection and inflammation, such as LPS and pro-inflammatory cytokines IL-1β, TNF-α, FasL, CD40L and TGF-β. Like other MAP kinases, p38 is phosphorylated by kinases, including MKK3, MEK6 and MKK6, on a threonine and tyrosine in an activation loop (Thr-Xaa-Tyr) close to the ATP and substrate binding site. In turn, p38 phosphorylates and activates the serine-threonine protein kinases MAPKAP kinase-2, MAPKAP kinase-3, MAPKAP kinase-5, MNK-1 and MSK-1. It has been established that activation of p38 regulates cytokine biosynthesis in many cell types either directly by phosphorylating and activating transcription factors involved in the expression of cytokines or indirectly, e.g. by phosphorylating MSK-1 which, when activated, activates the transcription factor CREB. It has also been shown that certain pyridinyl imidazoles, e.g. SB203580, which inhibit p38, inhibit the production of IL-1β and TNF-α from LPS-treated human monocytes. It has therefore been concluded that p38 constitutes a potentially highly interesting target for the development of anti-inflammatory compounds (cf. J C Lee et al., *Immunopharmacology* 47, 2000, pp. 185-201 and references reviewed therein; P R Young, "Specific Inhibitors of p38 MAP kinase" in *Signaling Networks and Cell Cycle Control: The Molecular Basis of Cancer and Other Diseases*, J S Gutkind (Ed.), Humana Press, Inc., Totowa, N.J., and references reviewed therein).

There are several reports on p38 MAP kinase and inflammatory cytokines in relation to cell growth and apoptosis, such as tumor proliferation and metastasis. Though the exact mechanism of p38 MAP kinase mediated cell growth regulation is not known, it is believed that p38MAP kinase constitutes a potentially highly interesting target for the development of anti cancer drugs (S Nakada et al., Anticancer Research 21(1A), 2001, pp. 167-171 and references cited therein; C Denkert et al., Cancer Letters 195(1), 2003 p.p. 101-109 and references cited therein).

Compounds of formula Ia or Ib may comprise asymmetrically substituted (chiral) carbon atoms and carbon-carbon double bonds which may give rise to the existence of isomeric forms, e.g. enantiomers, diastereomers and geometric isomers. The present invention relates to all such isomers, either in pure form or as mixtures thereof. Pure stereoisomeric forms of the compounds and the intermediates of this invention may be obtained by the application of procedures known in the art. Diastereomers may be separated by physical separation methods such as selective crystallization and chromatographic techniques, e.g. liquid chromatography using chiral stationary phases. Enantiomers may be separated from each other by the selective crystallization of their diastereomeric salts with optically active acids. Alternatively, enantiomers may be separated by chromatographic techniques using chiral stationary phases. Said pure stereoisomeric forms may also be derived from the corresponding pure stereoisomeric forms of the appropriate starting materials, provided that the reaction occurs stereoselectively or stereospecifically. Preferably, if a specific stereoisomer is desired, said compound will be synthesized by stereoselective or stereospecific methods of preparation. These methods will advantageously employ chiral pure starting materials. Likewise, pure geometric isomers may be obtained from the corresponding pure geometric isomers of the appropriate starting materials. A mixture of geometric isomers will typically exhibit different physical properties, and they may thus be separated by standard chromatographic techniques well-known in the art.

A triazole moiety can be considered as an isoster of an amide, but without being susceptible towards hydrolytic cleavage by amidase-like enzymes. Compounds of formula Ia or Ib are therefore believed to be more metabolically stable than their corresponding amide derivatives.

Preferred Embodiments of the Compound of Formula Ia and Ib

In a presently preferred embodiment of the compounds of formula Ia or Ib, $R_3$ represents $C_{1-6}$alkyl, $C_{2-6}$alkenyl, $C_{2-6}$alkynyl, $C_{1-6}$hydroxyalkyl, $C_{1-6}$alkoxycarbonyl, $C_{1-6}$alkylcarbonyl, ureido, or $C_{1-6}$aminocarbonyl, each of which are optionally substituted with one or more, same or different substituents selected from the group consisting of halogen, hydroxy, mercapto, trifluoromethyl, cyano, carboxy, $CONH_2$, nitro, oxo, —$S(O)_2NH_2$, $C_{1-4}$alkyl, $C_{2-4}$alkenyl, $C_{2-4}$alkynyl, $C_{1-4}$hydroxyalkyl, $C_{1-4}$alkoxy, $C_{1-4}$alkoxycarbonyl, ureido, thioureido, $C_{1-4}$alkylcarbonyloxy, $C_{1-4}$alkoxycarbonyloxy, $C_{1-4}$alkoxysulfonyloxy, $C_{1-4}$alkoxycarbamoyl, $C_{1-4}$aminocarbonyl, $C_{1-4}$alkylthio, $C_{3-6}$cycloalkyl, $C_{3-6}$cycloalkenyl, amino, imino, $C_{1-4}$aminosulfonyl, $C_{1-4}$aminocarbonyloxy, $C_{1-4}$alkylsulfonylamino, $C_{1-4}$alkoxyimino, $C_{1-4}$alkylcarbonylamino, $C_{1-4}$alkylsulfonyl, $C_{1-6}$heteroaryl, $C_{1-6}$heterocycloalkyl, or $C_{2-6}$heterocycloalkenyl, the last 27 of which are optionally further substituted with one or more, same or different substituents selected from the group consisting of halogen, hydroxy, —$NH_2$, mercapto, trifluoromethyl, cyano, carboxy, $CONH_2$, nitro, oxo, —$S(O)_2NH_2$, $C_{1-4}$alkyl, or $C_{1-4}$hydroxyalkyl, or $R_3$ represents hydrogen, hydroxy, or carboxy;

provided that the compound is not

[4-(2-Amino-phenylamino)-2-chloro-phenyl]-(2-methyl-5-{1-[2-(tetrahydro-pyran-2-yloxy)-ethyl]-1H-[1,2,3]triazol-4-yl}-phenyl)-methanone, or

[4-(2-Amino-phenylamino)-2-chloro-phenyl]-{5-[1-(2-hydroxy-ethyl)-1H-[1,2,3]triazol-4-yl]-2-methyl-phenyl}-methanone.

In a further presently preferred embodiment of the compounds of formula Ia or Ib, $R_4$, $R_5$, $R_6$, $R_7$, and $R_8$ independently of each other represent hydrogen, halogen, hydroxy, trifluoromethyl, methoxy, ethoxy, methyl, or ethyl.

In another embodiment of the present invention, $R_5$, $R_6$, and $R_7$, independently of each other represent hydrogen, halogen, —$NH_2$, hydroxy, trifluoromethyl, methoxy, ethoxy, cyano, acetyl, acetamido, methyl, or ethyl, and $R_4$ and $R_8$ independently of each other represent hydrogen, halogen, hydroxy, trifluoromethyl, methoxy, ethoxy, cyano, acetyl, acetamido, methyl, or ethyl.

In yet another embodiment of the compounds of formula Ia or Ib, $R_4$, $R_5$, $R_6$, $R_7$, and $R_8$ independently of each other represent hydrogen, fluoro, or chloro.

In yet another embodiment of the compounds of formula Ia or Ib, at least three of $R_4$, $R_5$, $R_6$, $R_7$, or $R_8$ represent hydrogen.

In a further presently preferred embodiment of the compounds of formula Ia or Ib, $R_5$, $R_7$, and $R_8$ represent hydrogen.

In a further presently preferred embodiment of the compounds of formula Ia or Ib, $R_5$, $R_6$, $R_7$, and $R_8$ represent hydrogen.

In a further presently preferred embodiment of the compounds of formula Ia or Ib, $R_4$, $R_5$, $R_7$, and $R_8$ represent hydrogen.

In yet another embodiment of the compounds of formula Ia or Ib, $R_4$, $R_7$, and $R_8$, or $R_6$, $R_7$, and $R_8$, or $R_4$, $R_6$, $R_7$, and $R_8$, or $R_4$, $R_6$, and $R_8$, or $R_4$, $R_6$, and $R_7$ represent hydrogen.

In a further presently preferred embodiment of the compounds of formula Ia or Ib, $R_1$ is methyl and $R_2$ is chloro.

In a further presently preferred embodiment of the compounds of formula Ia or Ib, $R_3$ represents $C_{1-4}$alkyl, $C_{1-4}$alkenyl, or $C_{1-4}$hydroxyalkyl, each of which are optionally substituted with one or more, same or different substituents selected from the group consisting of halogen, hydroxy, mercapto, —$NH_2$, carboxy, $CONH_2$, nitro, oxo, —$S(O)_2NH_2$, $C_{1-2}$hydroxyalkyl, $C_{1-2}$alkoxy, $C_{1-2}$alkoxycarbonyl, $C_{1-2}$ureido, $C_{1-2}$thioureido, $C_{1-2}$alkylcarbonyloxy, $C_{1-2}$alkoxycarbonyloxy, $C_{1-2}$alkoxysulfonyloxy, $C_{1-2}$alkoxycarbamoyl, $C_{1-2}$aminocarbonyl, $C_{1-2}$alkylthio, $C_{1-2}$amino, $C_{1-2}$imino, $C_{1-2}$aminosulfonyl, $C_{1-2}$aminocarbonyloxy, $C_{1-2}$alkylsulfonylamino, $C_{1-2}$alkoxyimino, $C_{1-2}$alkylcarbonylamino, $C_{1-2}$alkylsulfonyl, $C_{2-5}$heteroaryl, $C_{2-5}$heterocycloalkyl, $C_{3-5}$heterocycloalkenyl, the last 22 of which are optionally further substituted with one or more, same or different substituents selected from the group consisting of hydroxy, —$NH_2$, carboxy, $CONH_2$, oxo, or $C_{1-3}$alkyl, provided that the compound is not

[4-(2-Amino-phenylamino)-2-chloro-phenyl]-(2-methyl-5-{1-[2-(tetrahydro-pyran-2-yloxy)-ethyl]-1H-[1,2,3]triazol-4-yl}-phenyl)-methanone, or

[4-(2-Amino-phenylamino)-2-chloro-phenyl]-{5-[1-(2-hydroxy-ethyl)-1H-[1,2,3]triazol-4-yl]-2-methyl-phenyl}-methanone.

In a further preferred embodiment of the compounds of formula Ia or Ib, $R_3$ represents $C_{1-3}$alkyl, $C_{1-3}$alkenyl or $C_{1-3}$hydroxyalkyl, each of which are optionally substituted with one or more, same or different substituents selected from the group consisting of hydroxy, —$NH_2$, carboxy, chloro, $CONH_2$, oxo, —$S(O)_2NH_2$, $C_{1-2}$hydroxyalkyl, $C_{1-2}$alkoxy, $C_{1-2}$alkoxycarbonyl, $C_{0-2}$ureido, $C_{1-2}$aminocarbonyl, $C_{1-2}$amino, $C_{1-2}$alkylsulfonylamino, $C_{2-5}$heterocycloalkyl, the last 8 of which are optionally further substituted with one or more, same or different substituents selected from the group consisting of hydroxy or $C_{1-2}$alkyl, provided that the compound is not

[4-(2-Amino-phenylamino)-2-chloro-phenyl]-(2-methyl-5-{1-[2-(tetrahydro-pyran-2-yloxy)-ethyl]-1H-[1,2,3]triazol-4-yl}-phenyl)-methanone, or

[4-(2-Amino-phenylamino)-2-chloro-phenyl]-{5-[1-(2-hydroxy-ethyl)-1H-[1,2,3]triazol-4-yl]-2-methyl-phenyl}-methanone.

In a further preferred embodiment of the compounds of formula Ia or Ib, $R_3$ represents methyl, ethyl, propyl, propenyl, all of which are substituted with one, two, three, or four, same or different substituents selected from the group consisting of hydroxy, $CONH_2$, oxo, diethylamino, ethylaminocarbonyl, methyl, hydroxymethyl, pyrrolidinyl, morpholinyl, chloro, $H_2N$—$C(O)$—$NH$—, methoxycarbonyl, methoxy, —$NH_2$, ethoxycarbonyl, ethoxy, methylsulfonylamino, —$S(O)_2NH_2$, tetrahydropyranyl, [1,3]-dioxolanyl, ethylamino, piperazinyl, the latter four optionally substituted with one, two, three, or four, same or different substituents selected from the group consisting of methyl or ethyl.

In a further preferred embodiment of the compounds of formula Ia or Ib, $R_3$ is 2-hydroxyethyl, 3-hydroxypropyl, carbamoylmethyl, 2,3-dihydroxypropyl, 2-(methylsulfonylamino)ethyl, sulfonylaminopropyl, 2,2-dimethyl-[1,3]dioxolan-4-ylmethyl, 2-(tetrahydro-pyran-2-yloxy)-ethyl, 3-(tetrahydro-pyran-2-yloxy)-propyl, ethoxycarbonylmethyl, carboxymethyl, ethylaminocarbonylmethyl, (2-hydroxy-1,1-dimethyl-ethyl)aminocarbonylmethyl, 1-pyrrolidin-1-yl-ethanone, 1-morpholin-4-yl-ethanone, 2-chloroethyl, 1-hydroxy-1-methyl-ethyl, acetyl, 1-amino-1-methyl-ethyl, methoxycarbonyl, carboxy, hydroxymethyl, 3-hydroxy-propenyl, 2-amino-ethyl, methylurea, 2-morpholin-4-yl-ethyl, (4-methyl-piperazin-1-yl)-ethyl, 2-diethylamino-ethyl, 2-(2-hydroxy-ethylamino)-ethyl, propylaminoethyl, or diethylamine.

Specific examples of compounds of formula I may be selected from the group consisting of

[2-Chloro-4-(2,4-difluoro-phenylamino)-phenyl]-(2-methyl-5-{1-[2-(tetrahydro-pyran-2-yloxy)-ethyl]-1H-[1,2,3]triazol-4-yl}-phenyl)-methanone (compound 101),

[2-Chloro-4-(2,4-difluoro-phenylamino)-phenyl]-{5-[1-(2-hydroxy-ethyl)-1H-[1,2,3]triazol-4-yl]-2-methyl-phenyl}-methanone (compound 102),

[2-Chloro-4-(2,4-difluoro-phenylamino)-phenyl]-(2-methyl-5-{1-[3-(tetrahydro-pyran-2-yloxy)-propyl]-1H-[1,2,3]triazol-4-yl}-phenyl)-methanone (compound 103),

[2-Chloro-4-(2,4-difluoro-phenylamino)-phenyl]-{5-[1-(3-hydroxy-propyl)-1H-[1,2,3]triazol-4-yl]-2-methyl-phenyl}-methanone (compound 104),

[2-Chloro-4-(2,4-difluoro-phenylamino)-phenyl]-{5-[1-(2,2-dimethyl-[1,3]dioxolan-4-ylmethyl)-1H-[1,2,3]triazol-4-yl]-2-methyl-phenyl}-methanone (compound 105),

[2-Chloro-4-(2,4-difluoro-phenylamino)-phenyl]-{5-[1-(2,3-dihydroxy-propyl)-1H-[1,2,3]triazol-4-yl]-2-methyl-phenyl}-methanone (compound 106), 2-(4-{3-[2-Chloro-4-(2,4-difluoro-phenylamino)-benzoyl]-4-methyl-phenyl}-[1,2,3]triazol-1-yl)-acetamide (compound 107), 3-(4-{3-[2-Chloro-4-(2,4-difluoro-phenylamino)-benzoyl]-4-methyl-phenyl}-[1,2,3]triazol-1-yl)-propane-1-sulfonic acid amide (compound 108), N-[2-(4-{3-[2-Chloro-4-(2,4-difluoro-phenylamino)-benzoyl]-4-methyl-phenyl}-[1,2,3]triazol-1-yl)-ethyl]-methanesulfonamide (compound 109), (4-{3-[2-Chloro-4-(2,4-difluoro-phenylamino)-benzoyl]-4-methyl-phenyl}-[1,2,3]triazol-1-yl)-acetic acid ethyl ester (compound 110), (4-{3-[2-Chloro-4-(2,4-difluoro-phenylamino)-benzoyl]-4-methyl-phenyl}-[1,2,3]triazol-1-yl)-acetic acid (compound 111), 2-(4-{3-[2-Chloro-4-(2,4-difluoro-phenylamino)-benzoyl]-4-methyl-phenyl}-[1,2,3]triazol-1-yl)-N-ethyl-acetamide (compound 112), 2-(4-{3-[2-Chloro-4-(2,4-difluoro-phenylamino)-benzoyl]-4-methyl-phenyl}-[1,2,3]triazol-1-yl)-N-(2-hydroxy-1,1-dimethyl-ethyl)-acetamide (compound 113), 2-(4-{3-[2-Chloro-4-(2,4-difluoro-phenylamino)-benzoyl]-4-methyl-phenyl}-[1,2,3]triazol-1-yl)-1-pyrrolidin-1-yl-ethanone (compound 114), 2-(4-{3-[2-Chloro-4-(2,4-difluoro-phenylamino)-benzoyl]-4-methyl-phenyl}-[1,2,3]triazol-1-yl)-1-morpholin-4-yl-ethanone (compound 115),

[2-Chloro-4-(4-trifluoromethyl-phenylamino)-phenyl]-{5-[4-(2-hydroxy-ethyl)-[1,2,3]triazol-1-yl]-2-methyl-phenyl}-methanone (compound 116), (2-Chloro-4-o-tolylamino-phenyl)-{5-[4-(2-hydroxy-ethyl)-[1,2,3]triazol-1-yl]-2-methyl-phenyl}-methanone (compound 117),

[2-Chloro-4-(2-chloro-4-fluoro-phenylamino)-phenyl]-{5-[4-(2-hydroxy-ethyl)-[1,2,3]triazol-1-yl]-2-methyl-phenyl}-methanone (compound 118),

[2-Chloro-4-(2,4-difluoro-phenylamino)-phenyl]-(2-methoxy-5-{1-[2-(tetrahydro-pyran-2-yloxy)-ethyl]-1H-[1,2,3]triazol-4-yl}-phenyl)-methanone (compound 119),

[2-Chloro-4-(2,4-difluoro-phenylamino)-phenyl]-{5-[1-(2-hydroxy-ethyl)-1H-[1,2,3]triazol-4-yl]-2-methoxy-phenyl}-methanone (compound 120),

[2-Chloro-4-(4-fluoro-phenylamino)-phenyl]-(2-methyl-5-{1-[2-(tetrahydro-pyran-2-yloxy)-ethyl]-1H-[1,2,3]triazol-4-yl}-phenyl)-methanone (compound 121),

[2-Chloro-4-(4-fluoro-phenylamino)-phenyl]-{5-[1-(2-hydroxy-ethyl)-1H-[1,2,3]triazol-4-yl]-2-methyl-phenyl}-methanone (compound 122),

[2-Chloro-4-(4-fluoro-phenylamino)-phenyl]-{5-[1-(2,2-dimethyl-[1,3]dioxolan-4-ylmethyl)-1H-[1,2,3]triazol-4-yl]-2-methyl-phenyl}-methanone (compound 123),

[2-Chloro-4-(4-fluoro-phenylamino)-phenyl]-{5-[1-(2,3-dihydroxy-propyl)-1H-[1,2,3]triazol-4-yl]-2-methyl-phenyl}-methanone (compound 124), 2-(4-{3-[2-Chloro-4-(4-fluoro-phenylamino)-benzoyl]-4-methyl-phenyl}-[1,2,3]triazol-1-yl)-acetamide (compound 125),

[2-chloro-4-(2,4-difluoro-phenylamino)-phenyl]-{5-[1-(2-chloro-ethyl)-1H-[1,2,3]triazol-4-yl]-2-methyl-phenyl}-methanone (compound 126)

[2-Chloro-4-(4-fluoro-phenylamino)-phenyl]-{5-[4-(2-hydroxy-ethyl)-[1,2,3]triazol-1-yl]-2-methyl-phenyl}-methanone (compound 127),

[2-Chloro-4-(2,4-difluoro-phenylamino)-phenyl]-{5-[4-(2-hydroxy-ethyl)-[1,2,3]triazol-1-yl]-2-methyl-phenyl}-methanone (compound 128),

[2-Chloro-4-(2,4-difluoro-phenylamino)-phenyl]-{5-[4-(1-hydroxy-1-methyl-ethyl)-[1,2,3]triazol-1-yl]-2-methyl-phenyl}-methanone (compound 129), 1-(1-{3-[2-Chloro-4-(2,4-difluoro-phenylamino)-benzoyl]-4-methyl-phenyl}-1H-[1,2,3]triazol-4-yl)-ethanone (compound 130), {5-[4-(1-Amino-1-methyl-ethyl)-[1,2,3]triazol-1-yl]-2-methyl-phenyl}-[2-chloro-4-(2,4-difluoro-phenylamino)-phenyl]-methanone (compound 131), 1-{3-[2-Chloro-4-(2,4-difluoro-phenylamino)-benzoyl]-4-methyl-phenyl}-1H-[1,2,3]triazole-4-carboxylic acid methyl ester (compound 132), 1-{3-[2-Chloro-4-(2,4-difluoro-phenylamino)-benzoyl]-4-methyl-phenyl}-1H-[1,2,3]triazole-4-carboxylic acid (compound 133),

[2-Chloro-4-(2,4-difluoro-phenylamino)-phenyl]-[5-(4-hydroxymethyl-[1,2,3]triazol-1-yl)-2-methyl-phenyl]-methanone (compound 134),

[2-Chloro-4-(2,4-difluoro-phenylamino)-phenyl]-{5-[4-(3-hydroxy-propenyl)-[1,2,3]triazol-1-yl]-2-methyl-phenyl}-methanone (compound 135), {5-[4-(2-Amino-ethyl)-[1,2,3]triazol-1-yl]-2-methyl-phenyl}-[2-chloro-4-(2,4-difluoro-phenylamino)-phenyl]-methanone (compound 136), (1-{3-[2-Chloro-4-(2,4-difluoro-phenylamino)-benzoyl]-4-methyl-phenyl}-1H-[1,2,3]triazol-4-ylmethyl)-urea (compound 137),

[2-Chloro-4-(2,4-difluoro-phenylamino)-phenyl]-{2-methyl-5-[4-(2-morpholin-4-yl-ethyl)-[1,2,3]triazol-1-yl]-phenyl}-methanone (compound 138),

[2-Chloro-4-(2,4-difluoro-phenylamino)-phenyl]-(2-methyl-5-{4-[2-(4-methyl-piperazin-1-yl)-ethyl]-[1,2,3]triazol-1-yl}-phenyl)-methanone (compound 139),
(2-Chloro-4-(2,4-difluoro-phenylamino)-phenyl]-{5-[4-(2-diethylamino-ethyl)-[1,2,3]triazol-1-yl]-2-methyl-phenyl}-methanone (compound 140),
[2-Chloro-4-(2,4-difluoro-phenylamino)-phenyl]-(5-{4-[2-(2-hydroxy-ethylamino)-ethyl]-[1,2,3]triazol-1-yl}-2-methyl-phenyl)-methanone (compound 141),
[2-Chloro-4-(2,4-difluoro-phenylamino)-phenyl]-{2-methyl-5-[4-(2-propylamino-ethyl)-[1,2,3]triazol-1-yl]-phenyl}-methanone (compound 142),
[2-Chloro-4-(4-fluoro-2-methyl-phenylamino)-phenyl]-{5-[4-(2-hydroxy-ethyl)-[1,2,3]triazol-1-yl]-2-methyl-phenyl}-methanone (compound 143),
[2-Chloro-4-(2-methoxy-phenylamino)-phenyl]-{5-[4-(2-hydroxy-ethyl)-[1,2,3]triazol-1-yl]-2-methyl-phenyl}-methanone (compound 144),
[2-Chloro-4-(4-chloro-2-methyl-phenylamino)-phenyl]-{5-[4-(2-hydroxy-ethyl)-[1,2,3]triazol-1-yl]-2-methyl-phenyl}-methanone (compound 145),
[2-Chloro-4-(4-methoxy-phenylamino)-phenyl]-{5-[4-(2-hydroxy-ethyl)-[1,2,3]triazol-1-yl]-2-methyl-phenyl}-methanone (compound 146),
[2-Chloro-4-(2,4-difluoro-phenylamino)-phenyl]-{5-[4-(2-ethylamino-ethyl)-[1,2,3]triazol-1-yl]-2-methyl-phenyl}-methanone (compound 147),
[4-(2,4-Difluoro-phenylamino)-2-methyl-phenyl]-{5-[4-(2-hydroxy-ethyl)-[1,2,3]triazol-1-yl]-2-methyl-phenyl}-methanone (compound 148),
[4-(3-Chloro-4-fluoro-phenylamino)-2-methyl-phenyl]-{5-[4-(2-hydroxy-ethyl)-[1,2,3]triazol-1-yl]-2-methyl-phenyl}-methanone (compound 149),
{5-[4-(2-Hydroxy-ethyl)-[1,2,3]triazol-1-yl]-2-methyl-phenyl}-(2-methyl-4-phenylamino-phenyl)-methanone (compound 150),
1-[3-(4-{5-[4-(2-Hydroxy-ethyl)-[1,2,3]triazol-1-yl]-2-methyl-benzoyl}-3-methyl-phenylamino)-phenyl]-ethanone (compound 151),
3-(4-{5-[4-(2-Hydroxy-ethyl)-[1,2,3]triazol-1-yl]-2-methyl-benzoyl}-3-methyl-phenylamino)-benzonitrile (compound 152),
{5-[4-(2-Hydroxy-ethyl)-[1,2,3]triazol-1-yl]-2-methyl-phenyl}-[2-methyl-4-(3-trifluoromethyl-phenylamino)-phenyl]-methanone (compound 153),
[4-(3,4-Difluoro-phenylamino)-2-methyl-phenyl]-{5-[4-(2-hydroxy-ethyl)-[1,2,3]triazol-1-yl]-2-methyl-phenyl}-methanone (compound 154),
[4-(3,4-Dimethyl-phenylamino)-2-methyl-phenyl]-{5-[4-(2-hydroxy-ethyl)-[1,2,3]triazol-1-yl]-2-methyl-phenyl}-methanone (compound 155),
[4-(3-Chloro-2-methyl-phenylamino)-2-methyl-phenyl]-{5-[4-(2-hydroxy-ethyl)-[1,2,3]triazol-1-yl]-2-methyl-phenyl}-methanone (compound 156),
[4-(3,4-Dichloro-phenylamino)-2-methyl-phenyl]-{5-[4-(2-hydroxy-ethyl)-[1,2,3]triazol-1-yl]-2-methyl-phenyl}-methanone (compound 157),
N-[3-(4-{5-[4-(2-Hydroxy-ethyl)-[1,2,3]triazol-1-yl]-2-methyl-benzoyl}-3-methyl-phenylamino)-phenyl]-acetamide (compound 158),
[2-Chloro-4-(2,4-difluoro-phenylamino)-phenyl]-{2-chloro-5-[4-(2-hydroxy-ethyl)-[1,2,3]triazol-1-yl]-phenyl}-methanone (compound 159),
[2-Chloro-4-(3-fluoro-phenylamino)-phenyl]-{5-[4-(2-hydroxy-ethyl)-[1,2,3]triazol-1-yl]-2-methyl-phenyl}-methanone (compound 160),
[2-Chloro-4-(3-chloro-phenylamino)-phenyl]-{5-[4-(2-hydroxy-ethyl)-[1,2,3]triazol-1-yl]-2-methyl-phenyl}-methanone (compound 161),
(2-Chloro-4-m-tolylamino-phenyl)-{5-[4-(2-hydroxy-ethyl)-[1,2,3]triazol-1-yl]-2-methyl-phenyl}-methanone (compound 162),
[2-Chloro-4-(3-methoxy-phenylamino)-phenyl]-{5-[4-(2-hydroxy-ethyl)-[1,2,3]triazol-1-yl]-2-methyl-phenyl}-methanone (compound 163),
[2-Chloro-4-(2,3-dichloro-phenylamino)-phenyl]-{5-[4-(2-hydroxy-ethyl)-[1,2,3]triazol-1-yl]-2-methyl-phenyl}-methanone (compound 164),
[2-Chloro-4-(3,5-dimethyl-phenylamino)-phenyl]-{5-[4-(2-hydroxy-ethyl)-[1,2,3]triazol-1-yl]-2-methyl-phenyl}-methanone (compound 165),
[2-Chloro-4-(2,5-difluoro-phenylamino)-phenyl]-{5-[4-(2-hydroxy-ethyl)-[1,2,3]triazol-1-yl]-2-methyl-phenyl}-methanone (compound 166), and
[2-Chloro-4-(3,5-difluoro-phenylamino)-phenyl]-{5-[4-(2-hydroxy-ethyl)-[1,2,3]triazol-1-yl]-2-methyl-phenyl}-methanone (compound 167).

In yet another embodiment of the present invention of the compounds of formula Ia, at least one of $R_5$, $R_6$, $R_7$, or $R_8$ is not hydrogen when $R_4$ is —$NH_2$, or at least one of $R_4$, $R_5$, $R_6$, or $R_7$ is not hydrogen when $R_8$ is —$NH_2$.

Methods of Preparation

The compounds of the present invention may be prepared in a number of ways well known to those skilled in the art of organic synthesis. The compounds of the present invention may be synthesised using the methods outlined below, together with methods known in the art of synthetic organic chemistry, or variations thereof as appreciated by those skilled in the art. Preferred methods include, but are not limited to, those described below.

The compounds of formula Ia and Ib may be prepared using the reactions and techniques described in this section. The reactions are performed in solvents that are appropriate with respect to the reagents and materials employed and that are suitable for the transformations being effected. Also, in the synthetic methods described below, it is to be understood that all proposed reaction conditions, including choice of solvent, reaction atmosphere, reaction temperature, duration of experiment and work-up procedures, are chosen to be conditions of standard for that reaction, which should be readily recognised by one skilled in the art. It is understood by one skilled in the art of organic synthesis, that the functionality present on various positions of the molecules used as the starting compounds or intermediates in the syntheses, must be compatible with the reagents and reactions proposed. Not all compounds of formula I falling into a given class may be compatible with some of the reaction conditions required in some of the methods described. Such restrictions of substituents or functional groups which are compatible with the reaction conditions will be readily apparent to one skilled in the art and alternative methods can be used.

Compounds according to the present invention may be prepared by a process comprising coupling of an terminal alkyne of formula IIa with an azide of formula IIIa to give a compound of formula Ia, as shown in Scheme 1; or similarly by a process comprising coupling of an azide of formula IIb with an terminal alkyne of formula IIIb yo give a compound of formula Ib, as shown in Scheme 1; where $R_1$, $R_2$, $R_3$, $R_4$, $R_5$, $R_6$, $R_7$ and $R_8$ are as defined above; except that any substituents or functional groups which are potentially reactive in the coupling reaction may be protected before the coupling reaction is performed, and the protective groups removed subsequently.

Scheme 1

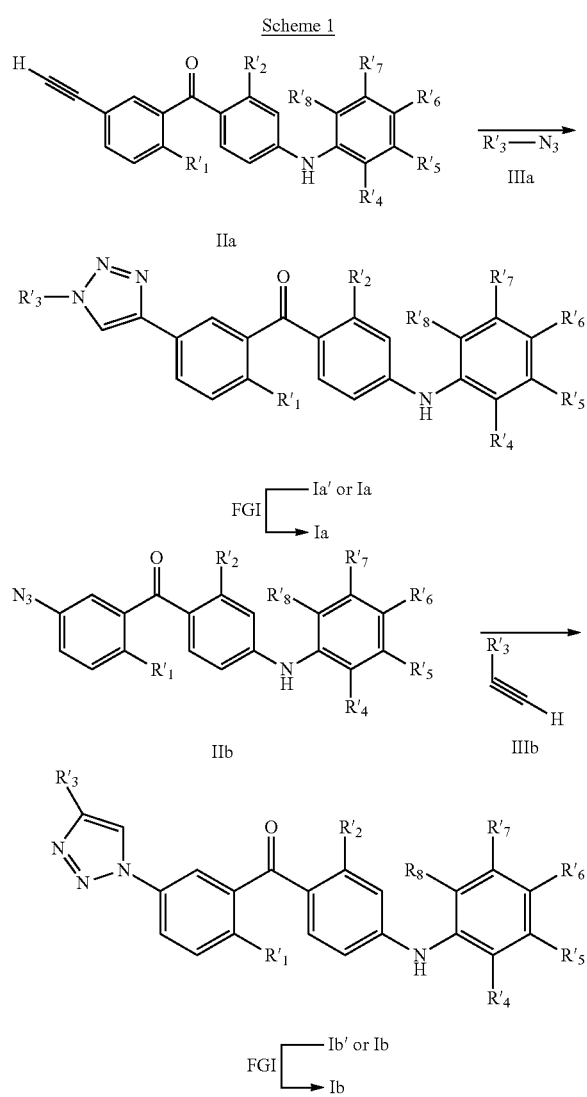

FGI: Functional group interconversion R'$_1$, R'$_2$, R'$_3$, R'$_4$, R'$_5$, R'$_5$, R'$_6$, R'$_7$ and R'$_8$ stands for R$_1$, R$_2$, R$_3$, R$_4$, R$_5$, R$_6$, R$_7$ and R$_8$ respectively or any suitable FG (functional group) which may be transformed to R$_1$, R$_2$, R$_3$, R$_4$, R$_5$, R$_6$, R$_7$ and R$_8$.

The above coupling reaction is carried out by using a method for the formation of 1,4 disubstituted triazoles well known to one skilled in the art of organic synthesis (see e.g. WO 03/101972, Angew. Chem Int. Ed. 2002, 41, No. 14, JOC 2002, 67, 3057-3064, and references cited therein). A preferred method is the copper(I) catalysed method which comprises coupling of an azide with an terminal alkyne at room temperature or higher (e.g. up to 80° C.).

Different copper sources may be used in the process, non-limiting examples of which are Cu(I)I, Cu(I)Br, Cu(I)Cl, Cu(I)OAc and Cu(0). A presently preferred source is Cu(II)SO$_4$.5H$_2$O in the presence of a suitable reducing agent like sodium ascorbate. The amount of Cu source used in this catalytic process is typically in the range 0.1 to 10% by mole relative to the amount of the alkyne or azide used.

The reaction is typically performed at low temperatures (e.g. 25° C.) in solvents such as methanol, ethanol, tert-butanol, 1,4-dioxane, acetonitrile, dimethylsulfoxide (DMSO), acetone, N,N-dimethylformamide (DMF), N-methylpyrrolidinone (NMP) or tetrahydrofuran (THF). When Cu(II)SO$_4$.5H$_2$O in the presence of a reducing agent is used as the catalytic system, a minor amount of water (2-40%, v/v) is typically added to the reaction.

The above coupling may also be performed non-catalytically (without Cu) but thermally, simply by heating. However, this process may also lead to 1,5-disubstituted triazoles.

Compounds according to the present invention of the general formula IIa may be prepared by several methods known to those skilled in the art of organic synthesis. One useful sequence is shown in Scheme 2. The key step comprises the coupling of an iodide of general formula IV with ethynyltrimethylsilane to afford a compound of general formula III. The coupling is typically performed in the presence of a catalytic amount of a palladium(0) source, e.g. pd$_2$(dba)$_3$; a catalytic amount of a cupper(I) salt, e.g cupper(I)iodide; and a ligand, e.g. triphenylphosphine, to stabilise the catalytic system. The reaction is well described in the literature, also called as Sonogashira reaction (see for example: Sonogashira, K. In Metal-Catalyzed Reactions, Diederich, F., Stang, P. J., Eds.; Wiley-VCH: New York, 1998). The protected compound III may then be deprotected to the corresponding terminal acetylene of general formula IIa by treatment with e.g. K$_2$CO$_3$ in methanol at RT.

The iodide of the general formula IV may be prepared by a standard diazotation of the amine with the general formula V followed by treatment of the formed diazonium salt with potassium iodide (see preparation 5 as a non-limiting example for generally applicable experimental details). The amine of the general formula V may be formed by a reduction of the nitro compound of general formula VI using standard reducing agents. Examples of such reducing agents presently include, but are not limited to, stannous chloride dihydrate, hydrogen, ammonium formiate or hydrazine hydrate and a catalytic amount of palladium on carbon. The azide of the general formula IIb may be prepared from the amine of the general formula V by treatment of trifluoromethansulfonyl azide in the presence of a catalytic amount of copper salt, e.g. copper(II) sulphate pentahydrate as described in the literature, for example by Liu, Q.; Yitzhak, T.; Org. Lett. 2003, 5, 2571-2572.

Scheme 2

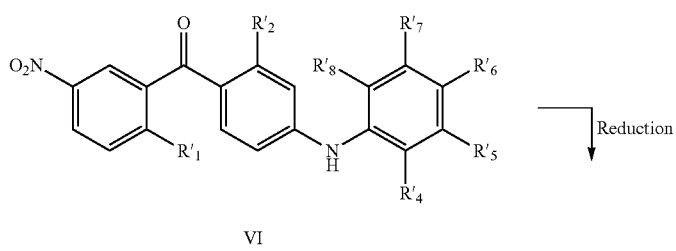

-continued

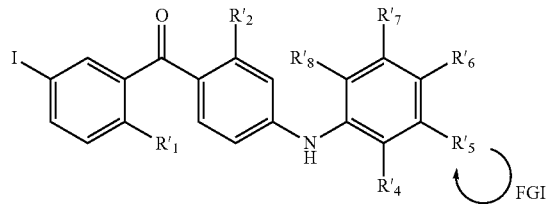

IV

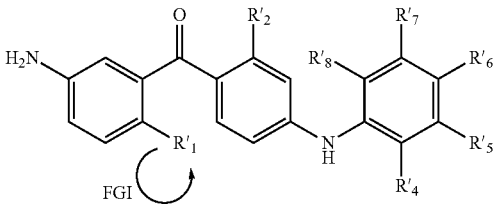

V

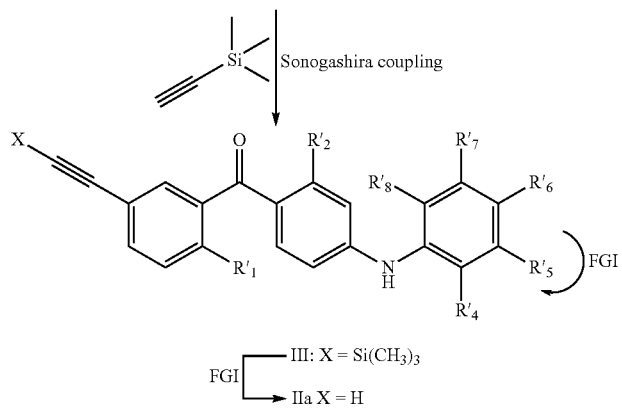

III: X = Si(CH₃)₃
IIa X = H

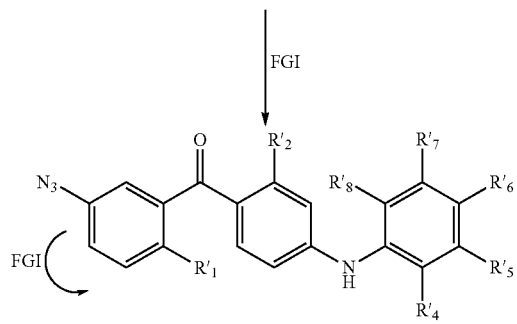

IIb

FGI: Functional group interconversion R′₁, R′₂, R′₃, R′₄, R′₅, R′₅, R′₆, R′₇ and R′₈ stands for R₁, R₂, R₃, R₄, R₅, R₆, R₇ and R₈ respectively or any suitable FG (functional group) which may be transformed to R₁, R₂, R₃, R₄, R₅, R₆, R₇ and R₈

Compounds according to the present invention of the general formula VI may be prepared by several methods known to those skilled in the art of organic synthesis. One useful sequence is shown in Scheme 3.

The first key step comprises the coupling of an iodide of the general formula IX with an ester (an activated acid) of the general formula X to give the benzophenone of the general formula VII, e.g. by using methods described for the preparation of other ketones in J. Am. Chem. Soc. 1973, 95:14, 4763-4765. The coupling reaction may be achieved by transforming the iodide IX into a reactive organometallic intermediate, such as by treatment with iso-propyl magnesium chloride to afford the corresponding magnesium derivative. Mixing of the reactive magnesium derivative with the ester of the general formula X gives the product of the general formula VII.

Alternatively, the reactive magnesium derivative may by transmetalated to zinc, by treatment with a zinc salt, e.g. zinc chloride, or ZnBr₂ or ZnI₂, and then be coupled with the acid halide, such as the acid chloride of the acid of the general formula XI, in the presence of a catalytic amount of Pd(0)/ligand system. Examples of such palladium catalysts include but are not limited to tetrakis(triphenylphosphine)palladium (0), tetrakis(triphenylarsine)palladium(0), dichlorobis(triphenylphosphine)palladium(II), or benzylchlorobis(triphenylphosphine)palladium(II). Alternatively, the organozinc compound is coupled with the acid halide, such as the acid chloride in the presence or mediated by an equimolar or substoichiometric or catalytic amount of a copper (I) or (II) salts, such as copper(II)acetate or the soluble complex CuCN.2LiCl or CuCN.2LiBr. The coupling reaction may typically be performed at room temperature in inert solvents such as 1,4-dioxane, toluene, benzene, and tetrahydrofuran under an inert atmosphere, e.g. under argon or nitrogen.

The second key step comprises the coupling of a bromide of the general formula VII with an amine of the general formula VIII to give the aminobenzophenone of the general formula VI. The coupling reaction is carried out by using a method for the formation of diphenylamines well known to one skilled in the art of organic synthesis. The preferred method is the palladium catalysed amination method which comprises coupling of an amine with an arylhalogenide (or aryltriflate) in the presence of a base, a suitable Pd source, and a suitable phosphine ligand in an inert solvent.

Different palladium compounds may be used in the process, non-limiting examples of which are palladium(II) acetate, palladium(II) chloride, palladium(II) bromide, dichlorobis(triphenylphosphine)palladium(II), tetrakis (triphenylphosphine)palladium(0), tris(dibenzylideneacetone)dipalladium(0). The preferred phosphine ligands include, but are not limited to, racemic or non-racemic 2,2′-bis(diphenylphosphino)-1,1′-binaphthyl (hereinafter referred to as BINAP), tri-o-tolylphosphine, tri-tert-butylphosphine, 1,1′-bis(diphenylphosphino)-ferrocene, bis[(2-diphenylphosphino)phenyl]ether (DPEphos), 2-dicyclohexylphosphanyl-2′-dimethylaminobiphenyl, 2-(di-tert-butylphosphino)biphenyl and 9,9-dimethyl-4,6-bis (diphenylphosphino)xanthene (Xantphos). The amount of palladium and ligand used in this catalytic process may be typically in the range 0.1 to 10% by mole relative to the amount of the aromatic halide (or triflate) used. Especially sodium-tert-butoxide (NaOt-Bu) and caesium carbonate (Cs₂CO₃) have proven to be preferred bases in this process, but other bases may be used as well. The reaction is typically performed at elevated temperatures (80-120° C.) in inert solvents such as 1,4-dioxane, toluene, benzene, and tetrahydrofuran under an inert atmosphere, e.g. argon or nitrogen.

The thioesters of the general formula X may for example be prepared from the acid of the general formula XI by treatment with 2,2'-dithiopyridine in the presence of triphenylphosphine (see e.g. preparation 1 for generally applicable nonliting experimental details), such as described in Tetrahedron Letters Vol. 22, No. 46, pp. 4647-4650, 1981. Other general methods for the preparation of the thioesters of general formula X can be for example be found in Tetrahedron Letters No. 31, pp. 2875-2878, 1979 and Org. Letters 2003, Vol 5, No. 10, pp 1633-1635 and references cited therein.

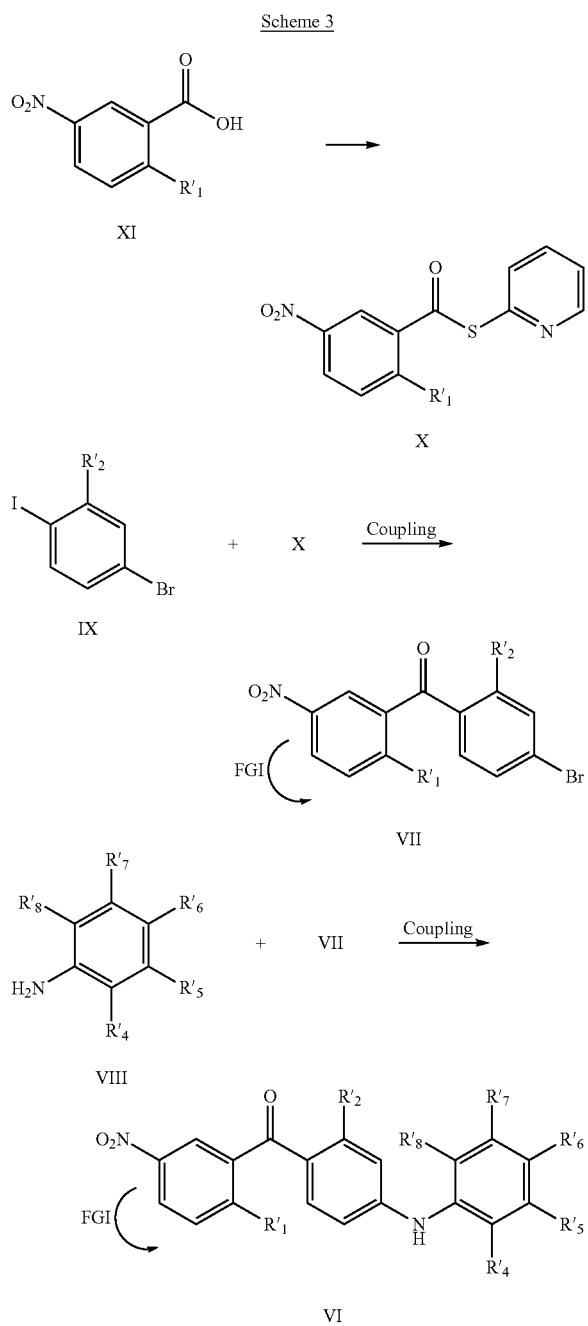

FGI: Functional group interconversion $R'_1, R'_2, R'_3, R'_4, R'_5, R'_5, R'_6, R'_7$ and $R'_8$ stands for $R_1, R_2, R_3, R_4, R_5, R_6, R_7$ and $R_8$ respectively or any suitable FG (functional group) which may be transformed to $R_1, R_2, R_3, R_4, R_5, R_6, R_7$ and $R_8$ Compounds according to the present invention may in special cases be prepared by a simple functional group interconversion (FGI), meaning a standard process, known to those skilled in the art of organic synthesis, where a functional group in compounds with the general formula I or I' is transformed into a different functional group in one or more synthetic steps, leading to a new compound with the general formula I. Examples of such processes include, but are not limited to, hydrolysis of an ester to give an acid under basic conditions, deprotection of a methylether to give a phenol by treatment with e.g. borontribromide ($BBr_3$), and e.g. catalytic hydrogenation of an olefin to give a saturated hydrocarbon. Non limiting examples of such transformations are described in "Comprehensive Organic Transformations", by R. C. Larock, VCH 1989 and references cited therein, which are hereby incorporated as reference and in general procedures. Especially, the use of general protective groups in one or more synthetic steps may be convenient in the synthesis of compounds with the general formula I. Examples of such general protective groups include, but are not limited to, methyl, ethyl, tert-butyl or benzyl esters as protective groups of an hydroxy group; tetrahydropyranyl- or silyl-ethers as protective groups of an hydroxy group or terminal alkyne.

As shown in Scheme 1, 2 and 3 each intermediate compound may be transformed by an FGI process as described above to give new compounds with the same general formula (e.g. an hydroxy group may be protected as an tert-butyl-dimethyl-silyl ether). This is only to illustrate the flexibility in the synthesis, and in general the described sequence of processes is only one of many possible strategies for the synthesis of compounds of the present invention. That is, it may be more advantageous in some cases to alter the sequence of the processes described above. The described sequence of processes is not considered as being limiting of the preparation of compounds of the present invention of general formula Ia or Ib, and alteration of the reaction sequence may be an alternative for those skilled in the art of organic synthesis. Readily available intermediates may serve as starting point for the synthesis of various series of compounds covered by the general formula Ia and Ib.

The synthesis of various aminobenzophenones and general methods useful in for the synthesis of said intermediates and the benzophenones of the present invention can for example be found in WO 98/32730, WO 01/05744, WO 01/05746, WO 01/05749, WO 01/05751, WO 01/05745, WO 01/42189, WO 01/90074, WO 02/083622, WO 03/018535, WO 02/076447, and WO 04/056762, and references cited therein, all of which are hereby incorporated as references.

Pharmaceutical Compositions

In another aspect, the invention relates to a pharmaceutical composition comprising, as an active component, a compound of formula Ia or Ib together with a pharmaceutically acceptable excipient, carrier or vehicle. Furthermore, the invention relates to the use of a compound of formula Ia or Ib for the preparation of a medicament for the prevention, treatment or amelioration of inflammatory diseases or conditions.

Pharmaceutical compositions of the invention may be in unit dosage form such as tablets, pills, capsules, powders, granules, elixirs, syrups, emulsions, ampoules, suppositories or parenteral solutions or suspensions; for oral, parenteral, opthalmic, transdermal, intra-articular, topical, pulmonal, nasal, buccal or rectal administration or in any other manner appropriate for the formulation of anti-inflammatory compounds and in accordance with accepted practices such as those disclosed in *Remington: The Science and Practice of Pharmacy.* 19th Ed., Mack Publishing Company, 1995. In the composition of the invention, the active component may be present in an amount of from about 0.01 to about 99%, such as 0.1% to about 10% by weight of the composition.

For oral administration in the form of a tablet or capsule, a compound of formula I may suitably be combined with an oral, non-toxic, pharmaceutically acceptable carrier such as ethanol, glycerol, water or the like. Furthermore, suitable binders, lubricants, disintegrating agents, flavouring agents and colourants may be added to the mixture, as appropriate. Suitable binders include, e.g., lactose, glucose, starch, gelatin, acacia gum, tragacanth gum, sodium alginate, carboxymethylcellulose, polyethylene glycol, waxes or the like. Lubricants include, e.g., sodium oleate, sodium stearate, magnesium stearate, sodium benzoate, sodium acetate, sodium chloride or the like. Disintegrating agents include, e.g., starch, methyl cellulose, agar, bentonite, xanthan gum or the like. Additional excipients for capsules include macrogols or lipids.

For the preparation of solid compositions such as tablets, the active compound of formula I is mixed with one or more excipients, such as the ones described above, and other pharmaceutical diluents such as water to make a solid preformulation composition containing a homogenous mixture of a compound of formula I. The term "homogenous" is understood to mean that the compound of formula I is dispersed evenly throughout the composition so that the composition may readily be subdivided into equally effective unit dosage forms such as tablets or capsules. The preformulation composition may then be subdivided into unit dosage forms containing from about 0.05 to about 1000 mg, in particular from about 0.1 to about 500 mg, of the active compound of the invention.

Liquid formulations for either oral or parenteral administration of the compound of the invention include, e.g., aqueous solutions, syrups, aqueous or oil suspensions and emulsion with edible oils such as cottonseed oil, sesame oil, coconut oil or peanut oil. Suitable dispersing or suspending agents for aqueous suspensions include synthetic or natural gums such as tragacanth, alginate, acacia, dextran, sodium carboxymethylcellulose, gelatin, methylcellulose or polyvinylpyrolidone.

For parenteral administration, e.g. intramuscular, intraperitoneal, subcutaneous or intravenous injection or infusion, the pharmaceutical composition preferably comprises a compound of formula I dissolved or solubilised in an appropriate, pharmaceutically acceptable solvent. For parenteral administration, the composition of the invention may include a sterile aqueous or non-aqueous solvent, in particular water, isotonic saline, isotonic glucose solution, buffer solution or other solvent conventionally used for parenteral administration of therapeutically active substances. The composition may be sterilised by, for instance, filtration through a bacteria-retaining filter, addition of a sterilising agent to the composition, irradiation of the composition, or heating the composition. Alternatively, the compound of the invention may be provided as a sterile, solid preparation, e.g. a freeze-dried powder, which is dissolved in sterile solvent immediately prior to use.

The composition intended for parenteral administration may additionally comprise conventional additives such as stabilisers, buffers or preservatives, e.g. antioxidants such as methylhydroxybenzoate or the like.

Compositions for rectal administration may be in the form of a suppository incorporating the active ingredient and a carrier such as cocoa butter, or in the form of an enema.

Compositions suitable for intra-articular administration may be in the form of a sterile aqueous preparation of the active ingredient which may be in microcrystalline form, for example, in the form of an aqueous microcrystalline suspension. Liposomal formulations or biodegradable polymer systems may also be used to present the active ingredient for both intra-articular and ophthalmic administration.

Compositions suitable for topical administration, including ophthalmic treatment, include liquid or semi-liquid preparations such as liniments, lotions, gels, applicants, oil-in-water or water-in-oil emulsions such as creams, ointments or pastes; or solutions or suspensions such as drops. For topical administration, the compound of formula I may typically be present in an amount of from 0.01 to 20% by weight of the composition, such as 0.1% to about 10%, but may also be present in an amount of up to about 50% of the composition.

Compositions for ophthalmic treatment may preferably additionally contain a cyclodextrin.

Compositions suitable for administration to the nasal or buccal cavity or for inhalation include powder, self-propelling and spray formulations, such as aerosols and atomizers. Such compositions may comprise a compound of formula I in an amount of 0.01-20%, e.g. 2%, by weight of the composition.

The composition may additionally comprise one or more other active components conventionally used in the treatment of various inflammatory diseases and conditions. Examples of such additional active components may be selected from the group consisting of glucocorticoids, vitamin D and vitamin D analogues, antihistamines, platelet activating factor (PAF) antagonists, anticholinergic agents, methylxanthines, β-adrenergic agents, COX-2 inhibitors, salicylates, indomethacin, flufenamate, naproxen, timegadine, gold salts, penicillamine, serum cholesterol lowering agents, retinoids, zinc salts and salicylazosulfapyridine.

In a further aspect, the invention relates to a method of treating inflammatory diseases or conditions, or ophthalmic diseases or conditions, or cancer, the method comprising administering, to a patient in need thereof, an effective amount of a compound of formula I.

A suitable dosage of the compound of the invention will depend, inter alia, on the age and condition of the patient, the severity of the disease to be treated and other factors well known to the practising physician. The compound may be administered either orally, parenterally or topically according to different dosing schedules, e.g. daily or with weekly intervals. In general a single dose will be in the range from 0.01 to 400 mg/kg body weight. The compound may be administered as a bolus (i.e. the entire daily dosis is administered at once) or in divided doses two or more times a day.

Inflammatory diseases or conditions contemplated for treatment with the present compounds are inflammatory diseases where modulation of cytokine expression and secretion may be mediated by MAP kinases such as the p38 MAP kinase as discussed above. Examples of inflammatory diseases or conditions believed to be mediated by the p38 MAP kinase are selected from the group consisting of asthma, arthritis, including rheumatoid arthritis and spondyloarthritis, gout, atherosclerosis, inflammatory bowel diease, Crohn's disease, neurological inflammations, inflammatory eye diseases, proliferative and inflammatory skin disorders, such as psoriasis, atopic dermatitis and acne vulgaris, uveitis, sepsis, septic shock and osteoporosis.

The treatment may additionally involve administration of one or more other anti-inflammatory active components such as glucocorticoids, vitamin D and vitamin D analogues, antihistamines, platelet activating factor (PAF) antagonists, anticholinergic agents, methylxanthines, β-adrenergic agents, COX-2 inhibitors, salicylates, indomethacin, flufenamate, naproxen, timegadine, gold salts, penicillamine, serum cholesterol lowering agents, retinoids, zinc salts and salicylazosulfapyridine. The administration of a compound of the present invention and another anti-inflammatory component may be either concomitantly or sequentially.

Ophthalmic diseases or conditions contemplated for treatment with the present compounds include the ophthalmic disease or condition is non-infectious (e.g. allergic) conjunctivitis, iritis, keratitis, uveitis, scleritis, episcleritis, sympathetic ophthalmitis, blepharitis or keratoconjunctivitis sicca.

Pharmacological Methods

To study the effect of compounds of the present invention in vitro, the inhibition of IL-1β and TNF-α secretion was determined using the following procedure:

Cytokine production was measured in the media from lipopolysaccharide (LPS) stimulated peripheral blood mononuclear cells. The mononuclear cells were isolated from human peripheral blood by Lymphoprep® (Nycomed, Norway) fractionation and suspended in RPMI 1640 (growth medium) with foetal calf serum (FCS, 2%), at a concentration of $5 \times 10^5$ cells/ml. The cells were incubated in 24-well tissue culture plates in 1 ml aliquots. Test compounds were dissolved in dimethylsulfoxide (DMSO, 10 mM) and were diluted with the medium. Compounds were added to the cells for 30 minutes, then LPS (1 mg/ml final concentration) was added. The plates were incubated for 18 hours, and the concentration of IL-1β and TNF-α in the medium was determined by enzyme-linked immunosorbent assays. The median inhibitory concentrations ($IC_{50}$) of the compounds were calculated. The results are shown in Table 1.

TABLE 1

Inhibition of cytokines production in vitro by compounds of the present invention.

| Compound No. | The median inhibition concentration ($IC_{50}$, nM) of | |
| --- | --- | --- |
| | IL-1β | TNF-α |
| Compound 102 | 1.3 | 0.5 |
| Compound 104 | 0.6 | 0.5 |
| Compound 105 | | 1.4 |
| Compound 106 | 0.7 | 0.5 |
| Compound 107 | 0.8 | 0.5 |
| Compound 108 | 1.3 | 0.7 |
| Compound 109 | 1.9 | 1.2 |
| Compound 110 | 6.3 | 3.6 |
| Compound 112 | 5.0 | 0.3 |
| Compound 113 | 6.3 | 0.6 |
| Compound 114 | 0.4 | 0.3 |
| Compound 115 | 0.5 | 0.5 |
| Compound 117 | 1.6 | 1.1 |
| Compound 118 | 1.3 | 0.9 |
| Compound 120 | 5.0 | 0.8 |
| Compound 122 | 1.4 | 0.9 |
| Compound 124 | 0.8 | 0.5 |
| Compound 125 | 1.0 | 0.5 |
| Compound 127 | 0.9 | 0.7 |
| Compound 128 | | 1.0 |
| Compound 129 | | 1.4 |
| Compound 130 | 1.3 | 0.6 |
| Compound 131 | 2.5 | 1.8 |
| Compound 136 | 1.6 | 1.3 |
| Compound 137 | 1.0 | 0.3 |
| Compound 138 | 3.2 | 2.0 |
| Compound 139 | 1.6 | 0.5 |
| Compound 140 | 2.0 | 0.8 |
| Compound 141 | 0.6 | 0.6 |
| Compound 142 | 1.0 | 0.8 |
| Compound 143 | 4.0 | 1.0 |
| Compound 145 | 5.0 | 2.0 |

TABLE 1-continued

Inhibition of cytokines production in vitro by compounds of the present invention.

| Compound No. | The median inhibition concentration ($IC_{50}$, nM) of | |
| --- | --- | --- |
| | IL-1β | TNF-α |
| Ref. comp. a | 13 | 7.1 |
| Ref. comp. b | 6.3 | 6.3 |
| Ref. comp. c | 32 | 6.3 |
| Ref. comp. d | 7.9 | 3.2 |
| Ref. comp. e | 6.3 | 3.2 |
| Ref. comp. f | 13 | 4.0 |

Ref. comp. a: (4-(2-aminophenylamino)-2-chloro-2'-methylbenzophenone, Compound 156 disclosed in WO 98/32730.
Ref. comp. b: 2'-[3-Chloro-4-(2-methylbenzoyl)phenylamino]octananilide, Compound 102 disclosed in WO 01/05746.
Ref. comp. c: 1-Acetoxymethyl N-[2-[3-chloro-4-(2-methylbenzoyl)phenylamino]phenyl] carbamate, Compound 109 disclosed in WO 01/05749.
Ref. comp. d: 1-Ethyl-3-[2-[3-chloro-4-(2-methylbenzoyl)phenylamino]-5-fluoro-phenyl] urea, Compound 114 disclosed in WO 01/05751.
Ref. comp. e: 2,2,2-Trifluoro-N-[2-[3-chloro-4-(2-methylbenzoyl)phenylamino]-5-fluorophenyl]acetamide, Compound 102 disclosed in WO 01/05745.
Ref. comp. f: 2-Chloro-4-(3-fluoro-2-methyl-phenylamino)-2'-methylbenzophenone, Compound 131 disclosed in WO 01/42189.

These results show that compounds of the present invention are highly potent inhibitors of the production of IL-1β, TNF-α and show a surprisingly higher cytokine inhibitory activity than the reference compounds, thus making them potentially useful in the treatment of inflammatory diseases.

Furthermore, the novel aminobenzophenone derivatives may have surprisingly favourable pharmacokinetic properties such as absorption and metabolic stability.

p38α MAP Kinase Assay

Cell Culture

COS-1 cells (derived from African green monkey kidney fibroblast-like cell containing wild-type T antigen under control of the SV40 promotor) were obtained from ATCC (ATCC no. CRL-1650) and grown in growth medium (DMEM without phenolred, 10% FCS, 2 mM L-glutamine, 100U penicillin and 100 µg streptomycin/ml) at 37° C. with 5% $CO_2$. The cells were passaged twice a week by trypsination (0.25% trypsin, 1 mM EDTA in PBS) and were split 1:10. The medium was changed every second or third day. The cell line was regularly tested with the Mycoplasma PCR Primer Set (Stratagene) and found to be free of Mycoplasma. Tissue culture media, FCS, L-glutamine and penicillin and streptomycin are from Bribco BRL, Gaithersburg, Md., USA.

Transient Expression of COS-1 Cells

On day one COS-1 cells were seeded in 143 cm² petridish with a density of $2 \times 10^4$ celler/cm² in growth medium. At day 2 the cells were co-transfected with 5 µg (total) of experimental plasmid DNA, expressing the FLAG-p38α and FLAG-MKK6(EE). The plasmids were introduced into the COS-1 cells in serum-free medium using DOTAP™ (Boehringer-Mannheim, Mannheim, Germany). Plasmid DNA was prepared and purified using the QIAGEN EndoToxin-free Maxiprep-500 kit (Hilden, Germany). Briefly, DNA and DOTAP™ were mixed for exactly 15 min. at 37° C. in the $CO_2$ incubator. The transfection-mixture was hereafter transferred to a 15-ml falcon-tube and transfection-medium (DMEM with L-Glutamine and Pen./Strep. but without serum) was added to the transfection-mixture, followed by addition to the cell-monolayer. After 4 hours of incubation with DOTAP™ and plasmids, the medium containing double amount of serum was added to the cells bringing the final concentration of serum up to 10%. The cells were then incubated for 24 hours before kinase reaction.

Immunoprecipitation

After 24 hrs of incubation the reaction was stopped by putting the petri dish on an ice-bath. The medium was aspirated, and the cell monolayer was washed once in ice-cold PBS (137 mM NaCl, 1.5 mM $KH_2PO_4$, 2.7 mM KCl, 8.1 mM $Na_2HPO_4.2H_2O$), and hereafter solubilised for 10 min. in 1.5 ml lysis buffer (50 mM HEPES, pH 7.5, 150 mM NaCl, 10 mM EDTA, 10 mM $Na_4P_2O_7$, 100 mM NaF, 2 mM $Na_3VO_4$, 1% Triton-X-100, Pefabloc 500 µM, Leupeptin 10 µg/µl, Aprotinin 10 µg/µl) was added. The cell-monolayer was scraped by a rubber-policeman, and transferred to an Eppendorf tube. The solubilised cells were clarified by centrifugation at 10.000×g for 10 min. at 4° C. The supernatant was transferred to 50 µl prewashed Protein G Sepharose beads in HNT-buffer (30 mM HEPES, pH 7.5, 30 mM NaCl, 0.1% Triton X-100) and were incubated with 2 µg/sample of monoclonal anti-FLAG™ M2 antibody (raised against the FLAG-epitope, $NH_2$-Asp-Tyr-Lys-Asp-Asp-Asp-Asp-Lys-COOH) for 1 hour at room temperature. The anti-FLAG M2 monoclonal antibody was obtained from Sigma (cat. no. F-3165). Approx. 60 µg protein of clarified cell lysate were added to the preadsorbed anti-FLAG™ antibodies on Protein G Sepharose beads and incubated for 90 min. at 4° C. in a blood sample mixer. After the immunoprecipitation period the Sepharose beads were washed twice in lysis buffer and twice in a kinase reaction buffer (25 mM HEPES pH 7.5, 10 mM magnesium acetate, 50 µM ATP).

Incubation of the Compounds with Purified p38α Kinase

The pre-washed immunoprecipitated anti-FLAG-p38 adsorbed on Protein G Sepharose beads was washed twice in 1× kinase-buffer (25 mM HEPES pH 7.5, 10 mM magnesium acetate, 50 µM ATP), and the supernatant was aspirated. The compounds were diluted in 1× kinase buffer at the appropriate concentration. The compounds were added to the washed immunoprecipitated and activated FLAG-p38 adsorbed on the Protein G Sepharose beads for 30 min. at 30° C. in a volume of 100 µl. Every 10 min. the Eppendorf tubes were tapped to ensure that the beads and the compounds were in the solution. After 30 min. incubation, the beads were spun down and the supernatant was aspirated.

p38α MAP Kinase Reaction

The kinase reaction was started by adding 1 µg GST-ATF-2 substrate (Santa Cruz, LaJolla, Calif., USA, cat. no. sc-4114) together with 2 µCiγ-$^{32}$P-ATP in 1× kinase-buffer per sample. The reaction was allowed to proceed for 30 min. at 30° C., and it was stopped by adding 40 µl of 2×SDS-sample buffer to the kinase reaction. The samples were boiled, spinned down, and resolved on a 15% SDS-PAGE. The dried SDS-PAGE gel was exposed to a Phospho-Imager screen and the radioactive PHAS-1 bands were quantified by the STORM860 Phospho-Imager (Molecular Dynamics, Sunnyvale, Calif., USA) using the ImageQuaNT software.

In this assay, Compound 102 was found to be a potent p38 MAP kinase inhibitor.

In Vivo Screening Model of LPS Induced TNF-α Response in Mice

To study the effect of compounds of the present invention in vivo, an in vivo screening model of LPS induced TNF-α response in mice was set up as follows: Groups of 6 mice (C3H/HeN, female, about 8 weeks (20 g), Bomholtgaard) were dosed with test compounds in suspension vehicle 1 hour prior to LPS administration (LPS from *E. coli* 055:B5, L-4005, Sigma). At time 0, the mice were dosed ip with 1.0 mg LPS/kg. After anesthetization with Hypnorm/Dormicum, the mice were bled from the periorbital venous plexus 80-90 minutes after LPS administration. The blood samples were sampled in EDTA stabilised tubes and centrifuged at 4000 rpm for 10 minutes at 4° C. The plasma level of TNF-α was analysed by ELISA. Compound 156 of WO 98/32730 was used as reference compound. The plasma level of TNF-α was determined using a sandwich ELISA. Microtiter plates were coated with a monoclonal antibody against mouse TNF-α, washed and blocked with a casein buffer. Samples of mouse TNF-α recombinant standards were added to the wells of the microtiter plates and incubated. All standards were tested in triplicate, all plasma samples in single. After sample and standard incubation, the plates were washed and incubated with biotinylated polyclonal secondary antibody against mouse TNF-α and washed. Enzyme conjugate was added to all wells and incubated. Substrate was added and the enzyme/substrate reaction stopped after 15 minutes at room temperature with 1M $H_2SO_4$. The colour development (OD) was measured at 450 nm on an ELISA reader and the background OD at 620 nm was subtracted. Experiments were approved if the group treated with the reference compound showed a significant inhibition ($p<0.05$) of the TNF-α response compared to the LPS treated control group. The results of the tested compounds are indicated as a percentage inhibition compared to an LPS treated control group. Compounds were tested at 1 mg/kg (p.o.). The Mann-Whitney test was used to compare drug treated groups to the LPS treated control group ($p<0.05$). The results are shown in Table 3.

TABLE 3

In vivo inhibition of LPS induced TNF-α production (in %)

| Compound No. | |
|---|---|
| Compound 102 | 94 |
| Compound 104 | 90 |
| Compound 106 | 98 |
| Compound 107 | 91 |
| Compound 108 | 78 |
| Compound 109 | 79 |
| Compound 112 | 49 |
| Compound 114 | 86 |
| Compound 115 | 70 |
| Compound 122 | 96 |
| Compound 124 | 77 |
| Compound 125 | 96 |
| Compound 127 | 94 |
| Compound 128 | 95 |
| Compound 129 | 83 |
| Compound 131 | 80 |
| Ref. comp. a | 23 |

Ref. comp. a: (4-(2-aminophenylamino)-2-chloro-2'-methylbenzophenone, Compound 156 disclosed in WO 98/32730 (tested at 10 mg/kg i.p.).

The results show that compounds of the present invention surprisingly show an improved biological activity in vivo with respect to inhibition of LPS induced TNF-α production in mice compared to the reference compound, thus making them potentially useful in the treatment of inflammatory diseases.

The invention is described in further detail in the following non-liting examples which are not in any way intended to limit the scope of the invention as claimed.

EXAMPLES

General

All melting points are uncorrected. For $^1$H nuclear magnetic resonance (NMR) spectra (300 MHz) and $^{13}$C NMR (75.6 MHz) chemical shift values (δ) (in ppm) are quoted, unless otherwise specified; for deuteriochloroform solutions relative to internal tetramethylsilane (δ=0.00) or chloroform ($\delta$=7.26) or deuteriochloroform ($\delta$=76.81 for $^{13}$C NMR) standard. The value of a multiplet, either defined (doublet (d), triplet (t), quartet (q)) or not (m) at the approximate mid point is given unless a range is quoted. All organic solvents used were anhydrous. Chromatography was performed on silica gel using the flash technique. Appropriate mixtures of ethyl acetate, dichloromethane, methanol, and petroleum ether (40-60) were used as eluents unless otherwise noted.

The following abbreviations have been used:

| | |
|---|---|
| aq. | aqueous |
| dba | Dibenzylideneacetone |
| DCM | Dichloromethane |
| DMAP | 4-Dimethylaminopyridine |
| DMF | N,N-Dimethylformamide |
| DIEA | Ethyl diisopropyl amine |
| EDCI | 1-(3-dimethylaminopropyl)-3-ethylcarbodiimide |
| | hydrochloride |
| EtOAc | Ethyl acetate |
| FDPP | Diphenyl-phosphinic acid pentafluorophenyl ester |
| h | Hour(s) |
| HATU | O-(7-Azabenzotriazol-1-yl)-N,N,N',N'-tetramethyluronium-hexafluorophosphate |
| min | Minutes |
| NMP | N-methylmorpholine |
| NMR | Nuclear magnetic resonance |
| rac-BINAP | Racemic 2,2'-bis(diphenylphosphino)-1,1'-binaphtyl |
| RT | Room temperature |
| TBAF | Tetra-n-butylammonium fluoride |
| TEA | Triethylamine |
| TFA | Trifluoroacetic acid |
| THF | Tetrahydrofuran |
| THP | Tetrahydropyran |
| TIPSCl | Triisopropylsilyl chloride |
| v | Volume |

TABLE 4

Exemplified compounds of general formula I

| Compound | Example no. | Structure |
|---|---|---|
| 101 | 1 | 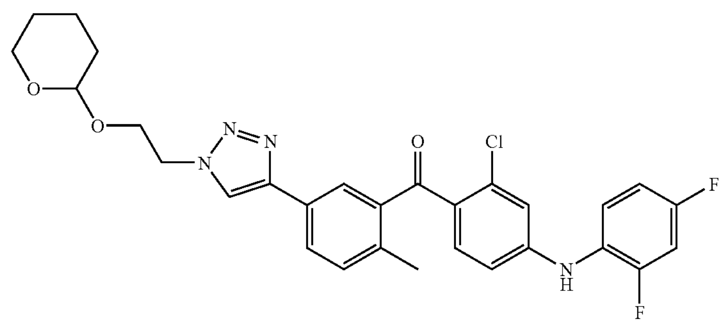 |
| 102 | 2 | 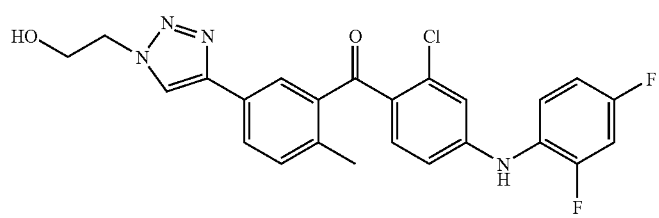 |
| 103 | 3 | 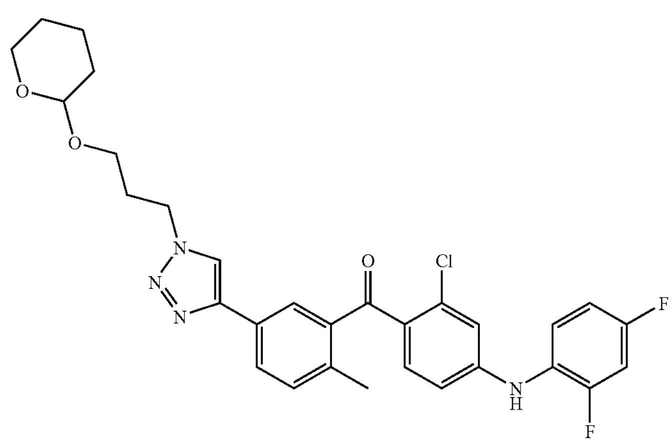 |

TABLE 4-continued

Exemplified compounds of general formula I

| Compound | Example no. | Structure |
|---|---|---|
| 104 | 4 | 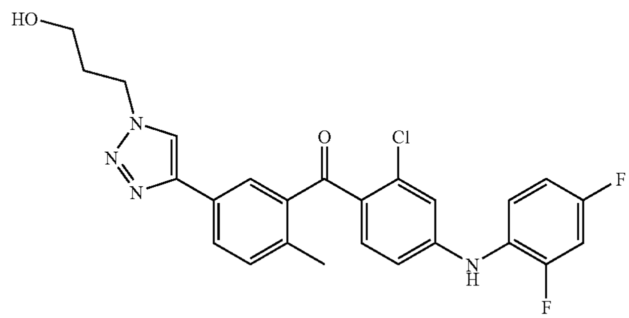 |
| 105 | 5 | 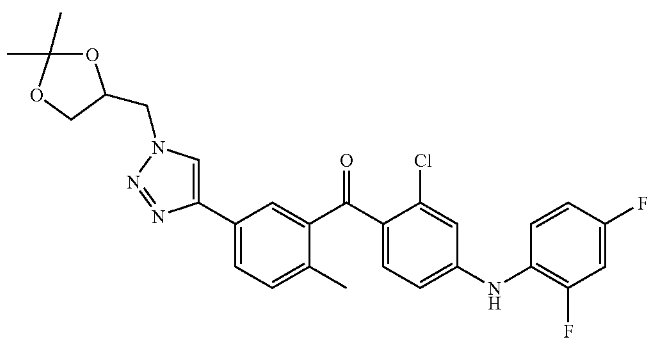 |
| 106 | 6 | 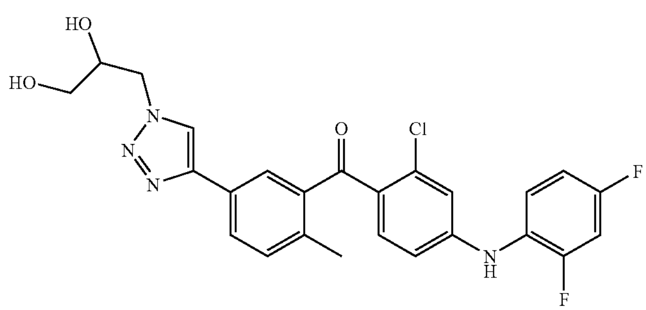 |
| 107 | 7 | 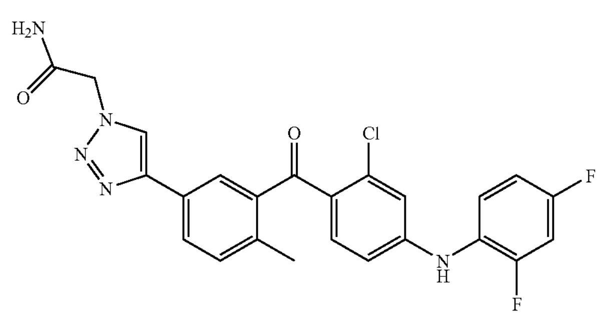 |

TABLE 4-continued
Exemplified compounds of general formula I
| Compound | Example no. | Structure |
|---|---|---|
| 108 | 8 | 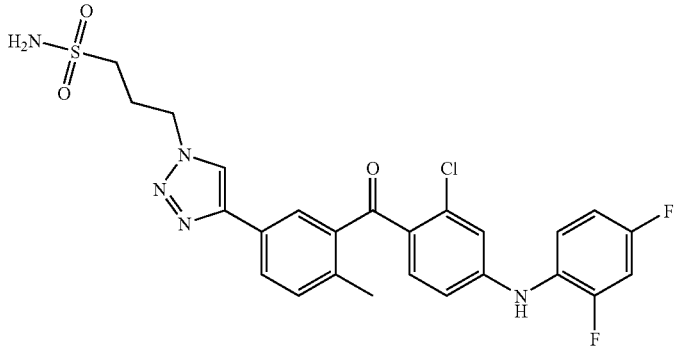 |
| 109 | 9 | 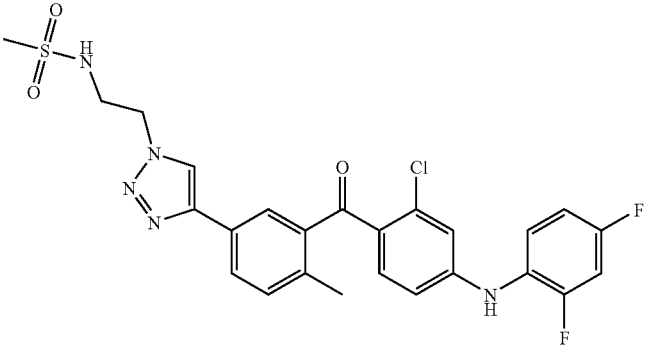 |
| 110 | 10 | 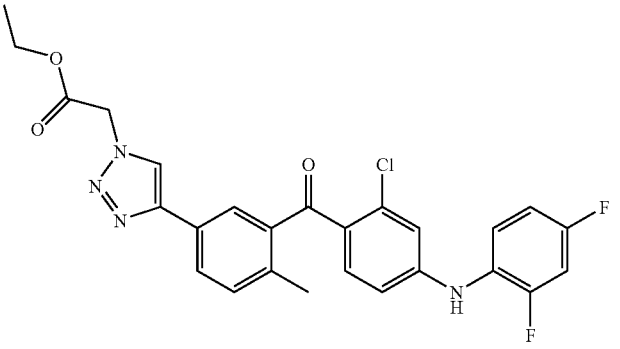 |
| 111 | 11 | 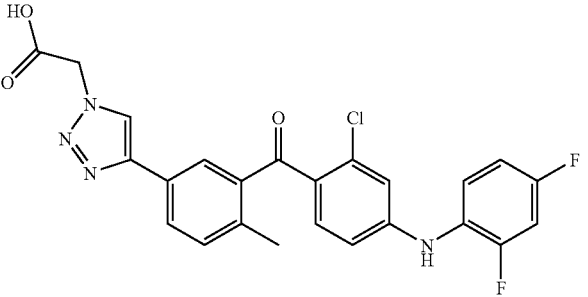 |

TABLE 4-continued

Exemplified compounds of general formula I

| Compound | Example no. | Structure |
|---|---|---|
| 112 | 12 | 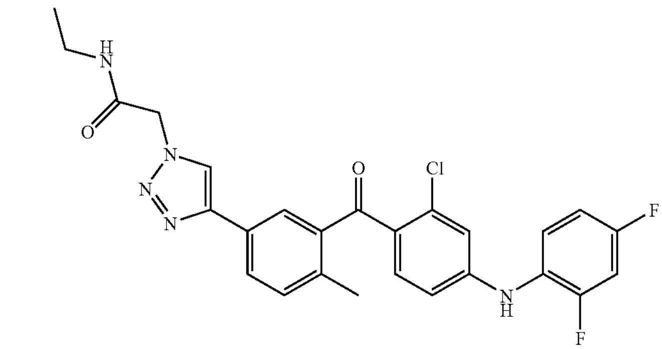 |
| 113 | 13 | 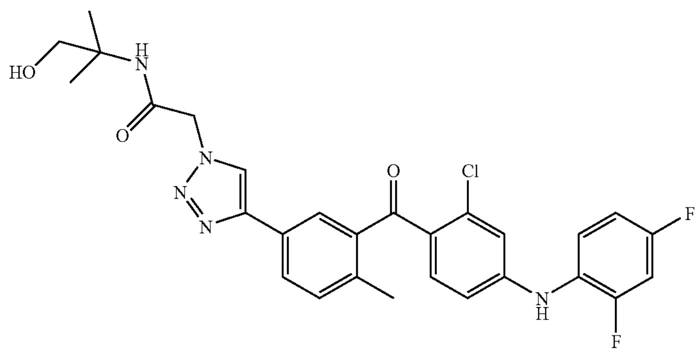 |
| 114 | 14 | 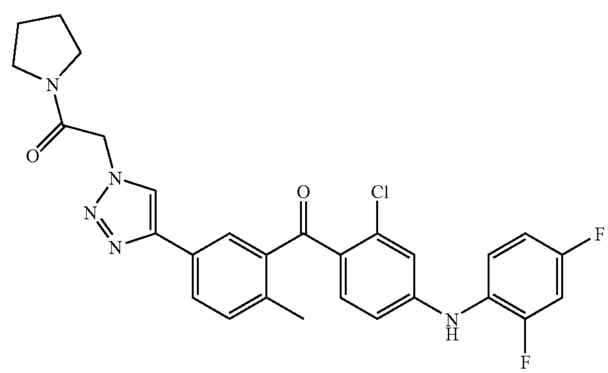 |
| 115 | 15 | 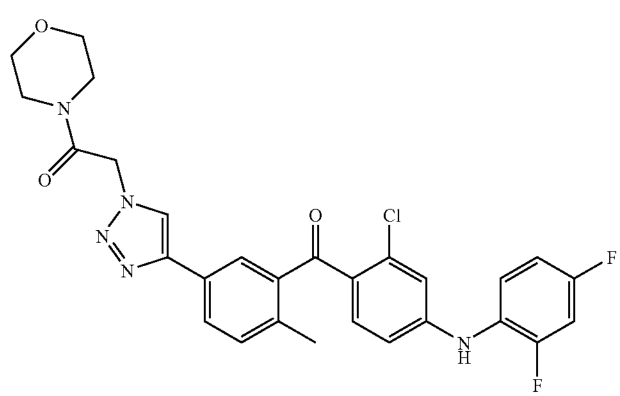 |

TABLE 4-continued

Exemplified compounds of general formula I

| Compound | Example no. | Structure |
|---|---|---|
| 116 | 16 | 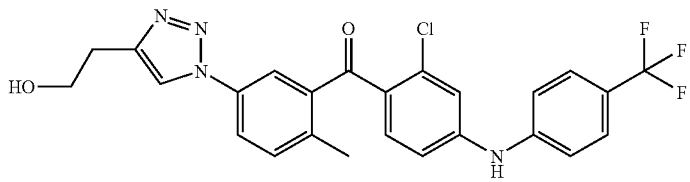 |
| 117 | 17 | 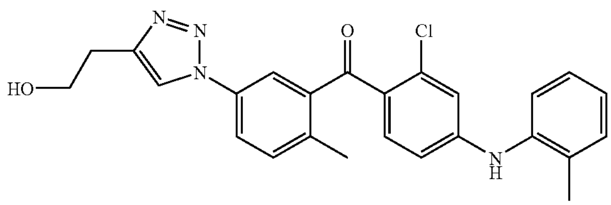 |
| 118 | 18 | 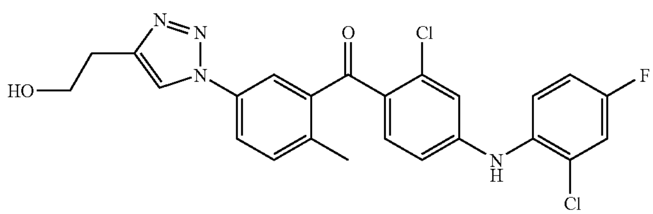 |
| 119 | 19 | 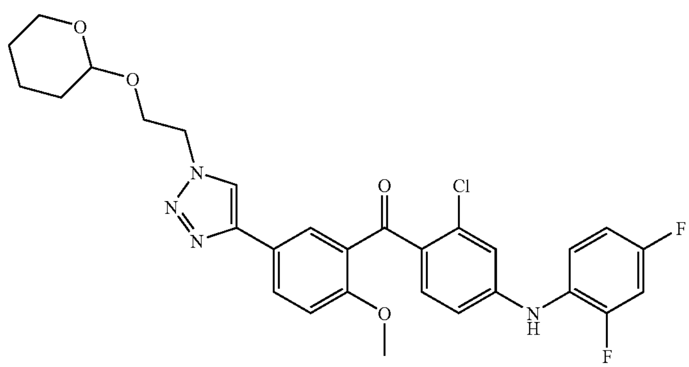 |
| 120 | 20 | 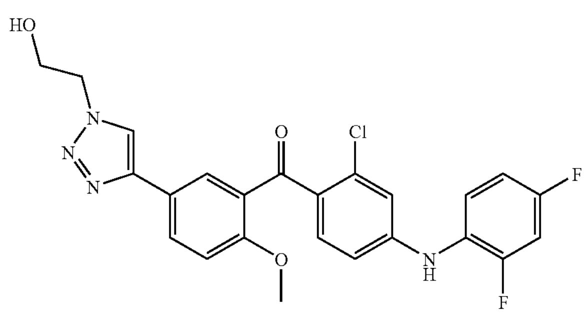 |

TABLE 4-continued

Exemplified compounds of general formula I

| Compound | Example no. | Structure |
|---|---|---|
| 121 | 21 | 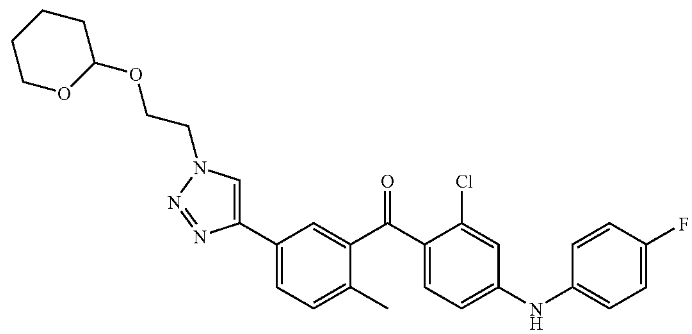 |
| 122 | 22 | 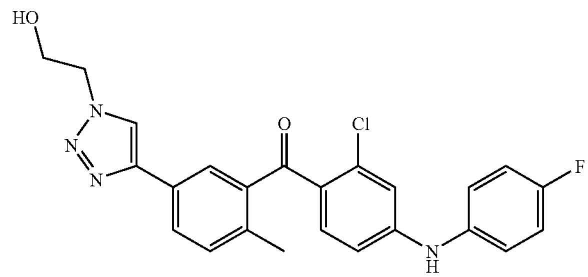 |
| 123 | 23 | 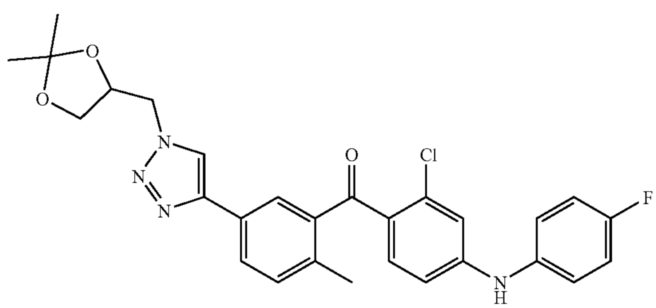 |
| 124 | 24 | 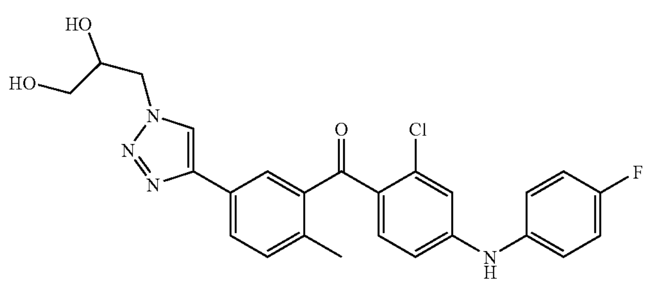 |
| 125 | 25 | 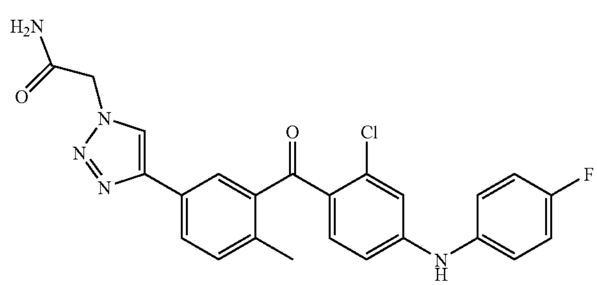 |

TABLE 4-continued

Exemplified compounds of general formula I

| Compound | Example no. | Structure |
|---|---|---|
| 126 | 26 | 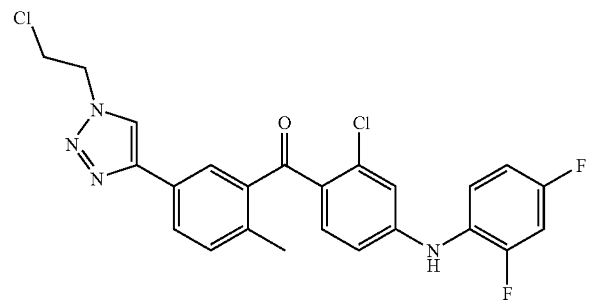 |
| 127 | 27 | 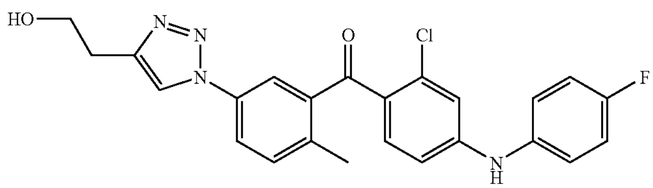 |
| 128 | 28 | 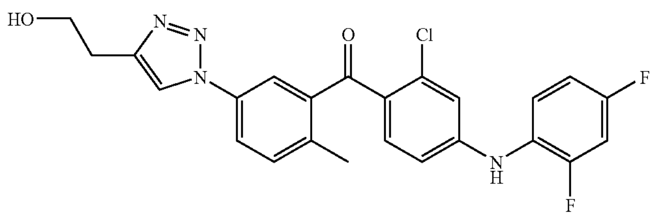 |
| 129 | 29 | 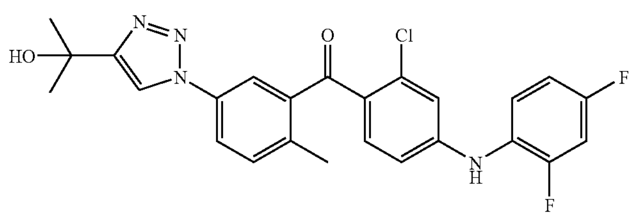 |
| 130 | 30 | 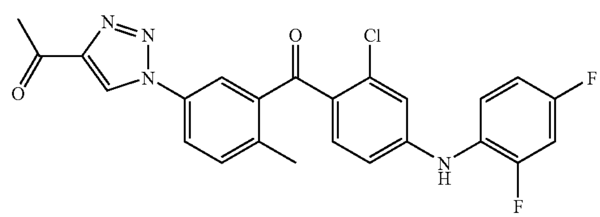 |
| 131 | 31 | 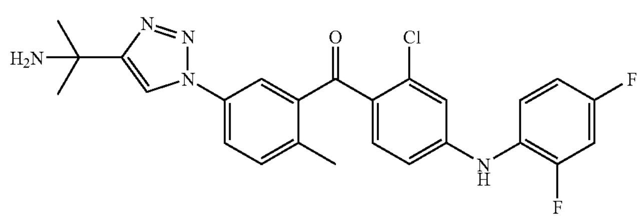 |

TABLE 4-continued

Exemplified compounds of general formula I

| Compound | Example no. | Structure |
|---|---|---|
| 132 | 32 | 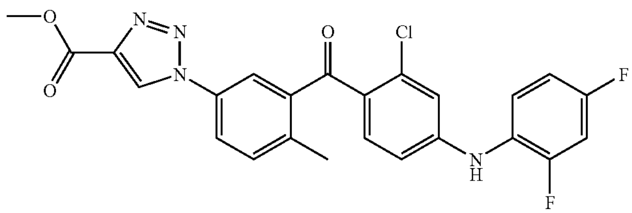 |
| 133 | 33 | 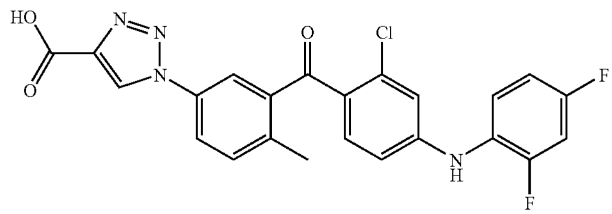 |
| 134 | 34 | 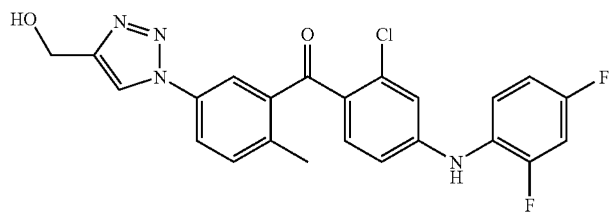 |
| 135 | 35 | 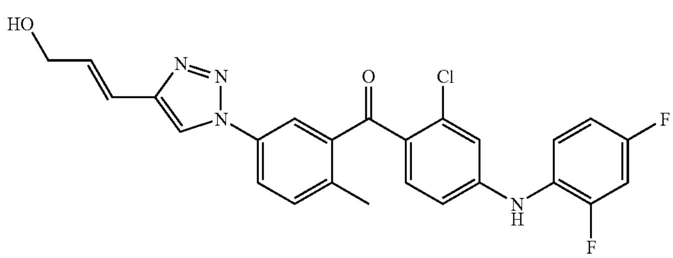 |
| 136 | 36 | 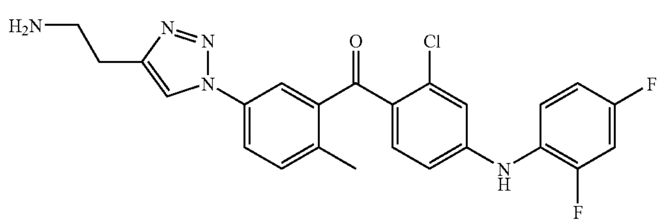 |
| 137 | 37 | 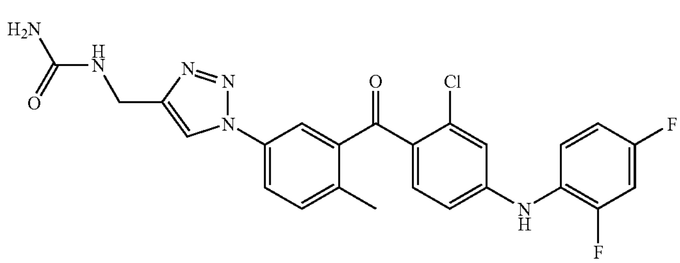 |

TABLE 4-continued

Exemplified compounds of general formula I

| Compound | Example no. | Structure |
|---|---|---|
| 138 | 38 | 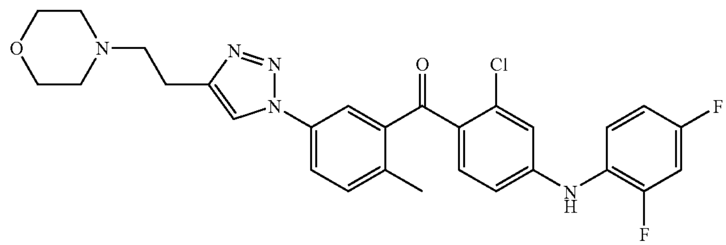 |
| 139 | 39 | 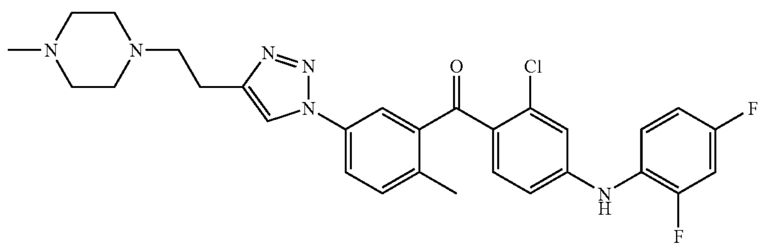 |
| 140 | 40 | 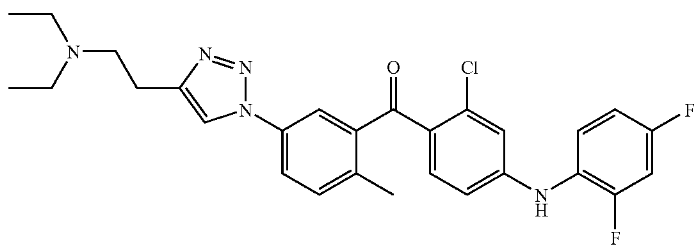 |
| 141 | 41 | 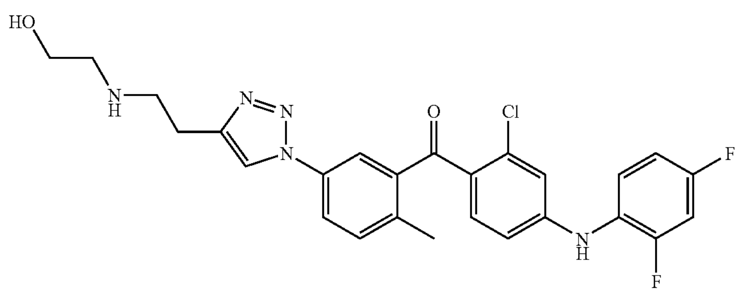 |
| 142 | 42 | 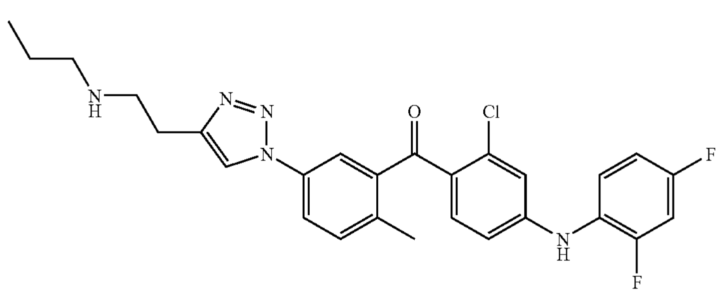 |
| 143 | 43 | 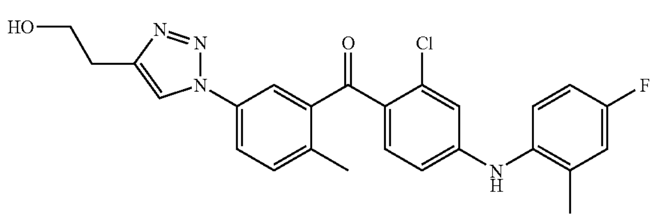 |

TABLE 4-continued

Exemplified compounds of general formula I

| Compound | Example no. | Structure |
|---|---|---|
| 144 | 44 | 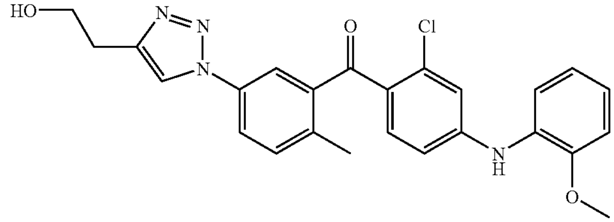 |
| 145 | 45 | 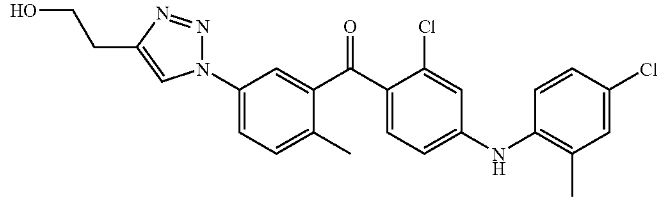 |
| 146 | 46 | 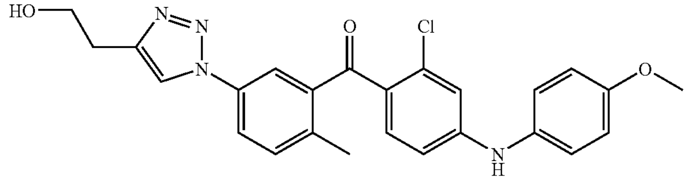 |
| 147 | 47 | 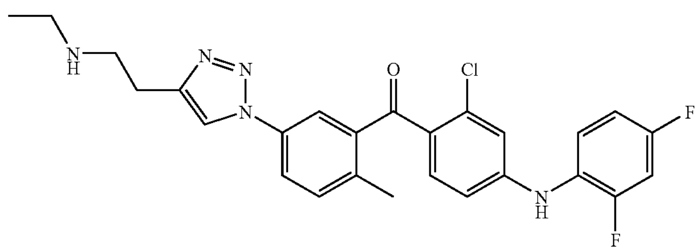 |
| 148 | 48 | 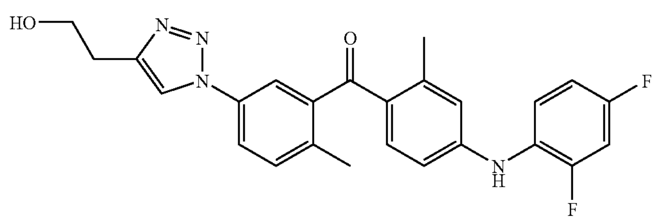 |
| 149 | 49 | 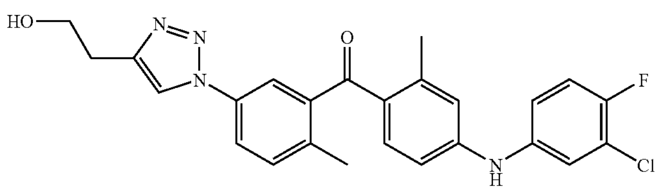 |
| 150 | 50 | 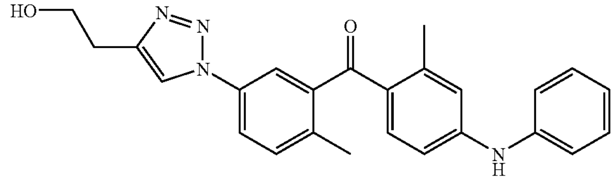 |

TABLE 4-continued

Exemplified compounds of general formula I

| Compound | Example no. | Structure |
|---|---|---|
| 151 | 51 | 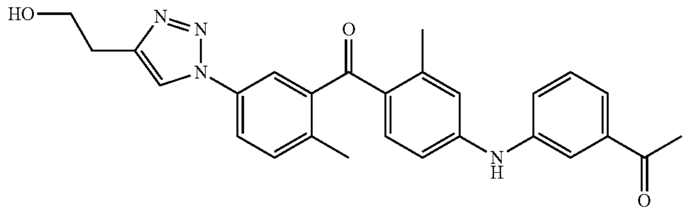 |
| 152 | 52 | 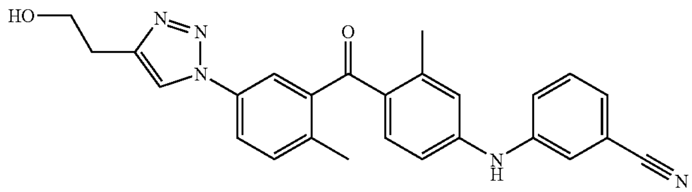 |
| 153 | 53 | 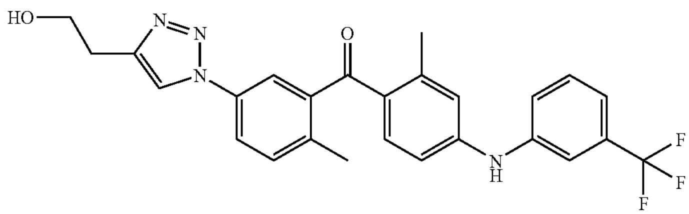 |
| 154 | 54 | 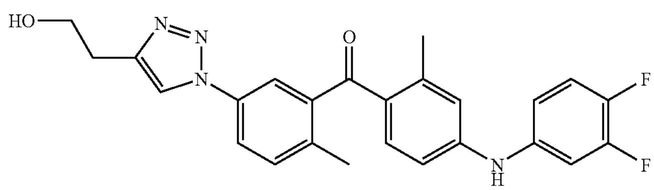 |
| 155 | 55 | 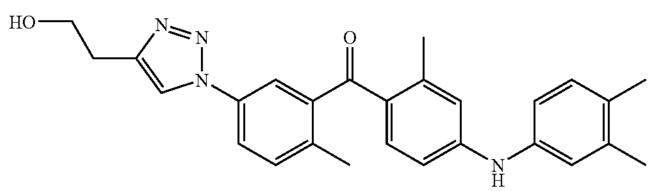 |
| 156 | 56 | 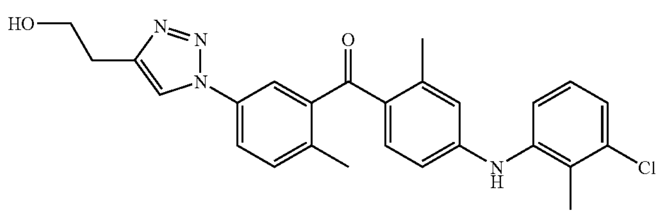 |
| 157 | 57 | 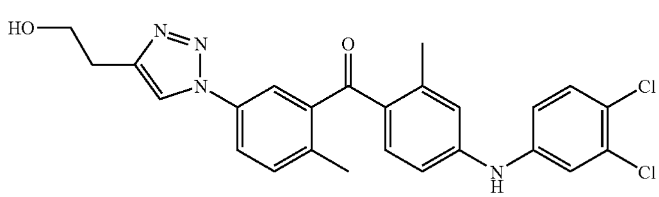 |

TABLE 4-continued

Exemplified compounds of general formula I

| Compound | Example no. | Structure |
|---|---|---|
| 158 | 58 | 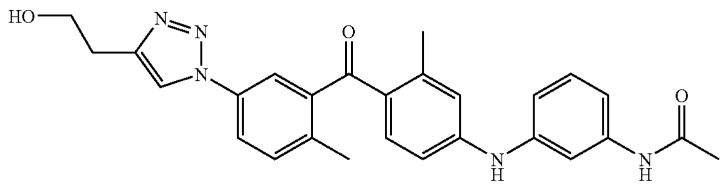 |
| 159 | 59 | 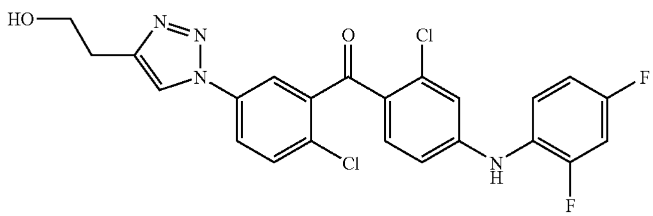 |
| 160 | 60 | 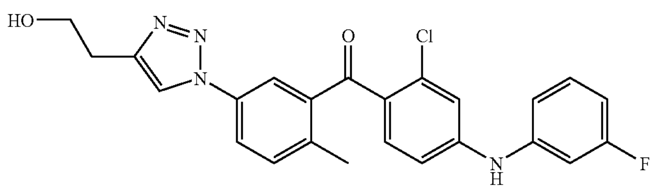 |
| 161 | 61 | 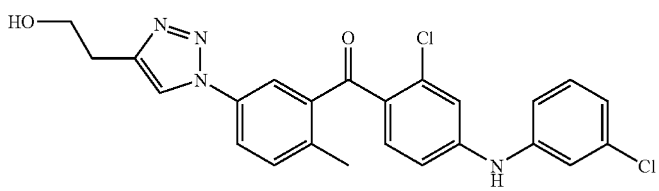 |
| 162 | 62 | 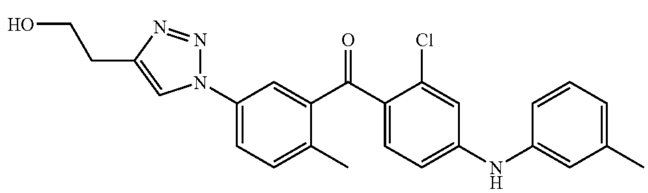 |
| 163 | 63 | 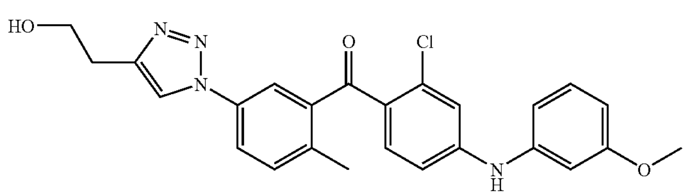 |
| 164 | 64 | 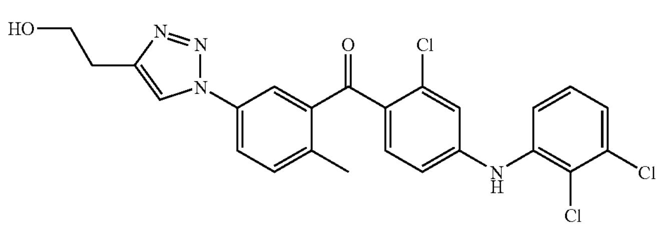 |

TABLE 4-continued

Exemplified compounds of general formula I

| Compound | Example no. | Structure |
|---|---|---|
| 165 | 65 | *(structure: HO-ethyl-triazole-N-phenyl-C(=O)-chlorophenyl-NH-dimethylphenyl, with methyl on central phenyl)* |
| 166 | 66 | *(structure: HO-ethyl-triazole-N-phenyl-C(=O)-chlorophenyl-NH-(2,5-difluorophenyl), with methyl on central phenyl)* |
| 167 | 67 | *(structure: HO-ethyl-triazole-N-phenyl-C(=O)-chlorophenyl-NH-(3,5-difluorophenyl), with methyl on central phenyl)* |

Preparation 1

2-Methyl-5-nitro-thiobenzoic acid S-pyridin-2-yl ester (compound 401)

2-Methyl-5-nitrobenzoic acid (22.5 g, 124 mmol), 2,2'-dithiopyridine (27.5 g, 124 mmol) and triphenylphosphine (32.6 g, 124 mmol) were dissolved in $CH_3CN$ (650 mL). The solution was stirred at room temperature for 18 h. The reaction mixture was filtered and the solid was washed with small amounts of $CH_3CN$. This afforded the title compound as a colourless solid.

Preparation 2

(4-Bromo-2-chloro-phenyl)-(2-methyl-5-nitro-phenyl)-methanone (compound 402)

The reaction was run under an argon atmosphere using dry glassware. 4-Bromo-2-chloroiodobenzene (25.5 g, 80.9 mmol) was dissolved in dry THF (400 mL) and cooled to $-60°$ C. Isopropylmagnesium chloride (2 M in THF, 40.4 mL, 80.9 mmol) was added under stirring during 30 minutes. The reaction mixture was allowed to warm up to $-40°$ C. and the mixture was stirred at $-40°$ C. for 4 h. Compound 401 (22.2 g, 80.9 mmol) was added and the mixture was stirred at $-40°$ C. for 3 h after which it was allowed to warm to room temperature and stirred for 17 h. A saturated aqueous solution of $NH_4Cl$ (200 mL) was added and the mixture was stirred for 1 h. The phases were separated and the aqueous phase was extracted with $Et_2O$ (4×100 mL). The combined organic phases were washed with brine, dried ($MgSO_4$), filtered and concentrated in vacuo. The crude product was purified by flash chromatography using $CH_2Cl_2$/petroleum ether (40-60) 2:3 as the eluent to afford the title compound as yellow crystalline compound.

Preparation 3

[2-Chloro-4-(2,4-difluoro-phenylamino)-phenyl]-(2-methyl-5-nitro-phenyl)-methanone (compound 403)

Compound 402 (5.4 g, 15.2 mmol) was dissolved in dry 1,4-dioxan (150 mL) in a 200 mL screw cap vessel. 2,4-Difluoroaniline (1.7 mL, 16.7 mmol) was added and argon was blown over the mixture. $Cs_2CO_3$ (14.9 g, 45.7 mmol), BINAP (0.38 g, 0.6 mmol) and $Pd(OAc)_2$ (0.14 g, 0.6 mmol) were added and argon was blown through the mixture and the screw cap vessel was closed. The mixture was stirred at $100°$ C. for 7 h. The reaction mixture was poured into $H_2O$ (100 mL) and EtOAc (200 mL). The water phase was extracted with EtOAc (×3) and the combined organic phases were washed with brine, dried ($MgSO_4$), filtered and concentrated in vacuo. The crude product was purified by flash chromatography using $CH_2Cl_2$/petroleum ether (40-60) 2:3->1:1->1:0 followed by EtOAc as the eluent to afford the title compound as a yellow crystalline compound.

Preparation 4

(5-Amino-2-methyl-phenyl)-[2-chloro-4-(2,4-difluoro-phenylamino)-phenyl]-methanone (compound 404)

Compound 403 (6.0 g, 14.9 mmol) was dissolved in MeOH (350 mL). Zinc-dust (12.69 g, 194 mmol) and $NH_4Cl$ (5.59 g, 104 mmol) were added. The reaction mixture was heated at reflux temperature for 1 h. The mixture was filtered and washed with MeOH. The filtrate was concentrated and the solid was dissolved in EtOAc (150 mL) and saturated aqueous $Na_2CO_3$ (100 mL). The water phase was extracted with EtOAc and the combined organic phases were dried ($MgSO_4$), filtered and concentrated in vacuo. The crude product was purified by flash chromatography using EtOAc/petroleum ether (40-60) 1:2 as the eluent to afford the title compound as a slightly coloured crystalline compound.

Preparation 5

[2-Chloro-4-(2,4-difluoro-phenylamino)-phenyl]-(5-iodo-2-methyl-phenyl)-methanone (compound 405)

Compound 404 (0.62 g, 1.66 mmol) was dissolved in acetone (14 mL). Concentrated HCl (37%, 0.69 mL, 8.3 mmol) was added and the solution was cooled on an icebath. NaNO$_2$ (0.14 g, 1.99 mmol) was dissolved in H$_2$O (1 mL) and added to the above solution during 15 minutes. The internal temperature was kept at 0° C.-2° C. during the addition. The suspension was stirred on an ice bath for 0.5 h, after which a solution of KI (0.41 g, 2.45 mmol) and I$_2$ (0.31 g, 1.22 mmol) in H$_2$O (4 mL) was added drop wise during 5 minutes. The mixture was stirred at 0° C. for 2 h. H$_2$O (20 mL) and EtOAc (20 mL) was added and stirred and the phases were separated. The organic phase was washed with aqueous NaHSO$_3$, then with aqueous Na$_2$CO$_3$, dried (MgSO$_4$), filtered and concentrated in vacuo. The crude product was purified by flash chromatography using EtOAc/petroleum ether (40-60) 1:5 to afford the title compound as a slightly coloured crystalline compound.

Preparation 6

[2-Chloro-4-(2,4-difluoro-phenylamino)-phenyl]-(2-methyl-5-trimethylsilanylethynyl-phenyl)-methanone (compound 406)

Compound 405 (400 mg, 0.83 mmol) and ethynyltrimethylsilane (115 µL, 0.83 mmol), were dissolved in degassed triethylamine (11 mL). Triphenylphosphine (21.7 mg, 0.083 mmol), pd$_2$(dba)$_3$ (15 mg, 0.017 mmol) and copper(I)iodide (3 mg, 0.017 mmol) were then added to the solution. The flask was closed, filled with argon and then stirred at 90° C. for 18 h. The reaction mixture was filtered through Decalite and concentrated in vacuo. The crude product was purified by continuous gradient flash chromatography using EtOAc/petroleum ether (40-60) 0:100 to 25:75 as the eluent to afford the title compound as syrup.

Preparation 7

[2-Chloro-4-(2,4-difluoro-phenylamino)-phenyl]-(5-ethynyl-2-methyl-phenyl)-methanone (compound 407)

A solution of compound 406 (426 mg, 0.94 mmol) and K$_2$CO$_3$ (195 mg, 1.41 mmol) in methanol (4.0 mL) were stirred at RT for 5 h. The reaction mixture was poured into a mixture of EtOAc/water. The organic phase was washed with water, brine and then dried (MgSO$_4$), filtered and concentrated in vacuo to give the crude title compound. The product was used without any further purification.

2-(2-Azido-ethoxy)-tetrahydro-pyran (compound 408)

A mixture of 2-(2-bromo-ethoxy)-tetrahydro-pyran (1.00 mL, 6.62 mmol), NaN$_3$ (4.34 g, 66 mmol) and tetrabutylammonium iodide (245 mg, 0.66 mmol) in DMF (7.0 mL) was stirred at RT for 18 h. The reaction mixture was poured into a mixture of EtOAc/water. The organic phase was washed with water, brine and then dried (MgSO$_4$), filtered and concentrated in vacuo to give the crude product. The crude product was purified by continuous gradient flash chromatography using EtOAc/petroleum ether (40-60) 0:100 to 20:80 as the eluent to afford the title compound as colourless oil.

Example 1

[2-Chloro-4-(2,4-difluoro-phenylamino)-phenyl]-(2-methyl-5-{1-[2-(tetrahydro-pyran-2-yloxy)-ethyl]-1H-[1,2,3]triazol-4-yl}-phenyl)-methanone (compound 101)

Compound 407 (300 mg, 0.79 mmol) and compound 408 (135 mg, 0.79 mmol) were dissolved in ethanol (6.0 mL). A freshly prepared solution of copper(II) sulphate pentahydrate (7.8 mg, 0.031 mmol) and sodium ascorbate (31 mg, 0.16 mmol) in water (0.9 mL) was added to the reaction mixture. The flask was closed and stirred for 48 h at RT. The reaction mixture was poured into a mixture of EtOAc/water. The organic phase was washed with water, brine and then dried (MgSO$_4$), filtered and concentrated in vacuo to give the crude product. The crude product was purified by continuous gradient flash chromatography using EtOAc/petroleum ether (40-60) 0:100 to 50:50 as the eluent to afford the title compound as light brown syrup.

$^{13}$C NMR (CDCl$_3$) δ 196.1, 159.1 (dd), 155.5 (dd), 147.8, 146.9, 139.8, 137.7, 135.3, 133.7, 131.9, 129.4, 128.3, 127.9, 126.5, 124.4 (dd), 124.3 (dd), 120.8, 116.3, 112.8, 111.6 (dd), 104.9 (dd), 99.1, 65.8, 62.4, 50.5, 30.4, 25.2, 20.2, 19.4

Example 2

[2-Chloro-4-(2,4-difluoro-phenylamino)-phenyl]-{5-[1-(2-hydroxy-ethyl)-1H-[1,2,3]triazol-4-yl]-2-methyl-phenyl}-methanone (compound 102)

A solution of compound 101 (350 mg, 0.63 mmol) in methanol (4.0 mL) was added toluene-4-sulfonic acid (60 mg, 0.32 mmol) and the mixture was stirred for 7 h at RT. The reaction mixture was poured into a mixture of EtOAc/water. The organic phase was washed with NaOH (aq., 2 M), water, brine and then dried (MgSO$_4$), filtered and concentrated in vacuo to give the crude product. The crude product was purified by flash chromatography using EtOAc/petroleum ether (40-60) 25:75 as the eluent to afford the title compound as yellow foam.

$^{13}$C NMR (CDCl$_3$) δ 196.2, 159.2 (dd), 155.6 (dd), 148.1, 146.7, 139.9, 137.6, 135.2, 133.8, 131.8, 128.9, 127.8, 126.2, 124.6 (dd), 124.3 (dd), 121.1, 116.2, 112.7, 111.6 (dd), 104.9 (dd), 61.1, 52.8, 20.1

Preparation 9

2-(3-Azido-propoxy)-tetrahydro-pyran (compound 409)

A mixture of 2-(3-chloro-propoxy)-tetrahydro-pyran (6.28 g, 35.2 mmol), NaN$_3$ (11.4 g, 176 mmol) and potassium iodide (584 mg, 3.52 mmol) in DMF (50 mL) was stirred at RT for 18 h. The reaction mixture was poured into a mixture of Et$_2$O/water. The organic phase was washed with water, brine and then dried (MgSO$_4$), filtered and concentrated in vacuo to give the crude product. The crude product was purified by continuous gradient flash chromatography using EtOAc/petroleum ether (40-60) 0:100 to 15:85 as the eluent to afford the title compound as colourless oil.

Example 3

[2-Chloro-4-(2,4-difluoro-phenylamino)-phenyl]-(2-methyl-5-{1-[3-(tetrahydro-pyran-2-yloxy)-propyl]-1H-[1,2,3]triazol-4-yl}-phenyl)-methanone (compound 103)

The reaction was carried out similarly as described in the preparation of compound 101, using compound 407 (0.44 mmol) and compound 409 (0.44 mmol). The crude product was purified by continuous gradient flash chromatography using EtOAc/petroleum ether (40-60) 10:90 to 50:50 as the eluent to afford the title compound as colourless foam.
$^{13}$C NMR (CDCl$_3$) δ 196.1, 147.8, 146.9, 139.8, 137.6, 135.3, 133.7, 131.9, 129.4, 128.2, 127.9, 126.4, 124.4 (dd), 124.3 (dd), 120.2, 116.3, 112.8, 111.6 (dd), 104.9 (dd), 99.4, 63.8, 62.9, 47.5, 30.7, 30.5, 25.4, 20.2, 19.9

Example 4

[2-Chloro-4-(2,4-difluoro-phenylamino)-phenyl]-{5-[1-(3-hydroxy-propyl)-1H-[1,2,3]triazol-4-yl]-2-methyl-phenyl}-methanone (compound 104)

The reaction was carried out similarly as described in the preparation of compound 102, using compound 103 (0.2 mmol). The crude product was purified by continuous gradient flash chromatography using EtOAc/petroleum ether (40-60) 50:50 to 100:0 as the eluent to afford the title compound as colourless foam. $^{13}$C NMR (CDCl$_3$) δ 196.1, 159.2 (dd), 155.6 (dd), 148.0, 146.9, 139.9, 137.7, 135.3, 133.8, 131.9, 129.1, 128.0, 127.9, 126.4, 124.5 (dd), 124.3 (dd), 120.3, 116.3, 112.8, 111.6 (dd), 104.9 (dd), 58.8, 47.0, 32.6, 20.2

Preparation 10

4-Azidomethyl-2,2-dimethyl-[1,3]dioxolane (compound 410)

The reaction was carried out similarly as described in the preparation of compound 408, using toluene-4-sulfonic acid 2,2-dimethyl-[1,3]dioxolan-4-ylmethyl ester (37.8 mmol). The crude product was purified by continuous gradient flash chromatography using EtOAc/petroleum ether (40-60) 0:100 to 20:80 as the eluent to afford the title compound as colourless foam.

Example 5

[2-Chloro-4-(2,4-difluoro-phenylamino)-phenyl]-{5-[1-(2,2-dimethyl-[1,3]dioxolan-4-ylmethyl)-1H-[1,2,3]triazol-4-yl]-2-methyl-phenyl}-methanone (compound 105)

The reaction was carried out similarly as described in the preparation of compound 101, using compound 407 (1.37 mmol) and compound 410 (1.62 mmol). The crude product was purified by continuous gradient flash chromatography using EtOAc/petroleum ether (40-60) 20:80 to 35:65 as the eluent to afford the title compound as yellow foam. $^{13}$C NMR (DMSO-d$_6$) δ 194.9, 158.7 (dd), 155.7 (dd), 149.4, 145.2, 139.8, 135.9, 133.7, 133.7, 131.7, 128.2, 127.1, 126.5, 126.5 (dd), 125.0, 124.2 (dd), 122.3, 114.8, 111.9 (dd), 111.8, 109.0, 105.0 (dd), 73.7, 65.8, 52.0, 26.4, 25.1, 19.4

Example 6

[2-Chloro-4-(2,4-difluoro-phenylamino)-phenyl]-{5-[1-(2,3-dihydroxy-propyl)-1H-[1,2,3]triazol-4-yl]-2-methyl-phenyl}-methanone (compound 106)

A solution of compound 105 (535 mg, 1.16 mmol) in THF (6.0 mL) was added aqueous HCl (1M, 6 mL)) and the mixture was stirred for 24 h at RT. The reaction mixture was poured into a mixture of EtOAc/saturated NaHCO$_3$. The aqueous phase was washed with more EtOAc. The collected organic phases were washed with water, brine and then dried (MgSO$_4$), filtered and concentrated in vacuo to give the crude product. The crude product was purified by continuous gradient flash chromatography using MeOH/DCM 2:98 to 10:90 as the eluent to afford the title compound as yellow foam. $^{13}$C NMR (DMSO-d$_6$) δ 194.9, 158.7 (dd), 155.7 (dd), 149.3, 145.0, 139.8, 135.7, 133.7, 133.7, 131.6, 128.4, 127.1, 126.6, 126.5 (dd), 124.9, 124.2 (dd), 122.3, 114.8, 112.0 (dd), 111.8, 105.0 (dd), 70.3, 63.2, 53.0, 19.4

Preparation 11

2-Azido-acetamide (compound 411)

A mixture of 2-chloro-acetamide (2.00 g, 21.4 mmol), NaN$_3$ (6.95 g, 107 mmol) and tetrabutylammonium iodide (790 mg, 2.14 mmol) in DMF (30.0 mL) was stirred at 50° C. for 48 h. The reaction mixture was poured into a mixture of EtOAc/water. The organic phase was washed with water, brine and then dried (MgSO$_4$), filtered and concentrated in vacuo to give the crude product. The crude product was used without any further purification. The crude product contained substantial amount of DMF (aprox. 6 eq.).

Example 7

2-(4-{3-[2-Chloro-4-(2,4-difluoro-phenylamino)-benzoyl]-4-methyl-phenyl}-[1,2,3]triazol-1-yl)-acetamide (compound 107)

The reaction was carried out similarly as described in the preparation of compound 101, using compound 407 (0.44 mmol) and compound 411. The crude product was purified by continuous gradient flash chromatography using MeOH/DCM 0:100 to 10:90 as the eluent to afford the title compound as yellow solid. $^{13}$C NMR (DMSO-d$_6$) δ 194.9, 167.1, 158.7 (dd), 155.7 (dd), 149.3, 145.2, 139.8, 135.9, 133.7, 133.7, 131.7, 128.2, 127.1, 126.6, 126.4 (dd), 125.0, 124.2 (dd), 123.0, 114.9, 112.0 (dd), 111.8, 105.0 (dd), 51.5, 19.4

Preparation 12

3-Azido-propane-1-sulfonic acid amide (compound 412)

The reaction was carried out similarly as described in the preparation of compound 411, using compound 3-chloro-propane-1-sulfonic acid amide (19.0 mmol). The crude product was purified by continuous gradient flash chromatography using EtOAc/petroleum ether (40-60) 35:65 to 65:35 as the eluent to afford the title compound as colourless oil.

Example 8

3-(4-{3-[2-Chloro-4-(2,4-difluoro-phenylamino)-benzoyl]-4-methyl-phenyl}-[1,2,3]triazol-1-yl)-propane-1-sulfonic acid amide (compound 108)

The reaction was carried out similarly as described in the preparation of compound 101, using compound 407 (1.37 mmol) and compound 412 (2.79 mmol). The crude product was purified by continuous gradient flash chromatography using EtOAc/petroleum ether (40-60) 65:35 to 85:15 as the eluent to afford the title compound as almost white solid. $^{13}$C NMR (DMSO-d$_6$) δ 194.9, 158.8 (dd), 155.7 (dd), 149.4, 145.5, 139.9, 135.9, 133.7, 133.7, 131.7, 128.2, 127.1, 126.5, 126.4 (dd), 124.9, 124.1 (dd), 121.6, 114.8, 111.9 (dd), 111.8, 105.0 (dd), 51.4, 47.9, 24.6, 19.4

Preparation 13

N-(2-Azido-ethyl)-methanesulfonamide (compound 413)

Into a 100 mL flask was placed 2-chloroethylamine hydrochloride (5.0 g, 43.1 mmol) and dichloromethane (50 mL). To the suspension was added N-methylmorpholine (10 mL, 91 mmol) while maintaining the temperature between −3 and 5° C. Methane-sulfonyl chloride (4.0 mL, 51.7 mmol) was added slowly to the reaction mixture. After 2 h the reaction mixture was washed with water, 4 N HCl, and water. The organic layer was dried over Na$_2$SO$_4$, filtered and concentrated in vacuo. The crude solfonamide (3.1 g) was redissolved in DMF (8.0 mL). NaI (327 mg, 1.97 mmol) and NaN$_3$ (1.92 g, 29.5 mmol) was added to the solution. The reaction mixture was stirred for 48 h at 50° C. and then poured into a mixture of EtOAc/water. The organic phase was washed with water, brine and then dried (MgSO$_4$), filtered and concentrated in vacuo to give the crude product. The crude product was used without any further purification.

Example 9

N-[2-(4-{3-[2-Chloro-4-(2,4-difluoro-phenylamino)-benzoyl]-4-methyl-phenyl}-[1,2,3]triazol-1-yl)-ethyl]-methanesulfonamide (compound 109)

The reaction was carried out similarly as described in the preparation of compound 101, using compound 407 (0.87 mmol) and compound 413 (1.3 mmol). The crude product was purified by continuous gradient flash chromatography using EtOAc/petroleum ether (40-60) 65:35 to 85:15 as the eluent to afford the title compound as almost white solid. $^{13}$C NMR (DMSO-d$_6$) δ 194.9, 158.7 (dd), 155.7 (dd), 149.4, 145.3, 139.8, 135.9, 133.7, 133.7, 131.7, 128.2, 127.1, 126.5, 126.4 (dd), 124.9, 124.1 (dd), 121.9, 114.8, 111.9 (dd), 111.8, 105.0 (dd), 49.8, 42.2, 39.5, 19.4

Example 10

(4-{3-[2-Chloro-4-(2,4-difluoro-phenylamino)-benzoyl]-4-methyl-phenyl}-[1,2,3]triazol-1-yl)-acetic acid ethyl ester (compound 110)

Compound 407 (243 mg, 0.64 mmol) and a solution of azido-acetic acid ethyl ester (0, 0.7 mmol) in toluene (0.60 mL) were dissolved in acetone (3.5 mL). A freshly prepared solution of copper(II) sulphate pentahydrate (7.0 mg, 0.026 mmol) and sodium ascorbate (25 mg, 0.13 mmol) in water (0.5 mL) was added to the reaction mixture. The flask was closed and stirred for 24 h at RT under argon.

The reaction mixture was poured into a mixture of EtOAc/water. The organic phase was washed with water, brine and then dried (MgSO$_4$), filtered and concentrated in vacuo to give the crude product. The crude product was purified by continuous gradient flash chromatography using EtOAc/petroleum ether (40-60) 5:95 to 60:40 as the eluent to afford the title compound as light yellow foam. $^{13}$C NMR (CDCl$_3$) δ 196.0, 166.3, 159.1 (dd), 155.5 (dd), 147.8, 147.5, 139.9, 137.9, 135.3, 133.7, 131.9, 129.3, 128.0, 127.9, 126.6, 124.4 (dd), 124.3 (dd), 121.0, 116.4, 112.9, 111.6 (dd), 104.9 (dd), 62.5, 51.0, 20.2, 14.1

Example 11

(4-{3-[2-Chloro-4-(2,4-difluoro-phenylamino)-benzoyl]-4-methyl-phenyl}-[1,2,3]triazol-1-yl)-acetic acid (compound 111)

A solution of compound 110 (236 mg, 0.46 mmol) in MeOH (3.0 mL) was added LiOH (55 mg, 2.31 mmol) and water (0.3 mL). The reaction mixture was stirred for 2 h under reflux. The reaction mixture was poured into a mixture of EtOAc/saturated NaCl. Aq. HCl (1 N, 0.5 mL) was added. The aqueous phase was washed with more EtOAc. The collected organic phases were washed with water, brine and then dried (MgSO$_4$), filtered and concentrated in vacuo to give the crude product. The crude product was purified by flash chromatography using a mixture of MeOH/DCM/acetic acid 400:2:1 as the eluent to afford the title compound as yellow foam. $^{13}$C NMR (DMSO-d$_6$) δ 194.9, 168.4, 158.7 (dd), 155.7 (dd), 149.3, 145.3, 139.8, 136.0, 133.7, 133.7, 131.7, 128.1, 127.1, 126.5, 126.4 (dd), 125.0, 124.2 (dd), 122.8, 114.8, 112.0 (dd), 111.8, 105.0 (dd), 50.9, 19.4

Example 12

2-(4-{3-[2-Chloro-4-(2,4-difluoro-phenylamino)-benzoyl]-4-methyl-phenyl}-[1,2,3]triazol-1-yl)-N-ethyl-acetamide (compound 112)

To a solution of compound 111 (39 mg, 0.08 mmol) in DMF (1.0 mL) was added ethylamine hydrochloride (20 mg, 0.08 mmol), FDPP (43 mg, 0.11 mmol), and DIEA (68 µL, 0.4 mmol). The flask was flushed with argon and the reaction mixture was stirred at RT for 72 h and then poured into a mixture of water (4 mL), HCl (4N, 2 mL), and EtOAc. The phases were separated. The organic phase was concentrated on silica in vacuo. The crude product was purified by chromatography eluting with EtOAc/petroleum ether (40-60) 50:50 to 100:0 as the eluent to afford the title compound as white foam. $^{13}$C NMR (DMSO-d$_6$) δ 194.9, 164.8, 149.3, 145.2, 139.8, 135.9, 133.7, 133.7, 131.7, 128.2, 127.1, 126.6, 126.4 (dd), 125.0, 124.2 (dd), 123.0, 114.8, 111.9 (dd), 111.8, 105.0 (dd), 51.7, 33.6, 19.4, 14.4

Example 13

2-(4-{3-[2-Chloro-4-(2,4-difluoro-phenylamino)-benzoyl]-4-methyl-phenyl}-[1,2,3]triazol-1-yl)-N-(2-hydroxy-1,1-dimethyl-ethyl)-acetamide (compound 113)

The reaction was carried out similarly as described in the preparation of compound 112, using compound 111 (0.08 mmol) and 2-amino-2-methyl-1-propanol (0.08 mmol). The crude product was purified by continuous gradient flash chromatography using EtOAc/petroleum ether (40-60) 50:50 to 100:0 as the eluent to afford the title compound as almost yellow solid. $^{13}$C NMR (DMSOd$_6$) δ 8.74 (s, 1H), 8.50 (s, 1H), 7.90 (dd, 1H), 7.85 (bs, 1H), 7.75 (d, 1H), 7.50-7.33 (m, 4H), 7.11 (m, 1H), 6.83 (m, 1H), 6.78 (m, 1H), 5.07 (s, 2H), 4.80 (t, 1H), 3.40 (d, 2H), 2.33 (s, 3H), 1.21 (s, 6H)

Example 14

2-(4-{3-[2-Chloro-4-(2,4-difluoro-phenylamino)-benzoyl]-4-methyl-phenyl}-[1,2,3]triazol-1-yl)-1-pyrrolidin-1-yl-ethanone (compound 114)

The reaction was carried out similarly as described in the preparation of compound 112, using compound 111 (0.12 mmol) and pyrolidine (0.12 mmol). The crude product was purified by continuous gradient flash chromatography using MeOH/EtOAc 0:100 to 5:95 as the eluent to afford the title compound as almost yellow syrup.
$^{13}$C NMR (CDCl$_3$) δ 196.0, 163.1, 159.0 (dd), 155.4 (dd), 147.8, 147.1, 139.7, 137.9, 135.2, 133.7, 131.9, 129.3, 128.0, 127.8, 126.6, 124.5 (dd), 124.2 (dd), 121.5, 116.4, 112.9, 111.5 (dd), 104.9 (dd), 51.9, 46.4, 46.4, 26.1, 24.1, 20.2

Example 15

2-(4-{3-[2-Chloro-4-(2,4-difluoro-phenylamino)-benzoyl]-4-methyl-phenyl}-[1,2,3]triazol-1-yl)-1-morpholin-4-yl-ethanone (compound 115)

The reaction was carried out similarly as described in the preparation of compound 112, using compound 111 (0.12 mmol) and morpholine hydrochloride (0.12 mmol). The crude product was purified by continuous gradient flash chromatography using MeOH/EtOAc 0:100 to 5:95 as the eluent to afford the title compound as almost yellow syrup. $^{13}$C NMR (CDCl$_3$) δ 196.0, 163.5, 147.9, 147.3, 139.8, 138.0, 135.3, 133.7, 131.9, 129.2, 128.0, 127.7, 126.5, 124.4 (dd), 124.2 (dd), 121.4, 116.3, 112.8, 111.6 (dd), 104.9 (dd), 66.6, 66.4, 50.9, 45.9, 42.6, 20.2

Preparation 14

[2-Chloro-4-(4-trifluoromethyl-phenylamino)-phenyl]-(2-methyl-5-nitro-phenyl)-methanone (compound 414)

Compound 402 (100 mg, 0.28 mmol) was dissolved in dry 1,4-dioxan (2 mL) in a 8 mL screw cap vial. 4-Trifluoromethyl-phenylamine (35 μL, 0.28 mmol), Cs$_2$CO$_3$ (276 mg, 0.85 mmol), BINAP (7 mg, 0.011 mmol) and Pd(OAc)$_2$ (3 mg, 0.011 mmol) were added and argon was blown through the mixture and the screw cap vessel was closed. The mixture was stirred at 100° C. for 18 h. The reaction mixture was filtered through Decalite and concentrated on silica gel. The crude product was purified by continuous gradient flash chromatography using EtOAc/petroleum ether (40-60) 0:100 to 25:75 as the eluent to afford the title compound as yellow foam.

Preparation 15

(5-Amino-2-methyl-phenyl)-[2-chloro-4-(4-trifluoromethyl-phenylamino)-phenyl]-methanone (compound 415)

Compound 414 (134 mg, 0.31 mmol) was dissolved in MeOH (4 mL). Zinc-dust (203 mg, 3.1 mmol) and NH$_4$Cl (84 mg, 1.57 mmol) were added. The reaction mixture was heated at reflux temperature for 3 h. The mixture was filtered through Decalite and washed with MeOH. The filtrate was concentrated in vacuo to afford the title compound as foam.

Preparation 16

(5-Azido-2-methyl-phenyl)-[2-chloro-4-(4-trifluoromethyl-phenylamino)-phenyl]-methanone (compound 416)

Compound 415 (110 mg, 0.27 mmol) was dissolved in acetone (2 mL). Concentrated HCl (37%, 0.113 mL, 1.36 mmol) was added and the solution was cooled on an icebath. NaNO$_2$ (22 mg, 0.32 mmol) was dissolved in H$_2$O (0.18 mL) and added to the above solution during 5 minutes. The internal temperature was kept at 0° C.-2° C. during the addition. The suspension was stirred on an ice bath for 1 h, after which a solution of NaN$_3$ (27 mg, 0.41 mmol) in H$_2$O (0.56 mL) was added dropwise during 5 minutes. The mixture was stirred at 0° C. for 4 h. H$_2$O (5 mL) and EtOAc (10 mL) was added and stirred and the phases were separated. The organic phase was concentrated in vacuo to give the title compound. The crude product was used without any further purification.

Example 16

[2-Chloro-4-(4-trifluoromethyl-phenylamino)-phenyl]-{5-[4-(2-hydroxy-ethyl-[1,2,3]triazol-1-yl]-2-methyl-phenyl}-methanone (compound 116)

But-3-yn-1-ol (23 μL, 0.30 mmol) and compound 416 (116 mg, 0.27 mmol) were dissolved in acetone (2.6 mL) in a vial. A freshly prepared solution of copper(II) sulphate pentahydrate (7.0 mg, 0.028 mmol) and sodium ascorbate (27 mg, 0.14 mmol) in water (0.135 mL) was added to the reaction mixture. The vial was closed and stirred for 24 h at RT under argon. The reaction mixture was poured into a mixture of EtOAc/water. The organic phase was washed with water, brine, filtered and concentrated in vacuo to give the crude product. The crude product was purified by continuous gradient flash chromatography using EtOAc/petroleum ether (40-60) 20:80 to 0:100 as the eluent to afford the title compound as light yellow foam. $^{13}$C NMR (DMSO-d$_6$) δ 194.1, 147.1, 145.8, 144.6, 140.4, 136.5, 134.6, 134.0, 133.8, 132.6, 127.8, 126.7 (q), 121.7, 120.8, 119.4, 118.2, 117.3, 114.2, 60.2, 29.2, 19.3

Preparation 17

(2-Chloro-4-o-tolylamino-phenyl)-(2-methyl-5-nitro-phenyl)-methanone (compound 417)

The reaction was carried out similarly as described in the preparation of compound 414, using compound 402 (0.28 mmol) and 2-methyl aniline (0.28 mmol). The crude product was purified by continuous gradient flash chromatography using MeOH/EtOAc 0:100 to 25:75 as the eluent to afford the title compound as yellow foam.

Preparation 18

(5-Amino-2-methyl-phenyl)-(2-chloro-4-o-tolylamino-phenyl)-methanone (compound 418)

The reaction was carried out similarly as described in the preparation of compound 415, using compound 417 (0.39 mmol). The crude product was used without any further purification.

Preparation 19

(5-Azido-2-methyl-phenyl)-(2-chloro-4-o-tolylamino-phenyl)-methanone (compound 419)

The reaction was carried out similarly as described in the preparation of compound 416, using compound 418 (0.39 mmol). The crude product was used without any further purification.

Example 17

(2-Chloro-4-o-tolylamino-phenyl)-{5-[4-(2-hydroxyethyl)-[1,2,3]triazol-1-yl]-2-methyl-phenyl}-methanone (compound 117)

The reaction was carried out similarly as described in the preparation of compound 116, using compound 419 (0.40 mmol) and but-3-yn-1-ol (0.40 mmol). The crude product was purified by continuous gradient flash chromatography using EtOAc/petroleum ether (40-60) 20:80 to 0:100 as the eluent to afford the title compound as light yellow foam.
$^{13}$C NMR (CDCl$_3$) δ 194.7, 149.9, 146.2, 141.2, 138.0, 137.7, 135.7, 134.7, 134.2, 132.8, 132.5, 131.4, 127.1, 126.9, 125.8, 124.4, 122.1, 120.6, 120.0, 115.7, 112.3, 61.5, 28.7, 19.9, 17.9

Preparation 20

[2-Chloro-4-(2-chloro-4-fluoro-phenylamino)-phenyl]-(2-methyl-5-nitro-phenyl)-methanone (compound 420)

The reaction was carried out similarly as described in the preparation of compound 414, using compound 402 (0.28 mmol) and 2-chloro-4-fluoroaniline (0.28 mmol). The crude product was purified by continuous gradient flash chromatography using MeOH/EtOAc 0:100 to 25:75 as the eluent to afford the title compound as yellow foam.

Preparation 21

(5-Amino-2-methyl-phenyl)-[2-chloro-4-(2-chloro-4-fluoro-phenylamino)-phenyl]-methanone (compound 421)

The reaction was carried out similarly as described in the preparation of compound 415, using compound 420 (0.21 mmol). The crude product was used without any further purification.

Preparation 22

(5-Azido-2-methyl-phenyl)-[2-chloro-4-(2-chloro-4-fluoro-phenylamino)-phenyl]-methanone (compound 422)

The reaction was carried out similarly as described in the preparation of compound 416, using compound 421 (0.21 mmol). The crude product was used without any further purification.

Example 18

[2-Chloro-4-(2-chloro-4-fluoro-phenylamino)-phenyl]-{5-[4-(2-hydroxy-ethyl)-[1,2,3]triazol-1-yl]-2-methyl-phenyl}-methanone (compound 118)

The reaction was carried out similarly as described in the preparation of compound 116, using compound 422 (0.21 mmol) and but-3-yn-1-ol (0.21 mmol). The crude product was purified by continuous gradient flash chromatography using EtOAc/petroleum ether (40-60) 30:70 to 100:0 as the eluent to afford the title compound as light yellow foam.
$^{13}$C NMR (CDCl$_3$) δ 194.8, 158.7 (d), 147.9, 146.3, 140.7, 138.4, 135.4, 134.8, 133.8, 133.3 (d), 132.6, 128.8, 127.5 (d), 123.4 (d), 122.4, 120.9, 120.0, 117.6 (d), 116.9, 114.9 (d), 113.5, 61.5, 28.7, 20.0

Preparation 23

(5-Bromo-2-methoxy-phenyl)-(2-chloro-4-nitro-phenyl)-methanone (compound 423)

A mixture of 1-bromo-4-methoxy-benzene (7.48 g, 40 mmol), 2-chloro-4-nitro-benzoyl chloride (8.79 g, 40 mmol) and bismuth triflate (1.31 g, 2.0 mmol) under an atmosphere of argon was stirred at RT for 20 min. The temperature was raised to 80° C. and stirring was continued for 90 min. DCM was added to the reaction mixture and the organic phase was washed with aq. HCl (1 N, 0.5 mL) and NaHCO$_3$ (aq.). The organic phase was dried (MgSO$_4$), filtered and concentrated in vacuo to give the crude product. The crude product was crystallised from a mixture of DCM and pentane to afford the title compound as yellow crystals Preparation 24

(4-Amino-2-chloro-phenyl)-(5-bromo-2-methoxy-phenyl)-methanone (compound 424)

The reaction was carried out similarly as described in the preparation of compound 404, using compound 423 (16.1 mmol). The crude product was purified by continuous gradient flash chromatography using EtOAc/petroleum ether (40-60) 20:80 to 45:55 as the eluent to afford the title compound as yellow solid.

Preparation 25

(5-Bromo-2-methoxy-phenyl)-[2-chloro-4-(2,4-difluoro-phenylamino)-phenyl]-methanone (compound 425)

Compound 424 (4.39 g, 12.9 mmol) was suspended in dry toluene (100 mL) in a 200 mL screw cap vessel. 1-bromo-2,4-difluorobenzene (1.75 mL, 15.5 mmol) was added and argon was blown over the mixture. Cs$_2$CO$_3$ (5.88 g, 18.1 mmol), 4,5-bis-diphenylphosphanyl-9,9-dimethyl-9H-xanthene (0.22 g, 0.39 mmol) and Pd(OAc)$_2$ (58 mg, 0.26 mmol) were added and argon was blown through the mixture and the screw cap vessel was closed. The mixture was stirred at 120° C. for 72 h. The reaction mixture was filtered through decalite and then concentrated on silica gel in vacuo. The crude product was purified by continuous gradient flash chromatography using EtOAc/petroleum ether (40-60) 5:95 to 30:70 as the eluent to afford the title compound as yellow solid.

Preparation 26

[2-Chloro-4-(2,4-difluoro-phenylamino)-phenyl]-(2-methoxy-5-trimethylsilanylethynyl-phenyl)-methanone (compound 426)

The reaction was carried out similarly as described in the preparation of compound 406, using compound 425 (0.99 mmol) and ethynyltrimethylsilane (0.99 mmol). The crude product was purified by continuous gradient flash chromatography using EtOAc/petroleum ether (40-60) 0:100 to 10:90 as the eluent to afford the title compound as light orange syrup.

Preparation 27

[2-Chloro-4-(2,4-difluoro-phenylamino)-phenyl]-(5-ethynyl-2-methoxy-phenyl)-methanone (compound 427)

The reaction was carried out similarly as described in the preparation of compound 407, using compound 426 (0.44 mmol). The crude product was used directly in the next reaction without any further purification.

Example 19

[2-Chloro-4-(2,4-difluoro-phenylamino)-phenyl]-(2-methoxy-5-{1-[2-(tetrahydro-pyran-2-yloxy)-ethyl]-1H-[1,2,3]triazol-4-yl}-phenyl)-methanone (compound 119)

The reaction was carried out similarly as described in the preparation of compound 101, using compound 427 (0.42 mmol) and compound 408 (0.42 mmol). The crude product was purified by continuous gradient flash chromatography using EtOAc/petroleum ether (40-60) 20:80 to 60:40 as the eluent to afford the title compound as light orange foam.
$^{13}$C NMR (CDCl$_3$) δ 193.2, 159.0 (dd), 158.1, 155.4 (dd), 147.3, 146.9, 134.8, 133.3, 130.2, 127.7, 124.8 (dd), 123.9 (dd), 123.8, 120.3, 116.2, 113.0, 112.3, 111.5 (dd), 104.9 (dd), 99.2, 65.8, 62.5, 56.1, 50.6, 30.5, 25.3, 19.4

Example 20

[2-Chloro-4-(2,4-difluoro-phenylamino)-phenyl]-{5-[1-(2-hydroxy-ethyl)-1H-[1,2,3]triazol-4-yl]-2-methoxy-phenyl}-methanone (compound 120)

The reaction was carried out similarly as described in the preparation of compound 101, using compound 119 (0.11 mmol). The crude product was purified by continuous gradient flash chromatography using EtOAc/petroleum ether (40-60) 20:80 to 100:0 as the eluent to afford the title compound as yellow foam.
$^{13}$C NMR (CDCl$_3$) δ 193.3, 158.1, 147.4, 146.7, 134.8, 133.4, 130.1, 127.6, 124.6 (dd), 123.9 (m), 123.7, 123.3, 120.5, 116.1, 112.1, 111.5 (dd), 104.9 (dd), 61.3, 56.0, 52.8

Preparation 28

[2-Chloro-4-(4-fluoro-phenylamino)-phenyl]-(2-methyl-5-nitro-phenyl)-methanone (compound 428)

The reaction was carried out similarly as described in the preparation of compound 403, using compound 402 (22.6 mmol) and 4-fluoroaniline (24.8 mmol) except the time for the reaction was 16 h. The crude product was purified by flash chromatography using EtOAc/petroleum ether (40-60) 1:5 as the eluent to afford the title compound as yellow solid.

Preparation 29

(5-Amino-2-methyl-phenyl)-[2-chloro-4-(4-fluoro-phenylamino)-phenyl]-methanone (compound 429)

The reaction was carried out similarly as described in the preparation of compound 404, using compound 428 (19.2 mmol). The crude product was purified by flash chromatography using EtOAc/petroleum ether (40-60) 1:2 followed by 2:3 as the eluent to afford the title compound as solid.

Preparation 30

[2-Chloro-4-(4-fluoro-phenylamino)-phenyl]-(5-iodo-2-methyl-phenyl)-methanone (compound 430)

The reaction was carried out similarly as described in the preparation of compound 405, using compound 429 (8.46 mmol). The crude product was purified by flash chromatography using EtOAc/petroleum ether (40-60) 2:8 followed by 3:7 as the eluent to afford the title compound as solid.

Preparation 31

[2-Chloro-4-(4-fluoro-phenylamino)-phenyl]-(2-methyl-5-trimethylsilanylethynyl-phenyl)-methanone (compound 431)

The reaction was carried out similarly as described in the preparation of compound 406, using compound 430 (7.17 mmol) and ethynyltrimethylsilane (7.17 mmol). The crude product was purified by flash chromatography using EtOAc/petroleum ether (40-60) 1:8 as the eluent to afford the title compound as yellow solid.

Preparation 32

[2-Chloro-4-(4-fluoro-phenylamino)-phenyl]-(5-ethynyl-2-methyl-phenyl)-methanone (compound 432)

The reaction was carried out similarly as described in the preparation of compound 407, using compound 431 (5.95 mmol). The crude product was used without any further purification.

Example 21

[2-Chloro-4-(4-fluoro-phenylamino)-phenyl]-(2-methyl-5-{1-[2-(tetrahydro-pyran-2-yloxy)-ethyl]-1H-[1,2,3]triazol-4-yl}-phenyl)-methanone (compound 121)

The reaction was carried out similarly as described in the preparation of compound 101, using compound 432 (2.06 mmol) and compound 408 (2.06 mmol). The crude product was purified by continuous gradient flash chromatography using EtOAc/petroleum ether (40-60) 50:50 to 50:50 as the eluent to afford the title compound.
$^{13}$C NMR (CDCl$_3$) δ 196.1, 159.6 (d), 148.8, 147.0, 140.0, 137.5, 135.9 (d), 135.4, 134.0, 131.8, 128.4, 128.2, 127.8, 126.4, 124.2 (d), 120.8, 116.4 (d), 115.8, 112.3, 99.1, 65.8, 62.4, 50.6, 30.4, 25.2, 20.2, 19.4

Example 22

[2-Chloro-4-(4-fluoro-phenylamino)-phenyl]-{5-[1-(2-hydroxy-ethyl)-1H-[1,2,3]triazol-4-yl]-2-methyl-phenyl}-methanone (compound 122)

The reaction was carried out similarly as described in the preparation of compound 102, using compound 121 (1.63 mmol). The crude product was purified by continuous gradient flash chromatography using EtOAc/petroleum ether (40-60) 50:50 to 100:0 as the eluent to afford the title compound as yellow syrup.

$^{13}$C NMR (DMSO-d$_6$) δ 194.8, 158.1 (d), 149.1, 145.2, 139.9, 136.6 (d), 135.7, 134.0, 133.9, 131.6, 128.4, 127.0, 126.3, 124.8, 122.7 (d), 121.9, 116.1 (d), 114.9, 111.8, 59.7, 52.3, 19.4

Example 23

[2-Chloro-4-(4-fluoro-phenylamino)-phenyl]-{5-[1-(2,2-dimethyl-[1,3]dioxolan-4-ylmethyl)-1H-[1,2,3]triazol-4-yl]-2-methyl-phenyl}-methanone (compound 123)

The reaction was carried out similarly as described in the preparation of compound 101, using compound 432 (2.75 mmol) and compound 410 (2.75 mmol). The crude product was purified by continuous gradient flash chromatography using EtOAc/petroleum ether (40-60) 20:80 to 65:35 as the eluent to afford the title compound as foam.

$^{13}$C NMR (CDCl$_3$) δ 196.1, 159.7 (d), 148.9, 147.1, 140.1, 137.6, 135.9 (d), 135.5, 134.0, 131.8, 128.4, 128.0, 127.8, 126.4, 124.2 (d), 121.0, 116.4 (d), 115.8, 112.3, 110.3, 74.1, 66.5, 52.4, 26.7, 25.2, 20.2

Example 24

[2-Chloro-4-(4-fluoro-phenylamino)-phenyl]-{5-[1-(2,3-dihydroxy-propyl)-1H-[1,2,3]triazol-4-yl]-2-methyl-phenyl}-methanone (compound 124)

A solution of compound 123 (1.05 g, 2.02 mmol) in THF (10 mL) was added HCl (10 mL, aq., 10, 1N) and the mixture was stirred for 16 h at RT. The reaction mixture was poured into a mixture of EtOAc/water/NaHCO$_3$. The organic phase was washed with water, brine and then dried (MgSO$_4$), filtered and concentrated in vacuo to give the crude product. The crude product was purified by continuous gradient flash chromatography using MeOH/DCM 0:100 to 10:90 as the eluent to afford the title compound as white solid.

$^{13}$C NMR (DMSO-d$_6$) δ 194.8, 158.1 (d), 149.1, 145.1, 139.9, 136.6 (d), 135.7, 134.0, 133.9, 131.6, 128.4, 127.0, 126.3, 124.8, 122.7 (d), 122.3, 116.0 (d), 114.9, 111.8, 70.3, 63.2, 53.0, 19.4

Example 25

2-(4-{3-[2-Chloro-4-(4-fluoro-phenylamino)-benzoyl]-4-methyl-phenyl}-[1,2,3]triazol-1-yl)-acetamide (compound 125)

The reaction was carried out similarly as described in the preparation of compound 101, using compound 432 (1.04 mmol) and compound 411 (1.5 mmol). The crude product was purified by continuous gradient flash chromatography using EtOAc/DCM/petroleum ether (40-60) 0:80:20, 0:100:0 and 10:90:0 as the eluent to afford the title compound as yellow solid.

$^{13}$C NMR (DMSO-d$_6$) δ 194.8, 167.1, 158.0 (d), 149.1, 145.2, 139.9, 136.6 (d), 135.8, 134.0, 133.9, 131.6, 128.2, 127.0, 126.3, 124.9, 123.0, 122.7 (d), 116.0 (d), 114.8, 111.8, 51.5, 19.4

Example 26

[2-Chloro-4-(2,4-difluoro-phenylamino)-phenyl]-{5-[1-(2-chloro-ethyl)-1H-[1,2,3]triazol-4-yl]-2-methyl-phenyl}-methanone (compound 126)

To a flask containing a stirred mixture of triphenylphosphine (39 mg, 0.15 mmol) and 4,5-dichloro-3,6-dioxo-cyclohexa-1,4-diene-1,2-dicarbonitrile (44.5 mg, 0.20 mmol) in dry DCM (3.0 mL), was added tetra-N-butylammonium azide (56 mg, 0.20 mmol) at RT. Compound 102 (46 mg, 0.10 mmol) was then added and the reaction was stirred for 1 h. The reaction mixture was concentrated in vacuo and purified by continuous gradient flash chromatography using EtOAc/petroleum ether (40-60) 0:100 to 50:50 as the eluent to afford the title compound as foam.

$^{13}$C NMR (CDCl$_3$) δ 196.1, 159.2 (dd), 155.6 (dd), 148.0, 147.0, 139.9, 137.8, 135.3, 133.8, 131.9, 129.0, 127.9, 127.8, 126.4, 124.5 (dd), 124.3 (dd), 120.8, 116.3, 112.7, 111.6 (dd), 104.9 (dd), 51.8, 42.4, 20.2.

Preparation 33

(5-Azido-2-methyl-phenyl)-[2-chloro-4-(4-fluoro-phenylamino)-phenyl]-methanone (compound 433)

A mixture of NaN$_3$ (3.3 g), H$_2$O (8 mL) and DCM (2.8 mL) was cooled to 0° C. under stirring. Trifluoromethanesulfonic anhydride (1.34 mL, 8.46 mmol) was added slowly, keeping the temperature in the range −2 to 1° C. After 2 h the reaction mixture separated in a separation funnel. The aqueous phase was washed with EtOAc. The organic phases were washed with saturated NaHCO3 and concentrated in vacuo to give crude trifluoromethansulfonic azide that was used in the following.

To a suspension of compound 429 (1.00 g, 2.82 mmol) in DCM (5.0 mL) was added a solution of copper(II) sulphate pentahydrate (35.2 mg, 0.14 mmol) in H$_2$O (4.0 mL), and TEA (1.18 mL, 8.45 mmol). The crude trifluoromethansulfonic azide was added slowly under stirring to the reaction mixture followed by by MeOH (5 mL). After 18 h at RT the reaction mixture was poured into a mixture of EtOAc/NaHCO$_3$(aq.). The organic phase was washed with water, brine, filtered and concentrated in vacuo to give the crude product. The crude product was purified by continuous gradient flash chromatography using EtOAc/petroleum ether (40-60) 0:100 to 25:75 as the eluent to afford the title compound as yellow solid.

Example 27

[2-Chloro-4-(4-fluoro-phenylamino)-phenyl]-{5-[4-(2-hydroxy-ethyl)-[1,2,3]triazol-1-yl]-2-methyl-phenyl}-methanone (compound 127)

The reaction was carried out similarly as described in the preparation of compound 101, using compound 433 (1.10 mmol) and 3-butyne-1-ol (1.10 mmol). The crude product was purified by continuous gradient flash chromatography using EtOAc/petroleum ether (40-60) 50:50 to 100:0 as the eluent to afford the title compound as foam.

$^{13}$C NMR (CDCl$_3$) δ 194.8, 159.8 (d), 149.5, 146.3, 141.1, 138.1, 135.7 (d), 135.6, 134.8, 134.0, 132.5, 127.6, 124.5 (d), 122.2, 120.8, 119.9, 116.5 (d), 115.8, 112.4, 61.6, 28.8, 19.9

Preparation 34

(5-Azido-2-methyl-phenyl)-[2-chloro-4-(2,4-difluoro-phenylamino)-phenyl]-methanone (compound 434)

Compound 404 (5.40 g, 14.5 mmol) was dissolved in acetone (100 mL). Concentrated HCl (37%, 6.04 mL, 72 mmol) was added and the solution was cooled on an icebath. NaNO$_2$ (1.20 g, 17.4 mmol) was dissolved in H$_2$O (9 mL) and added to the above solution during 20 minutes. The internal temperature was kept at 0° C.-2° C. during the addition. The suspension was stirred on an ice bath for 1 h, after which a solution of NaN$_3$ (1.20 g, 17.4 mmol) in H$_2$O (12 mL) was added dropwise during 5 minutes. The mixture was stirred at 0° C. for 2 h. H$_2$O (50 mL) and EtOAc (100 mL) was added and stirred and the phases were separated. The organic phase was concentrated in vacuo to give the title compound. The crude product was used without any further purification. The crude product was purified by continuous gradient flash chromatography using EtOAc/petroleum ether (40-60) 0:100 to 50:50 as the eluent to afford the title compound as brown solid.

Example 28

[2-Chloro-4-(2,4-difluoro-phenylamino)-phenyl]-{5-[4-(2-hydroxy-ethyl)-[1,2,3]triazol-1-yl]-2-methyl-phenyl}-methanone (compound 128)

The reaction was carried out similarly as described in the preparation of compound 110, using compound 434 (6.87 mmol) and 3-butyne-1-ol (8.24 mmol). The crude product was purified by continuous gradient flash chromatography using EtOAc/petroleum ether (40-60) 50:50 to 100:0 as the eluent to afford the title compound as yellow foam.

$^{13}$C NMR (CDCl$_3$) δ 194.8, 159.4 (dd), 155.7 (dd), 148.4, 146.3, 140.8, 138.3, 135.5, 134.8, 133.8, 132.6, 128.4, 124.8 (dd), 124.1 (dd), 122.3, 120.9, 119.9, 116.2, 112.8, 111.7 (dd), 105.0 (dd), 61.6, 28.7, 20.0

Example 29

[2-Chloro-4-(2,4-difluoro-phenylamino)-phenyl]-{5-[4-(1-hydroxy-1-methyl-ethyl)-[1,2,3]triazol-1-yl]-2-methyl-phenyl}-methanone (compound 129)

The reaction was carried out similarly as described in the preparation of compound 116, using compound 434 (0.125 mmol) and 2-methyl-but-3-yn-2-ol (0.125 mmol). The crude product was purified by continuous gradient flash chromatography using EtOAc/petroleum ether (40-60) 30:70 to 70:30 as the eluent to afford the title compound.

$^{13}$C NMR (CDCl$_3$) δ 194.9, 159.4 (dd), 156.4, 155.8 (dd), 148.6, 140.8, 138.2, 135.5, 134.8, 133.8, 132.6, 128.2, 125.0 (dd), 124.1 (dd), 122.4, 120.9, 117.6, 116.1, 112.7, 111.7 (dd), 105.0 (dd), 68.7, 30.5, 19.9

Example 30

1-(1-{3-[2-Chloro-4-(2,4-difluoro-phenylamino)-benzoyl]-4-methyl-phenyl}-1H-[1,2,3]triazol-4-yl)-ethanone (compound 130)

The reaction was carried out similarly as described in the preparation of compound 116, using compound 434 (0.125 mmol) and but-3-yn-2-one (0.125 mmol). The crude product was purified by continuous gradient flash chromatography using EtOAc/petroleum ether (40-60) 0:100 to 50:50 as the eluent to afford the title compound.

$^{13}$C NMR (DMSO-d$_6$) δ 193.6, 191.2, 159.0 (dd), 155.8 (dd), 149.9, 147.6, 140.9, 137.3, 134.3, 134.2, 133.8, 132.5, 126.7 (dd), 125.6, 125.5, 124.0 (dd), 122.0, 119.8, 115.0, 112.0 (dd), 111.8, 105.1 (dd), 27.3, 19.1

Example 31

{5-[4-(1-Amino-1-methyl-ethyl)-[1,2,3]triazol-1-yl]-2-methyl-phenyl}-[2-chloro-4-(2,4-difluoro-phenylamino)-phenyl]-methanone (compound 131)

The reaction was carried out similarly as described in the preparation of compound 116, using compound 434 (0.125 mmol) and 1,1-dimethyl-prop-2-ynylamine (0.125 mmol). The crude product was purified by continuous gradient flash chromatography using MeOH/DCM 0:100 to 5:95 as the eluent to afford the title compound.

$^{13}$C NMR (CDCl$_3$) δ 194.9, 159.4 (dd), 155.8 (dd), 148.5, 140.8, 138.1, 135.4, 134.9, 133.8, 132.6, 128.3, 124.9 (dd), 124.1 (dd), 122.4, 120.8, 117.1, 116.1, 112.8, 111.7 (dd), 105.0 (dd), 31.2 (bs), 20.0

Example 32

1-{3-[2-Chloro-4-(2,4-difluoro-phenylamino)-benzoyl]-4-methyl-phenyl}-1H-[1,2,3]triazole-4-carboxylic acid methyl ester (compound 132)

The reaction was carried out similarly as described in the preparation of compound 116, using compound 434 (0.50 mmol) and propynoic acid methyl ester (0.50 mmol). The crude product was purified by continuous gradient flash chromatography using EtOAc/petroleum ether (40-60) 0:100 to 50:50 as the eluent to afford the title compound.

$^{13}$C NMR (CDCl$_3$) δ 194.4, 161.0, 159.5 (dd), 155.8 (dd), 148.6, 141.1, 140.6, 139.3, 135.5, 134.0, 133.9, 132.8, 128.1, 125.6, 124.9 (dd), 124.0 (dd), 122.6, 121.0, 116.1, 112.9, 111.7 (dd), 105.0 (dd), 52.4, 20.0

Example 33

1-{3-[2-Chloro-4-(2,4-difluoro-phenylamino)-benzoyl]-4-methyl-phenyl}-1H-[1,2,3]triazole-4-carboxylic acid (compound 133)

A suspension of compound 132 (100 mg, 0.21 mmol) in MeOH (5.0 mL) was added H$_2$O (0.6 mL) and LiOH (25 mg, 1.0 mmol) and the resulting reaction mixture was refluxed for 1 h. EtOAc was added to the reaction and pH adjuste to 1-2 with concentrated HCl (37%, 6 drops). The organic phase was separated and the aqueous layer was extracted with more EtOAc. The organic phases were collected and washed with water, brine, dried (MgSO$_4$), filtered and concentrated in vacuo to give the title compound as white solid.

$^{13}$C NMR (DMSO-d$_6$) δ 193.6, 161.3, 159.0 (dd), 155.7 (dd), 149.8, 140.8, 140.7, 137.1, 134.3, 134.1, 133.8, 132.4, 127.0, 126.7 (dd), 125.5, 124.0 (dd), 121.9, 119.7, 114.9, 112.0 (dd), 111.8, 105.0 (dd), 19.1

Example 34

[2-Chloro-4-(2,4-difluoro-phenylamino)-phenyl]-[5-(4-hydroxymethyl-[1,2,3]triazol-1-yl)-2-methyl-phenyl]-methanone (compound 134)

The reaction was carried out similarly as described in the preparation of compound 116, using compound 434 (0.125 mmol) and prop-2-yn-1-ol (0.125 mmol). The crude product was purified by continuous gradient flash chromatography using EtOAc/petroleum ether (40-60) 0:100 to 60:40 as the eluent to afford the title compound.

$^{13}$C NMR (CDCl$_3$) δ 194.8, 159.4 (dd), 155.8 (dd), 148.5, 148.4, 140.8, 138.5, 135.5, 134.7, 133.8, 132.7, 128.2, 124.8 (dd), 124.0 (dd), 121.0, 120.1, 116.1, 112.8, 111.8, 111.7 (dd), 105.0 (dd), 56.6, 20.0

Example 35

[2-Chloro-4-(2,4-difluoro-phenylamino)-phenyl]-{5-[4-(3-hydroxy-propenyl)-[1,2,3]triazol-1-yl]-2-methyl-phenyl}-methanone (compound 135)

The reaction was carried out similarly as described in the preparation of compound 116, using compound 434 (0.15 mmol) and pent-2-en-4-yn-1-ol (0.30 mmol). The crude product was purified by continuous gradient flash chromatography using EtOAc/petroleum ether (40-60) 30:70 to 50:50 as the eluent to afford the title compound as yellow solid.

$^{13}$C NMR (DMSO-d$_6$) δ 193.7, 158.9, 155.8, 149.8, 145.9, 140.8, 136.3, 134.3, 134.0, 133.2, 132.4, 126.6 (dd), 125.6, 124.0 (dd), 121.3, 119.3, 119.0, 116.8, 114.9, 112.0 (dd), 111.8, 105.0 (dd), 60.9, 19.1

Preparation 35

Toluene-4-sulfonic acid 2-(1-{3-[2-chloro-4-(2,4-difluoro-phenylamino)-benzoyl]-4-methyl-phenyl}-1H-[1,2,3]triazol-4-yl)-ethyl ester (compound 435)

A solution of compound 128 (250 mg, 0.53 mmol) in dry pyridine (2.0 mL) was flushed with argon and cooled to 0° C. 4-Methyl-benzenesulfonyl chloride (102 mg, 0.53 mmol) was added and the reaction was allowed to come to RT overnight under stirring. The reaction mixture was poured into a mixture of EtOAc/water. The organic phase was washed with water, brine, filtered and concentrated in vacuo to give the crude product. The crude product was purified by continuous gradient flash chromatography using EtOAc/petroleum ether (40-60) 25:75 to 50:50 as the eluent to afford the title compound.

Preparation 36

{5-[4-(2-Azido-ethyl)-[1,2,3]triazol-1-yl]-2-methyl-phenyl}-[2-chloro-4-(2,4-difluoro-phenylamino)-phenyl (compound 436)

A mixture of compound 435 (167 mg, 0.27 mmol), NaN$_3$ (26 mg, 0.40 mmol) and potassium iodide (4.4 mg, 0.027 mmol) in DMF (5 mL) was stirred at 50° C. for 18 h under argon. The reaction mixture was poured into a mixture of EtOAc/water. The organic phase was washed with brine, dried (MgSO$_4$), filtered and concentrated in vacuo to give the crude product. The crude product was purified by continuous gradient flash chromatography using EtOAc/petroleum ether (40-60) 0:100 to 50:50 as the eluent to afford the title compound as yellow oil.

Example 36

{5-[4-(2-Amino-ethyl)-[1,2,3]triazol-1-yl]-2-methyl-phenyl}-[2-chloro-4-(2,4-difluoro-phenylamino)-phenyl]-methanone (compound 136)

A solution of compound 436 (96 mg, 0.20 mmol) in THF (2.5 mL) was added 3 drops of water and triphenylphosphine (102 mg, 0.39 mmol) and then stirred for 18 h at RT. The reaction mixture was poured into a mixture of EtOAc/water. The organic phase was washed with water, brine, filtered and concentrated in vacuo to give the crude product. The crude product was purified by flash chromatography using MeOH as the eluent to afford the title compound.

$^{13}$C NMR (CDCl$_3$) δ 194.8, 159.4 (dd), 155.8 (dd), 148.4, 146.8, 140.8, 138.1, 135.5, 134.9, 133.8, 132.6, 128.4, 124.8 (dd), 124.1 (dd), 122.3, 120.8, 119.6, 116.2, 112.8, 111.7 (dd), 105.0 (dd), 41.6, 29.7, 20.0

Example 37

(1-{3-[2-Chloro-4-(2,4-difluoro-phenylamino)-benzoyl]-4-methyl-phenyl}-1H-[1,2,3]triazol-4-ylmethyl)-urea (compound 137)

The reaction was carried out similarly as described in the preparation of compound 116, using compound 434 (0.15 mmol) and prop-2-ynyl-urea (0.30 mmol). The crude product was purified by flash chromatography using EtOAc as the eluent to afford a solid. Trituration in MeOH gave the title compound as white solid.

$^{13}$C NMR (DMSO-d$_6$) δ 193.7, 158.9 (dd), 158.3, 155.8 (dd), 149.7, 147.2, 140.7, 136.3, 134.3, 134.2, 134.0, 132.4, 126.6 (dd), 125.6, 124.0 (dd), 121.4, 120.7, 119.2, 114.9, 112.0 (dd), 111.8, 105.0 (dd), 34.7, 19.1

Example 38

[2-Chloro-4-(2,4-difluoro-phenylamino)-phenyl]-{2-methyl-5-[4-(2-morpholin-4-yl-ethyl)-[1,2,3]triazol-1-yl]-phenyl}-methanone (compound 138)

Compound 435 (150 mg, 0.24 mmol), K$_2$CO$_3$ (50 mg, 0.36 mmol) and morpholine (0.5 mL) was placed in a vial (8 mL). DMF (0.5 mL) was added and the resulting reaction mixture was stirred at 50° C. for 18 h. The reaction mixture was added HCl (4 mL, 0.5N) and then extracted tvise with EtOAc (2 mL). The organic phases was concentrated on silica gel and purified by continuous gradient flash chromatography using MeOH/DCM 0:100 to 10:90 as the eluent to afford the title compound as white foam.

$^{13}$C NMR (CDCl$_3$) δ 194.8, 159.4 (dd), 155.8 (dd), 148.4, 146.7, 140.7, 138.1, 135.4, 134.9, 133.8, 132.6, 128.4, 124.8 (dd), 124.1 (dd), 122.3, 120.9, 119.6, 116.2, 112.8, 111.7 (dd), 105.0 (dd), 66.8, 57.9, 53.5, 23.0, 20.0

Example 39

[2-Chloro-4-(2,4-difluoro-phenylamino)-phenyl]-(2-methyl-5-{4-[2-(4-methyl-piperazin-1-yl)-ethyl]-[1,2,3]triazol-1-yl}-phenyl)-methanone (compound 139)

The reaction was carried out similarly as described in the preparation of compound 138, using compound 435 (0.24 mmol) and 1-methyl-piperazine (0.5 mL). The crude product was purified by continuous gradient flash chromatography using MeOH/DCM 0:100 to 15:85 as the eluent to afford the title compound as yellow foam.

$^{13}$C NMR (CDCl$_3$) δ 194.8, 148.4, 146.9, 140.8, 138.1, 135.5, 134.9, 133.8, 132.6, 128.4, 124.8 (dd), 124.1 (dd), 122.3, 120.9, 119.5, 116.2, 112.8, 111.7 (dd), 105.0 (dd), 57.5, 55.0, 52.7, 45.8, 23.4, 20.0

Example 40

[2-Chloro-4-(2,4-difluoro-phenylamino)-phenyl]-{5-[4-(2-diethylamino-ethyl)-[1,2,3]triazol-1-yl]-2-methyl-phenyl}-methanone (compound 140)

The reaction was carried out similarly as described in the preparation of compound 138, using compound 435 (0.24 mmol) and diethylamine (0.5 mL). The crude product was purified by continuous gradient flash chromatography using MeOH/DCM 0:100 to 15:85 as the eluent to afford the title compound as yellow foam.

$^{13}$C NMR (CDCl$_3$) δ 194.9, 159.4 (dd), 155.8 (dd), 148.5, 147.0, 140.8, 138.0, 135.4, 134.9, 133.8, 132.5, 128.3, 124.9 (dd), 124.1 (dd), 122.3, 120.8, 119.6, 116.2, 112.8, 111.7 (dd), 105.0 (dd), 52.2, 46.9, 23.4, 20.0, 11.5

Example 41

[2-Chloro-4-(2,4-difluoro-phenylamino)-phenyl]-(5-{4-[2-(2-hydroxy-ethylamino)-ethyl]-[1,2,3]triazol-1-yl}-2-methyl-phenyl)-methanone (compound 141)

The reaction was carried out similarly as described in the preparation of compound 138, using compound 435 (0.24 mmol) and 2-amino-ethanol (0.5 mL). The crude product was purified by continuous gradient flash chromatography using MeOH/DCM 0:100 to 15:85 as the eluent to afford the title compound as yellow foam.

$^{13}$C NMR (CDCl$_3$) δ 194.8, 148.6, 146.1, 140.8, 138.2, 135.4, 134.7, 133.9, 132.6, 128.2, 124.9 (dd), 124.1 (dd), 122.2, 120.8, 119.9, 116.1, 112.8, 111.8 (dd), 105.0 (dd), 60.0, 50.7, 48.1, 25.3, 19.9

Example 42

[2-Chloro-4-(2,4-difluoro-phenylamino)-phenyl]-{2-methyl-5-[4-(2-propylamino-ethyl)-[1,2,3]triazol-1-yl]-phenyl}-methanone (compound 142)

The reaction was carried out similarly as described in the preparation of compound 138, using compound 435 (0.24 mmol) and propylamine (0.5 mL). The crude product was purified by continuous gradient flash chromatography using MeOH/DCM 0:100 to 15:85 as the eluent to afford the title compound as yellow foam.

$^{13}$C NMR (CDCl$_3$) δ 194.8, 159.4 (dd), 155.8 (dd), 148.5, 146.3, 140.8, 138.2, 135.4, 134.8, 133.8, 132.6, 128.3, 124.8 (dd), 124.1 (dd), 122.3, 120.8, 119.8, 116.2, 112.8, 111.7 (dd), 105.0 (dd), 51.1, 48.3, 25.2, 22.2, 20.0, 11.6

Preparation 37

[2-Chloro-4-(4-fluoro-2-methyl-phenylamino)-phenyl]-(2-methyl-5-nitro-phenyl)-methanone (compound 437)

The reaction was carried out similarly as described in the preparation of compound 414, using compound 402 (0.56 mmol) and 4-fluoro-2-methyl-phenylamine (0.56 mmol). The crude product was purified by continuous gradient flash chromatography using EtOAc/petroleum ether (40-60) 0:100 to 25:75 as the eluent to afford the title compound as yellow foam.

Preparation 38

(5-Amino-2-methyl-phenyl)-[2-chloro-4-(4-fluoro-2-methyl-phenylamino)-phenyl]-methanone (compound 438)

The reaction was carried out similarly as described in the preparation of compound 415, using compound 437 (0.41 mmol). The crude product was used without any further purification.

Preparation 39

(5-Azido-2-methyl-phenyl)-[2-chloro-4-(4-fluoro-2-methyl-phenylamino)-phenyl]-methanone (compound 439)

The reaction was carried out similarly as described in the preparation of compound 416, using compound 438 (0.29 mmol). The crude product was used without any further purification.

Example 43

[2-Chloro-4-(4-fluoro-2-methyl-phenylamino)-phenyl]-{5-[4-(2-hydroxy-ethyl)-[1,2,3]triazol-1-yl]-2-methyl-phenyl}-methanone (compound 143)

The reaction was carried out similarly as described in the preparation of compound 116, using compound 439 (0.29 mmol) and but-3-yn-1-ol (0.40 mmol). The crude product was purified by continuous gradient flash chromatography using MeOH/DCM 0:100 to 5:95 as the eluent to afford the title compound.

$^{13}$C NMR (DMSO-d$_6$) δ 193.5, 159.5 (d), 151.2, 145.7, 141.1, 136.3 (d), 135.9, 134.6, 134.4, 134.2 (d), 132.3, 127.1 (d), 124.3, 121.0, 120.6, 118.8, 117.4 (d), 114.2, 113.5 (d), 111.1, 60.1, 29.1, 19.0, 17.6

Preparation 40

[2-Chloro-4-(2-methoxy-phenylamino)-phenyl]-(2-methyl-5-nitro-phenyl)-methanone (compound 440)

The reaction was carried out similarly as described in the preparation of compound 414, using compound 402 (0.56 mmol) and 2-methoxy-phenylamine (0.56 mmol). The crude product was purified by continuous gradient flash chromatography using EtOAc/petroleum ether (40-60) 0:100 to 25:75 as the eluent to afford the title compound as yellow foam.

Preparation 41

(5-Amino-2-methyl-phenyl)-[2-chloro-4-(2-methoxy-phenylamino)-phenyl]-methanone (compound 441)

The reaction was carried out similarly as described in the preparation of compound 415, using compound 440 (0.28 mmol). The crude product was used without any further purification.

Preparation 42

(5-Azido-2-methyl-phenyl)-[2-chloro-4-(2-methoxy-phenylamino)-phenyl]-methanone (compound 442)

The reaction was carried out similarly as described in the preparation of compound 416, using compound 441 (0.27 mmol). The crude product was used without any further purification.

Example 44

[2-Chloro-4-(2-methoxy-phenylamino)-phenyl]-{5-[4-(2-hydroxy-ethyl)-[1,2,3]triazol-1-yl]-2-methyl-phenyl}-methanone (compound 144)

The reaction was carried out similarly as described in the preparation of compound 116, using compound 442 (0.27 mmol) and but-3-yn-1-ol (0.30 mmol). The crude product was purified by continuous gradient flash chromatography using EtOAc/petroleum ether (40-60) 0:100 to 20:80 as the eluent to afford the title compound. $^{13}$C NMR (DMSO-$d_6$) δ 193.6, 152.4, 150.2, 145.6, 141.1, 135.9, 134.4, 134.2, 134.0, 132.3, 128.2, 125.3, 124.6, 123.4, 121.0, 120.6, 118.8, 115.1, 112.2, 111.7, 60.1, 55.4, 29.1, 19.0

Preparation 43

[2-Chloro-4-(4-chloro-2-methyl-phenylamino)-phenyl]-(2-methyl-5-nitro-phenyl)-methanone (compound 443)

The reaction was carried out similarly as described in the preparation of compound 414, using compound 402 (0.56 mmol) and 4-chloro-2-methyl-phenylamine (0.56 mmol). The crude product was purified by continuous gradient flash chromatography using EtOAc/petroleum ether (40-60) 0:100 to 25:75 as the eluent to afford the title compound as yellow foam.

Preparation 44

(5-Amino-2-methyl-phenyl)-[2-chloro-4-(4-chloro-2-methyl-phenylamino)-phenyl]-methanone (compound 444)

The reaction was carried out similarly as described in the preparation of compound 415, using compound 443 (0.24 mmol). The crude product was used without any further purification.

Preparation 45

(5-Azido-2-methyl-phenyl)-[2-chloro-4-(4-chloro-2-methyl-phenylamino)-phenyl]-methanone (compound 445)

The reaction was carried out similarly as described in the preparation of compound 416, using compound 444 (0.09 mmol). The crude product was used without any further purification.

Example 45

[2-Chloro-4-(4-chloro-2-methyl-phenylamino)-phenyl]-{5-[4-(2-hydroxy-ethyl)-[1,2,3]triazol-1-yl]-2-methyl-phenyl}-methanone (compound 145)

The reaction was carried out similarly as described in the preparation of compound 116, using compound 445 (0.03 mmol) and but-3-yn-1-ol (0.06 mmol). The crude product was purified by continuous gradient flash chromatography using EtOAc/petroleum ether (40-60) 30:70 to 100:0 as the eluent to afford the title compound. $^{13}$C NMR (CDCl$_3$) δ 194.7, 149.5, 146.2, 141.1, 138.2, 136.4, 135.7, 134.7, 134.1, 132.6, 131.2, 130.8, 127.4, 127.2, 125.6, 122.1, 120.7, 120.1, 115.8, 112.4, 61.5, 28.6, 19.9, 17.9

Preparation 46

[2-Chloro-4-(4-methoxy-phenylamino)-phenyl]-(2-methyl-5-nitro-phenyl)-methanone (compound 446)

The reaction was carried out similarly as described in the preparation of compound 414, using compound 402 (0.56 mmol) and 4-methoxy-phenylamine (0.56 mmol). The crude product was purified by continuous gradient flash chromatography using EtOAc/petroleum ether (40-60) 0:100 to 35:65 as the eluent to afford the title compound as yellow foam.

Preparation 47

(5-Amino-2-methyl-phenyl)-[2-chloro-4-(4-methoxy-phenylamino)-phenyl]-methanone (compound 447)

The reaction was carried out similarly as described in the preparation of compound 415, using compound 446 (0.31 mmol). The crude product was used without any further purification.

Preparation 48

(5-Azido-2-methyl-phenyl)-[2-chloro-4-(4-methoxy-phenylamino)-phenyl]-methanone (compound 448)

The reaction was carried out similarly as described in the preparation of compound 416, using compound 447 (0.08 mmol). The crude product was used without any further purification.

Example 46

[2-Chloro-4-(4-methoxy-phenylamino)-phenyl]-{5-[4-(2-hydroxy-ethyl)-[1,2,3]triazol-1-yl]-2-methyl-phenyl}-methanone (compound 146)

The reaction was carried out similarly as described in the preparation of compound 116, using compound 448 (0.03 mmol) and but-3-yn-1-ol (0.06 mmol). The crude product was purified by continuous gradient flash chromatography using EtOAc/petroleum ether (40-60) 30:70 to 100:0 as the eluent to afford the title compound. $^{13}$C NMR (CDCl$_3$) δ 194.7, 157.3, 150.5, 146.2, 141.4, 138.1, 135.8, 134.6, 134.2, 132.5, 132.2, 126.5, 125.3, 122.1, 120.6, 120.1, 115.2, 115.0, 111.8, 61.5, 55.6, 28.6, 19.9

Example 47

[2-Chloro-4-(2,4-difluoro-phenylamino)-phenyl]-{5-[4-(2-ethylamino-ethyl)-[1,2,3]triazol-1-yl]-2-methyl-phenyl}-methanone (compound 147)

The reaction was carried out similarly as described in the preparation of compound 138, using compound 435 (0.24 mmol) and ethylamine hydrochloride (0.55 mg). The crude product was purified by continuous gradient flash chromatography using MeOH/DCM 0:100 to 15:85 as the eluent to afford the title compound. $^{13}$C NMR (CDCl$_3$) δ 194.8, 159.4 (dd), 155.8 (dd), 148.6, 144.7, 140.8, 138.3, 135.4, 134.6, 133.9, 132.6, 128.2, 124.9 (dd), 124.1 (dd), 122.2, 120.8, 120.4, 116.1, 112.7, 111.7 (dd), 105.0 (dd), 46.5, 42.8, 23.2, 19.9, 12.1

Preparation 49

(4-Bromo-2-methyl-phenyl)-(2-methyl-5-nitro-phenyl)-methanone (compound 449)

The reaction was run under an argon atmosphere using dry glassware. 4-Bromo-2-methyliodobenzene (2.40 mL, 16.8 mmol) was dissolved in dry THF (15 mL) and cooled to −60° C. Isopropylmagnesium chloride (2 M in THF, 8.4 mL, 16.8 mmol) was added under stirring during 30 minutes. The reaction mixture was allowed to warm up to −40° C. and the mixture was stirred at −40° C. for 4 h. Compound 401 (4.62 g, 16.8 mmol) was added and the mixture was stirred at −40° C. for 3 h after which it was allowed to warm to room temperature and stirred for 17 h. A saturated aqueous solution of NH$_4$Cl (100 mL) was added and the mixture was stirred for 1 h. The phases were separated and the aqueous phase was extracted with EtOAc (2×100 mL). The combined organic phases were washed with brine, dried (MgSO$_4$), filtered and concentrated in vacuo. The crude product was purified by flash chromatography using CH$_2$Cl$_2$/petroleum ether (40-60) 1:6, 1:4, 1:2 as the eluent to afford the title compound as yellow compound.

Preparation 50

(5-Amino-2-methyl-phenyl)-(4-bromo-2-methyl-phenyl)-methanone (compound 450)

Compound 449 (1.85 g, 5.54 mmol) was dissolved in MeOH (75 mL). Zinc-dust (3.62 g, 55.4 mmol) and NH$_4$Cl (1.48 g, 27.7 mmol) were added. The reaction mixture was heated at reflux temperature for 2 h. The mixture was filtered through Decalite and washed with MeOH. The filtrate was concentrated on silica gel. The crude product was purified by continuous gradient flash chromatography using EtOAc/petroleum ether (40-60) 0:100 to 30:70 as the eluent to afford the title compound as yellow syrup.

Preparation 51

(5-Azido-2-methyl-phenyl)-(4-bromo-2-methyl-phenyl)-methanone (compound 451)

Compound 450 (1.91 g, 6.28 mmol) was dissolved in acetone (45 mL). Concentrated HCl (37%, 2.61 mL, 31 mmol) was added and the solution was cooled on an icebath. NaNO$_2$ (520 mg, 7.54 mmol) was dissolved in H$_2$O (4.5 mL) and added to the above solution during 20 minutes. The internal temperature was kept at 0° C.-2° C. during the addition. The suspension was stirred on an ice bath for 30 minutes, after which a solution of NaN$_3$ (618 mg, 9.42 mmol) in H$_2$O (13 mL) was added dropwise during 30 minutes. The mixture was stirred at 0° C. for 2 h. H$_2$O (50 mL) and EtOAc (2×75 mL) was added and stirred and the phases were separated. The organic phase was washed with brine and concentrated in vacuo to give the title compound. The crude product was used without any further purification.

Preparation 52

(4-Bromo-2-methyl-phenyl)-{5-[4-(2-hydroxy-ethyl)-[1,2,3]triazol-1-yl]-2-methyl-phenyl}-methanone (compound 452)

To a solution of compound 451 (170 mg, 0.51 mmol) in ethanol (2 mL) was added but-3-yn-1-ol (39 μL, 0.51 mmol). A freshly prepared solution of copper(II) sulphate pentahydrate (5.0 mg, 0.020 mmol) and sodium ascorbate (20 mg, 0.10 mmol) in water (0.5 mL) was added to the reaction mixture. The flask was closed and stirred for 24 h at RT under argon. The reaction mixture was poured into a mixture of EtOAc/water. The organic phase was washed with water, brine and then dried (MgSO$_4$), filtered and concentrated in vacuo to give the crude product. The crude product was purified by continuous gradient flash chromatography using EtOAc/petroleum ether (40-60) 40:60 to 95:5 as the eluent to afford the title compound as white syrup.

Example 48

[4-(2,4-Difluoro-phenylamino)-2-methyl-phenyl]-{5-[4-(2-hydroxy-ethyl)-[1,2,3]triazol-1-yl]-2-methyl-phenyl}-methanone (compound 148)

Compound 452 (78 mg, 0.19 mmol) was dissolved in dry 1,4-dioxan (1 mL) in a 8 mL screw cap vessel. 2,4-Difluoroaniline (20 μL, 0.19 mmol) was added and argon was blown over the mixture. Cs$_2$CO$_3$ (186 mg, 0.57 mmol), BINAP (5 mg, 0.008 mmol) and Pd(OAc)$_2$ (2 mg, 0.008 mmol) were added and argon was blown through the mixture and the screw cap vessel was closed. The mixture was stirred at 90° C. for 18 h. The reaction mixture was filtered through Decalite and the filtrate was concentrated in vacuo on silica gel. The crude product was purified by continuous gradient flash chromatography using EtOAc/petroleum ether (40-60) 40:60 to 100:0 as the eluent to afford the title compound as light yellow foam. $^{13}$C NMR (CDCl$_3$) δ 197.1, 158.9 (dd), 155.4 (dd), 147.6, 146.3, 143.3, 142.3, 137.1, 135.3, 134.7, 132.2, 128.2, 124.7 (dd), 124.0 (dd), 121.5, 120.0, 119.9, 118.0, 111.4 (dd), 111.2, 104.8 (dd), 61.6, 28.7, 22.2, 19.6

Example 49

[4-(3-Chloro-4-fluoro-phenylamino)-2-methyl-phenyl]-{5-[4-(2-hydroxy-ethyl)-[1,2,3]triazol-1-yl]-2-methyl-phenyl}-methanone (compound 149)

The reaction was carried out similarly as described in the preparation of compound 148, using compound 452 (0.13 mmol) and 3-chloro-4-fluoro-phenylamine (0.13 mmol). The crude product was purified by continuous gradient flash chromatography using MeOH/DCM/petroleum ether (40-60) 0:50:50, 0:100:0 and 5:95:0 as the eluent to afford the title compound as yellow solid. $^{13}$C NMR (DMSO-d$_6$) δ 196.4, 152.6 (d), 147.6, 145.8, 142.3, 142.3, 138.6 (d), 135.3 (d), 134.4, 132.2, 126.9, 121.1, 120.7, 120.5, 120.0 (d), 119.9 (d), 118.4, 117.7, 117.5 (d), 111.3, 60.2, 29.2, 22.0, 18.9

Example 50

{5-[4-(2-Hydroxy-ethyl)-[1,2,3]triazol-1-yl]-2-methyl-phenyl}-(2-methyl-4-phenylamino-phenyl)-methanone (compound 150)

The reaction was carried out similarly as described in the preparation of compound 148, using compound 452 (0.13 mmol) and aniline (0.13 mmol). The crude product was purified by continuous gradient flash chromatography using MeOH/DCM/petroleum ether (40-60) 0:50:50, 0:100:0 and 5:95:0 as the eluent to afford the title compound as yellow solid. $^{13}$C NMR (CDCl$_3$) δ 197.0, 147.9, 146.3, 143.4, 142.5, 140.4, 137.0, 135.5, 134.6, 132.2, 129.5, 127.6, 123.5, 121.4, 121.0, 119.9, 118.1, 111.4, 61.6, 28.7, 22.3, 19.5

Example 51

1-[3-(4-{5-[4-(2-Hydroxy-ethyl)-[1,2,3]triazol-1-yl]-2-methyl-benzoyl}-3-methyl-phenylamino)-phenyl]-ethanone (compound 151)

The reaction was carried out similarly as described in the preparation of compound 148, using compound 452 (0.13 mmol) and 1-(3-amino-phenyl)-ethanone (0.13 mmol). The crude product was purified by continuous gradient flash chromatography using MeOH/DCM/petroleum ether (40-60) 0:50:50, 0:100:0 and 5:95:0 as the eluent to afford the title compound as yellow solid. $^{13}$C NMR (CDCl$_3$) δ 197.8, 197.1, 147.1, 146.3, 143.3, 142.3, 141.2, 138.5, 137.1, 135.3, 134.7, 132.3, 129.8, 128.5, 124.8, 123.2, 121.5, 120.0, 119.9, 119.6, 118.7, 111.8, 61.6, 28.7, 26.7, 22.2, 19.6

Example 52

3-(4-{5-[4-(2-Hydroxy-ethyl)-[1,2,3]triazol-1-yl]-2-methyl-benzoyl}-3-methyl-phenylamino)-benzonitrile (compound 152)

The reaction was carried out similarly as described in the preparation of compound 148, using compound 452 (0.13 mmol) and 3-amino-benzonitrile (0.13 mmol). The crude product was purified by continuous gradient flash chromatography using MeOH/DCM/petroleum ether (40-60) 0:50:50, 0:100:0 and 5:95:0 as the eluent to afford the title compound as yellow solid. $^{13}$C NMR (DMSO-d$_6$) δ 196.5, 146.5, 145.7, 142.4, 142.1, 142.1, 135.4, 135.0, 134.5, 132.2, 130.7, 127.7, 124.9, 123.3, 121.1, 120.7, 120.6, 118.8, 118.6, 118.5, 112.2, 60.2, 29.2, 21.9, 18.9

Example 53

{5-[4-(2-Hydroxy-ethyl)-[1,2,3]triazol-1-yl]-2-methyl-phenyl}-[2-methyl-4-(3-trifluoromethyl-phenylamino)-phenyl]-methanone (compound 153)

The reaction was carried out similarly as described in the preparation of compound 148, using compound 452 (0.13 mmol) and 3-trifluoromethyl-phenylamine (0.13 mmol). The crude product was purified by continuous gradient flash chromatography using MeOH/DCM/petroleum ether (40-60) 0:50:50, 0:100:0 and 5:95:0 as the eluent to afford the title compound as yellow solid. $^{13}$C NMR (DMSO-d$_6$) δ 196.5, 146.8, 145.7, 142.3, 142.2, 142.1, 135.3, 135.1, 134.4, 132.2, 130.6, 130.2 (q), 127.6, 124.1 (q), 122.0, 120.7, 120.5, 118.5, 117.7 (q), 114.9 (q), 112.0, 60.2, 29.2, 21.9, 18.9

Example 54

[4-(3,4-Difluoro-phenylamino)-2-methyl-phenyl]-{5-[4-(2-hydroxy-ethyl)-[1,2,3]triazol-1-yl]-2-methyl-phenyl}-methanone (compound 154)

The reaction was carried out similarly as described in the preparation of compound 148, using compound 452 (0.13 mmol) and 3,4-difluoro-phenylamine (0.13 mmol). The crude product was purified by continuous gradient flash chromatography using MeOH/DCM/petroleum ether (40-60) 0:50:50, 0:100:0 and 5:95:0 as the eluent to afford the title compound as yellow solid. $^{13}$C NMR (DMSO-d$_6$) δ 196.4, 149.6 (dd), 147.5, 145.7, 144.7 (dd), 142.3, 142.2, 138.4 (dd), 135.3, 135.2, 134.4, 132.1, 127.0, 120.7, 120.5, 118.4, 117.9 (d), 117.7, 116.0 (dd), 111.4, 108.5 (d), 60.2, 29.2, 22.0, 18.9

Example 55

[4-(3,4-Dimethyl-phenylamino)-2-methyl-phenyl]-{5-[4-(2-hydroxy-ethyl)-[1,2,3]triazol-1-yl]-2-methyl-phenyl}-methanone (compound 155)

The reaction was carried out similarly as described in the preparation of compound 148, using compound 452 (0.13 mmol) and 3,4-dimethyl-phenylamine (0.13 mmol). The crude product was purified by continuous gradient flash chromatography using MeOH/DCM/petroleum ether (40-60) 0:50:50, 0:100:0 and 5:95:0 as the eluent to afford the title compound as yellow solid. $^{13}$C NMR (DMSO-d$_6$) δ 196.0, 148.9, 145.7, 142.7, 142.3, 138.4, 137.1, 135.5, 135.1, 134.4, 132.0, 130.5, 130.2, 125.4, 121.9, 120.7, 120.2, 118.2, 118.0, 117.0, 110.4, 60.2, 29.2, 22.2, 19.5, 18.8, 18.7

Example 56

[4-(3-Chloro-2-methyl-phenylamino)-2-methyl-phenyl]-{5-[4-(2-hydroxy-ethyl)-[1,2,3]triazol-1-yl]-2-methyl-phenyl}-methanone (compound 156)

The reaction was carried out similarly as described in the preparation of compound 148, using compound 452 (0.13 mmol) and 3-chloro-2-methyl-phenylamine (0.13 mmol). The crude product was purified by continuous gradient flash chromatography using MeOH/DCM/petroleum ether (40-60) 0:50:50, 0:100:0 and 5:95:0 as the eluent to afford the title compound as yellow solid. $^{13}$C NMR (CDCl$_3$) δ 197.0, 148.6, 146.3, 143.5, 142.5, 139.9, 137.0, 135.7, 135.5, 134.6, 132.2, 130.9, 127.5, 127.1, 126.0, 122.4, 121.3, 119.9, 119.9, 117.8, 111.1, 61.6, 28.7, 22.3, 19.5, 15.0

Example 57

[4-(3,4-Dichloro-phenylamino)-2-methyl-phenyl]-{5-[4-(2-hydroxy-ethyl)-[1,2,3]triazol-1-yl]-2-methyl-phenyl}-methanone (compound 157)

The reaction was carried out similarly as described in the preparation of compound 148, using compound 452 (0.13 mmol) and 3,4-dichloro-phenylamine (0.13 mmol). The crude product was purified by continuous gradient flash chromatography using MeOH/DCM/petroleum ether (40-60) 0:50:50, 0:100:0 and 5:95:0 as the eluent to afford the title compound as yellow solid. $^{13}$C NMR (DMSO-d$_6$) δ 196.4, 146.4, 145.6, 142.0, 141.9, 141.6, 135.3, 134.9, 134.3, 132.1, 131.5, 131.0, 127.6, 122.5, 120.6, 120.5, 119.7, 118.6, 118.4, 112.2, 60.1, 29.1, 21.8, 18.8

Example 58

N-[3-(4-{5-[4-(2-Hydroxy-ethyl)-[1,2,3]triazol-1-yl]-2-methyl-benzoyl}-3-methyl-phenylamino)-phenyl]-acetamide (compound 158)

The reaction was carried out similarly as described in the preparation of compound 148, using compound 452 (0.13 mmol) and N-(3-amino-phenyl)-acetamide (0.13 mmol). The crude product was purified by continuous gradient flash chromatography using NH$_3$(aq.)/MeOH/DCM 0:0:100, 1:9:90 as the eluent to afford the title compound as yellow solid. $^{13}$C NMR (DMSO-d$_6$) δ 196.1, 168.2, 147.9, 145.6, 142.4, 142.0, 141.2, 140.1, 135.1, 135.0, 134.3, 131.9, 129.3, 126.0, 120.6, 120.2, 118.2, 117.6, 114.2, 112.7, 111.1, 110.0, 60.1, 29.1, 24.0, 22.1, 18.7

Preparation 53

(4-Bromo-2-chloro-phenyl)-(2-chloro-5-nitro-phenyl)-methanone (compound 453)

The reaction was run under an argon atmosphere using dry glassware. 4-Bromo-2-chloro-iodobenzene (5.00 g, 15.8 mmol) was dissolved in dry THF (25 mL) and cooled to −35° C. Isopropylmagnesium chloride (2 M in THF, 8.27 mL, 16.5 mmol) was added under stirring during 90 minutes. A solution of ZnCl$_2$ (2.17 g, 15.9 mmol) in dry THF (35 mL) was slowly added to the reaction mixture at −35° C. The reaction mixture was allowed to come to RT after 1 h and a solution of 2-chloro-5-nitro-benzoyl chloride (3.64 g, 16.5 mmol) in THF (45 mL) was added followed by Cu(OAc)$_2$.H$_2$O (63 mg, 0.32 mmol). The resulting reaction mixture was stirred at RT for 18 h. The reaction mixture was poured into a mixture of EtOAc/water/HCl (1N). The organic phase was washed with water, brine and then dried (MgSO$_4$), filtered and concentrated in vacuo to give the crude product. The crude product was purified by flash chromatography using DCM/petroleum ether (40-60) 1:6; 1:4 and 1:2 as the eluent to afford the title compound as yellow solid.

Preparation 54

(5-Amino-2-chloro-phenyl)-(4-bromo-2-chloro-phenyl)-methanone (compound 454)

Compound 453 (2.17 g, 5.79 mmol) was suspended in MeOH (50 mL). SnCl$_2$.2H$_2$O (5.49 g, 28.9 mmol) was added. The reaction mixture was heated at reflux temperature for 1 h. The reaction mixture was poured into a mixture of EtOAc/water. The organic phase was washed with water, brine and then dried (MgSO$_4$), filtered and concentrated in vacuo to give the crude product. The crude product was purified by continuous gradient flash chromatography using DCM/petroleum ether (40-60) 50:50 to 100:0 as the eluent to afford the title compound as yellow solid.

Preparation 55

(5-Azido-2-chloro-phenyl)-(4-bromo-2-chloro-phenyl)-methanone (compound 455)

Compound 454 (1.21 g, 3.51 mmol) was dissolved in acetone (25 mL). Concentrated HCl (37%, 1.46 mL, 17.5 mmol) was added and the solution was cooled on an icebath. NaNO$_2$ (291 mg, 4.21 mmol) was dissolved in H$_2$O (2.5 mL) and added to the above solution during 20 minutes. The internal temperature was kept at 0° C.-2° C. during the addition. The suspension was stirred on an ice bath for 30 minutes, after which a solution of NaN$_3$ (348 mg, 5.31 mmol) in H$_2$O (7.5 mL) was added dropwise during 30 minutes. H$_2$O (50 mL) and EtOAc (2×75 mL) was added under stirrimg and the phases were separated. The organic phase was washed with brine and concentrated in vacuo to give the title compound. The crude product was used without any further purification.

Preparation 56

(4-Bromo-2-chloro-phenyl)-{2-chloro-5-[4-(2-hydroxy-ethyl)-[1,2,3]triazol-1-yl]-phenyl}-methanone (compound 456)

To a solution of compound 455 (1.32 g, 3.56 mmol) in ethanol (20 mL) was added but-3-yn-1-ol (0.3 mL, 3.91 mmol). A freshly prepared solution of copper(II) sulphate pentahydrate (36 mg, 0.14 mmol) and sodium ascorbate (141 mg, 0.71 mmol) in water (3.2 mL) was added to the reaction mixture. The flask was closed and stirred for 24 h at RT under argon. The reaction mixture was poured into a mixture of EtOAc/water. The organic phase was washed with water, brine and then dried (MgSO$_4$), filtered and concentrated in vacuo to give the crude product. The crude product was purified by continuous gradient flash chromatography using EtOAc/petroleum ether (40-60) 40:60 to 95:5 as the eluent to afford the title compound as white syrup.

Example 59

[2-Chloro-4-(2,4-difluoro-phenylamino)-phenyl]-{2-chloro-5-[4-(2-hydroxy-ethyl)-[1,2,3]triazol-1-yl]-phenyl}-methanone (compound 159)

The reaction was carried out similarly as described in the preparation of compound 148, using compound 456 (0.91 mmol) and 2,4-difluoro-phenylamine (0.91 mmol). The crude product was purified by continuous gradient flash chromatography using MeOH/DCM 0:100, 10:90 as the eluent to afford the title compound as yellow solid. $^{13}$C NMR (CDCl$_3$) δ 191.1, 159.6 (dd), 155.9 (dd), 149.1, 146.7, 141.1, 136.1, 135.7, 134.5, 131.7, 131.6, 126.9, 125.1 (dd), 123.8 (dd), 122.8, 121.0, 119.9, 116.1, 112.8, 111.7 (dd), 105.1 (dd), 61.5, 28.7

Preparation 57

[2-Chloro-4-(3-fluoro-phenylamino)-phenyl]-(2-methyl-5-nitro-phenyl)-methanone (compound 457)

The reaction was carried out similarly as described in the preparation of compound 414, using compound 402 (2.82 mmol) and 3-fluoro-phenylamine (2.82 mmol). The crude product was purified by continuous gradient flash chromatography using EtOAc/petroleum ether (40-60) 0:100 to 30:70 as the eluent to afford the title compound as yellow foam.

Preparation 58

(5-Amino-2-methyl-phenyl)-[2-chloro-4-(3-fluoro-phenylamino)-phenyl]-methanone (compound 458)

The reaction was carried out similarly as described in the preparation of compound 415, using compound 457 (2.25 mmol). The crude product was purified by flash chromatography using EtOAc/petroleum ether (40-60) 1:2 as the eluent to afford the title compound as yellow foam.

Preparation 59

(5-Azido-2-methyl-phenyl)-[2-chloro-4-(3-fluoro-phenylamino)-phenyl]-methanone (compound 459)

The reaction was carried out similarly as described in the preparation of compound 416, using compound 458 (1.83 mmol). The crude product was purified by flash chromatography using EtOAc/petroleum ether (40-60) 1:9 and 1:6 as the eluent to afford the title compound as yellow foam.

Example 60

[2-Chloro-4-(3-fluoro-phenylamino)-phenyl]-{5-[4-(2-hydroxy-ethyl)-[1,2,3]triazol-1-yl]-2-methyl-phenyl}-methanone (compound 160)

The reaction was carried out similarly as described in the preparation of compound 116, using compound 459 (0.26 mmol) and but-3-yn-1-ol (0.29 mmol). The crude product was purified by flash chromatography using EtOAc/petroleum ether (40-60) 6:1 as the eluent to afford the title compound as light yellow foam. $^{13}$C NMR (CDCl$_3$) δ 194.9, 163.6 (d), 147.6, 146.3, 141.8 (d), 140.7, 138.3, 135.4, 134.8, 133.8, 132.6, 130.9 (d), 128.7, 122.4, 120.9, 120.0, 117.1, 116.1 (d), 113.7, 110.5 (d), 107.6 (d), 61.6, 28.7, 20.0

Preparation 60

[2-Chloro-4-(3-chloro-phenylamino)-phenyl]-(2-methyl-5-nitro-phenyl)-methanone (compound 460)

The reaction was carried out similarly as described in the preparation of compound 414, using compound 402 (2.82 mmol) and 3-chloro-phenylamine (3.10 mmol). The crude product was purified by continuous gradient flash chromatography using EtOAc/petroleum ether (40-60) 0:100 to 30:70 as the eluent to afford the title compound as yellow foam.

Preparation 61

(5-Amino-2-methyl-phenyl)-[2-chloro-4-(3-chloro-phenylamino)-phenyl]-methanone (compound 461)

The reaction was carried out similarly as described in the preparation of compound 415, using compound 460 (2.13 mmol). The crude product was purified by flash chromatography using EtOAc/petroleum ether (40-60) 1:2 as the eluent to afford the title compound as yellow foam.

Preparation 62

(5-Azido-2-methyl-phenyl)-[2-chloro-4-(3-chloro-phenylamino)-phenyl]-methanone (compound 462)

The reaction was carried out similarly as described in the preparation of compound 416, using compound 461 (1.40 mmol). The crude product was purified by flash chromatography using EtOAc/petroleum ether (40-60) 1:6 as the eluent to afford the title compound as yellow syrup.

Example 61

[2-Chloro-4-(3-chloro-phenylamino)-phenyl]-{5-[4-(2-hydroxy-ethyl)-[1,2,3]triazol-1-yl]-2-methyl-phenyl}-methanone (compound 161)

The reaction was carried out similarly as described in the preparation of compound 116, using compound 462 (0.23 mmol) and but-3-yn-1-ol (0.28 mmol). The crude product was purified by flash chromatography using EtOAc/petroleum ether (40-60) 6:1 as the eluent to afford the title compound as light yellow foam. $^{13}$C NMR (CDCl$_3$) δ 194.9, 147.7, 146.3, 141.4, 140.7, 138.3, 135.4, 135.3, 134.8, 133.8, 132.6, 130.7, 128.7, 123.8, 122.4, 120.9, 120.7, 120.0, 118.8, 117.1, 113.6, 61.6, 28.7, 20.0

Preparation 63

(2-Chloro-4-m-tolylamino-phenyl)-(2-methyl-5-nitro-phenyl)-methanone (compound 463)

The reaction was carried out similarly as described in the preparation of compound 414, using compound 402 (2.82 mmol) and 3-methyl-phenylamine (3.10 mmol). The crude product was purified by continuous gradient flash chromatography using EtOAc/petroleum ether (40-60) 5:95 to 30:70 as the eluent to afford the title compound.

Preparation 64

(5-Amino-2-methyl-phenyl)-(2-chloro-4-m-tolylamino-phenyl)-methanone (compound 464)

The reaction was carried out similarly as described in the preparation of compound 415, using compound 463 (1.78 mmol). The crude product was purified by flash chromatography using EtOAc/petroleum ether (40-60) 1:2 as the eluent to afford the title compound as yellow syrup.

Preparation 65

(5-Azido-2-methyl-phenyl)-(2-chloro-4-m-tolylamino-phenyl)-methanone (compound 465)

The reaction was carried out similarly as described in the preparation of compound 416, using compound 464 (1.17 mmol). The crude product was purified by flash chromatography using EtOAc/petroleum ether (40-60) 1:9 and 1:6 as the eluent to afford the title compound as yellow syrup.

Example 62

(2-Chloro-4-m-tolylamino-phenyl)-{5-[4-(2-hydroxy-ethyl)-[1,2,3]triazol-1-yl]-2-methyl-phenyl}-methanone (compound 162)

The reaction was carried out similarly as described in the preparation of compound 116, using compound 465 (0.25 mmol) and but-3-yn-1-ol (0.30 mmol). The crude product was purified by flash chromatography using EtOAc/petroleum ether (40-60) 6:1 as the eluent to afford the title compound as light yellow foam. $^{13}$C NMR (CDCl$_3$) δ 194.8, 148.9, 146.3, 141.1, 139.7, 139.6, 138.1, 135.6, 134.8, 134.0, 132.5, 129.5, 127.5, 125.2, 122.3, 122.2, 120.7, 119.9, 118.7, 116.3, 112.8, 61.6, 28.7, 21.5, 19.9

Preparation 66

[2-Chloro-4-(3-methoxy-phenylamino)-phenyl]-(2-methyl-5-nitro-phenyl)-methanone (compound 466)

The reaction was carried out similarly as described in the preparation of compound 414, using compound 402 (2.82 mmol) and 3-methoxy-phenylamine (3.10 mmol). The crude product was purified by continuous gradient flash chromatography using EtOAc/petroleum ether (40-60) 0:100 to 30:70 as the eluent to afford the title compound.

Preparation 67

(5-Amino-2-methyl-phenyl)-[2-chloro-4-(3-methoxy-phenylamino)-phenyl]-methanone (compound 467)

The reaction was carried out similarly as described in the preparation of compound 415, using compound 466 (2.32 mmol). The crude product was purified by flash chromatography using EtOAc/petroleum ether (40-60) 1:2 as the eluent to afford the title compound as yellow foam.

Preparation 68

(5-Azido-2-methyl-phenyl)-[2-chloro-4-(3-methoxy-phenylamino)-phenyl]-methanone (compound 468)

The reaction was carried out similarly as described in the preparation of compound 416, using compound 467 (1.77 mmol). The crude product was purified by flash chromatography using EtOAc/petroleum ether (40-60) 1:9 and 1:6 as the eluent to afford the title compound.

Example 63

[2-Chloro-4-(3-methoxy-phenylamino)-phenyl]-{5-[4-(2-hydroxy-ethyl)-[1,2,3]triazol-1-yl]-2-methyl-phenyl}-methanone (compound 163)

The reaction was carried out similarly as described in the preparation of compound 116, using compound 468 (0.22 mmol) and but-3-yn-1-ol (0.28 mmol). The crude product was purified by flash chromatography using EtOAc/petroleum ether (40-60) 6:1 as the eluent to afford the title compound as light yellow foam. $^{13}$C NMR (CDCl$_3$) δ 194.8, 160.8, 148.5, 141.1, 141.0, 138.1, 135.5, 134.8, 133.9, 132.6, 130.4, 127.8, 122.2, 120.7, 119.9, 116.6, 113.6, 113.2, 109.4, 107.3, 61.6, 55.4, 28.7, 19.9

Preparation 69

(5-Amino-2-methyl-phenyl)-(4-bromo-2-chloro-phenyl)-methanone (compound 469)

Compound 402 (5.09 g, 14.4 mmol) was dissolved in MeOH (200 mL). Zinc-dust (9.38 g, 144 mmol) and NH$_4$Cl (3.84 g, 71.8 mmol) were added. The reaction mixture was heated at reflux temperature for 2 h. The mixture was filtered through Decalite and washed with MeOH. The filtrate was concentrated on silica gel. The crude product was purified by continuous gradient flash chromatography using EtOAc/petroleum ether (40-60) 0:100 to 20:80 as the eluent to afford the title compound as yellow syrup.

Preparation 70

(5-Azido-2-methyl-phenyl)-(4-bromo-2-chloro-phenyl)-methanone (compound 470)

Compound 469 (1.00 g, 3.08 mmol) was dissolved in acetone (23 mL). Concentrated HCl (37%, 1.30 mL, 15 mmol) was added and the solution was cooled on an icebath. NaNO$_2$ (255 mg, 3.70 mmol) was dissolved in H$_2$O (2.3 mL) and added to the above solution during 20 minutes. The internal temperature was kept at 0° C.-2° C. during the addition. The suspension was stirred on an ice bath for 30 minutes, after which a solution of NaN$_3$ (303 mg, 4.60 mmol) in H$_2$O (7 mL) was added dropwise during 30 minutes. The mixture was stirred at 0° C. for 1 h. H$_2$O (50 mL) and EtOAc (2×50 mL) was added and stirred and the phases were separated. The organic phase was washed with brine, dried (MgSO$_4$), filtered and concentrated in vacuo to give the title compound. The crude product was purified by flash chromatography using EtOAc/petroleum ether (40-60) 1:20 as the eluent to afford the title compound as yellow syrup.

Preparation 71

(4-Bromo-2-chloro-phenyl)-{5-[4-(2-hydroxy-ethyl)-[1,2,3]triazol-1-yl]-2-methyl-phenyl}-methanone (compound 471)

To a solution of compound 470 (1.04 g, 2.97 mmol) in ethanol (18 mL) was added but-3-yn-1-ol (225 μL, 2.97 mmol), copper(II) sulphate pentahydrate (30 mg, 0.12 mmol) and a solution of sodium ascorbate (119 mg, 0.6 mmol) in water (3.0 mL). The flask was closed and stirred for 24 h at RT under argon. After 18 h was added but-3-yn-1-ol (225 μL, 2.97 mmol), copper(II) sulphate pentahydrate (30 mg, 0.12 mmol) and a solution of sodium ascorbate (119 mg, 0.6 mmol) in water (3.0 mL). After 2 h the reaction mixture was poured into a mixture of EtOAc/water. The organic phase was washed with water, brine and then dried (MgSO$_4$), filtered and concentrated in vacuo to give the crude product. The crude product was purified by flash chromatography using EtOAc/petroleum ether (40-60) 3:1 as the eluent to afford the title compound as offwhite solid.

Example 64

[2-Chloro-4-(2,3-dichloro-phenylamino)-phenyl]-{5-[4-(2-hydroxy-ethyl)-[1,2,3]triazol-1-yl]-2-methyl-phenyl}-methanone (compound 164)

The reaction was carried out similarly as described in the preparation of compound 148, using compound 471 (0.13 mmol) and 2,3-dichloro-phenylamine (0.13 mmol). The crude product was purified by flash chromatography using MeOH/DCM 1:20 as the eluent to afford the title compound. $^{13}$C NMR (CDCl$_3$) δ 194.9, 146.4, 140.4, 139.1, 138.5, 135.1, 134.8, 134.0, 133.5, 132.7, 130.0, 127.6, 124.3, 123.2, 122.5, 121.0, 119.9, 118.6, 117.4, 115.2, 61.5, 28.7, 20.1

Example 65

[2-Chloro-4-(3,5-dimethyl-phenylamino)-phenyl]-{5-[4-(2-hydroxy-ethyl)-[1,2,3]triazol-1-yl]-2-methyl-phenyl}-methanone (compound 165)

The reaction was carried out similarly as described in the preparation of compound 148, using compound 471 (0.13 mmol) and 3,5-dimethyl-phenylamine (0.13 mmol). The crude product was purified by flash chromatography using MeOH/DCM 1:20 as the eluent to afford the title compound. $^{13}$C NMR (CDCl$_3$) δ 194.8, 149.2, 146.3, 141.2, 139.6, 139.4, 137.9, 135.6, 134.7, 134.1, 132.5, 126.9, 126.0, 122.1, 120.5, 120.0, 119.3, 116.3, 112.7, 67.1, 61.5, 28.8, 21.3, 19.8

Example 66

[2-Chloro-4-(2,5-difluoro-phenylamino)-phenyl]-{5-[4-(2-hydroxy-ethyl)-[1,2,3]triazol-1-yl]-2-methyl-phenyl}-methanone (compound 166)

The reaction was carried out similarly as described in the preparation of compound 148, using compound 471 (0.13 mmol) and 2,5-difluoro-phenylamine (0.13 mmol). The crude product was purified by flash chromatography using MeOH/DCM 1:20 as the eluent to afford the title compound. $^{13}$C NMR (CDCl$_3$) δ 194.9, 158.8 (d), 150.2 (d), 146.3 (d), 140.4, 138.4, 135.2, 134.8, 133.5, 132.7, 129.9, 122.5, 121.0, 119.9, 117.9, 116.6 (dd), 114.5, 109.5 (dd), 107.1 (d), 61.6, 28.7, 20.1

Example 67

[2-Chloro-4-(3,5-difluoro-phenylamino)-phenyl]-{5-[4-(2-hydroxy-ethyl)-[1,2,3]triazol-1-yl]-2-methyl-phenyl}-methanone (compound 167)

The reaction was carried out similarly as described in the preparation of compound 148, using compound 471 (0.13 mmol) and 3,5-difluoro-phenylamine (0.13 mmol). The crude product was purified by flash chromatography using MeOH/DCM 1:20 as the eluent to afford the title compound. $^{13}$C NMR (CDCl$_3$) δ 195.0, 163.8 (dd), 146.6, 146.4, 143.1 (t), 140.5, 138.4, 135.2, 134.8, 133.6, 132.7, 132.6, 132.3, 129.4, 122.5, 121.0, 120.1, 118.1, 114.5, 102.2 (m), 98.2 (t), 61.5, 28.8, 20.0

The invention claimed is:
1. A compound of general formula Ia or Ib

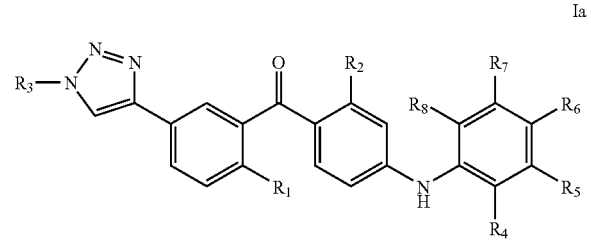

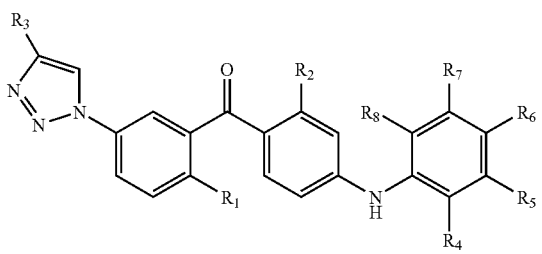

wherein
$R_1$ is methyl, chloro, bromo, or methoxy;
$R_2$ is chloro or methyl;
$R_3$ represents $C_{1-6}$alkyl, $C_{2-6}$alkenyl, $C_{2-6}$alkynyl, $C_{1-6}$hydroxyalkyl, $C_{1-6}$alkoxy, $C_{1-6}$alkoxycarbonyl, ureido, thioureido, $C_{1-6}$alkylcarbonyloxy, $C_{1-6}$alkoxycarbonyloxy, $C_{1-6}$alkoxysulfonyloxy, $C_{1-6}$alkoxycarbamoyl, or $C_{1-6}$aminocarbonyl,
each of which is optionally substituted with one or more, same or different substituents selected from the group consisting of halogen, hydroxy, mercapto, trifluoromethyl, cyano, carboxy, CONH$_2$, nitro, oxo, —S(O)$_2$NH$_2$, $C_{1-4}$alkyl, $C_{2-4}$alkenyl, $C_{2-4}$alkynyl, $C_{1-4}$hydroxyalkyl, $C_{1-4}$alkoxy, $C_{1-4}$alkoxycarbonyl, ureido, thioureido, $C_{1-4}$alkylcarbonyloxy, $C_{1-4}$alkoxycarbonyloxy, $C_{1-4}$alkoxysulfonyloxy, $C_{1-4}$alkoxycarbamoyl, $C_{1-4}$aminocarbonyl, $C_{1-4}$alkylthio, $C_{3-6}$cycloalkyl, $C_{3-6}$cycloalkenyl, amino, imino, $C_{1-4}$aminosulfonyl, $C_{1-4}$aminocarbonyloxy, $C_{1-4}$alkylsulfonylamino, $C_{1-4}$alkoxyimino, $C_{1-4}$alkylcarbonylamino, $C_{1-4}$alkylsulfonyl or 5- or 6-membered $C_{2-5}$heterocycloalkyl comprising 1-3 heteroatoms selected from O or N,
wherein said $C_{1-4}$alkyl, $C_{2-4}$alkenyl, $C_{2-4}$alkynyl, $C_{1-4}$hydroxyalkyl, $C_{1-4}$alkoxy, $C_{1-4}$alkoxycarbonyl, ureido, thioureido, $C_{1-4}$alkylcarbonyloxy, $C_{1-4}$alkoxycarbonyloxy, $C_{1-4}$alkoxysulfonyloxy, $C_{1-4}$alkoxycarbamoyl, $C_{1-4}$aminocarbonyl, $C_{1-4}$alkylthio, $C_{3-6}$cycloalkyl, $C_{3-6}$cycloalkenyl, amino, imino, $C_{1-4}$aminosulfonyl, $C_{1-4}$aminocarbonyloxy, $C_{1-4}$alkylsulfonylamino, $C_{1-4}$alkoxyimino, $C_{1-4}$alkylcarbonylamino, $C_{1-4}$alkylsulfonyl or 5- or 6-membered $C_{2-5}$heterocycloalkyl comprising 1-3 heteroatoms selected from O or N,
are optionally further substituted with one or more, same or different substituents selected from the group consisting of halogen, hydroxy, —NH$_2$, mercapto, trifluoromethyl, cyano, carboxy, CONH$_2$, nitro, oxo, —S(O)$_2$NH$_2$, $C_{1-4}$alkyl, or $C_{1-4}$hydroxyalkyl,
or $R_3$ represents hydrogen, or hydroxy,
$R_4$, $R_5$, $R_6$, $R_7$, and $R_8$ independently of each other represent hydrogen, halogen, —NH$_2$, hydroxy, trifluoromethyl, methoxy, ethoxy, methyl, or ethyl;
provided that the compound is not [4-(2-aminophenyl)amino)-2-chlorophenyl]-[2-methyl-541-[2-[(tetrahydro-2H-pyran-2-yl)oxy]ethyl]-1H-1,2,3-triazol-4-yl]-phenyl]-methanone or [4-[(2-aminophenyl)amino]-2-chlorophenyl]-[5-(2-hydroxyethyl)-1H-1,2,3-triazol-4-yl]-2-methylphenyl]-methanone;
or a pharmaceutically acceptable salt, or ester thereof.

2. A compound according to claim 1, wherein $R_3$ represents $C_{1-6}$alkyl, $C_{2-6}$alkenyl, $C_{2-6}$alkynyl, $C_{\_6}$hydroxyalkyl, $C_{1-6}$alkoxycarbonyl, or $C_{1-6}$aminocarbonyl, each of which are optionally substituted with one or more, same or different substituents selected from the group consisting of halogen, hydroxy, mercapto, trifluoromethyl, cyano, carboxy, CONH$_2$, nitro, oxo, —S(O)$_2$NH$_2$, $C_{1-4}$alkyl, $C_{2-4}$alkenyl, $C_{2-4}$alkynyl, $C_{1-4}$hydroxyalkyl, $C_{1-4}$alkoxy, $C_{1-4}$alkoxycarbonyl, ureido, thioureido, $C_{1-4}$alkylcarbonyloxy, $C_{1-4}$alkoxycarbonyloxy, $C_{1-4}$alkoxysulfonyloxy, $C_{1-4}$alkoxycarbamoyl, $C_{1-4}$aminocarbonyl, $C_{1-4}$alkylthio, $C_{3-6}$cycloalkyl, $C_{3-6}$cycloalkenyl, amino, imino, $C_{1-4}$aminosulfonyl, $C_{1-4}$aminocarbonyloxy, $C_{1-4}$alkylsulfonylamino, $C_{1-4}$alkoxyimino, $C_{1-4}$alkylcarbonylamino, $C_{1-4}$alkylsulfonyl, or 5- or 6-membered $C_{2-5}$heterocycloalkyl comprising 1-3 heteroatoms selected from O or N,
the last 25 of which are optionally further substituted with one or more, same or different substituents selected from the group consisting of halogen, hydroxy, —NH$_2$, mercapto, trifluoromethyl, cyano, carboxy, CONH$_2$, nitro, oxo, —S(O)$_2$NH$_2$, $C_{1-4}$alkyl, or $C_{1-4}$hydroxyalkyl, or $R_3$ represents hydrogen, or hydroxy.

3. A compound according to claim 1, wherein $R_4$, $R_5$, $R_6$, $R_7$, and $R_8$ independently of each other represent hydrogen, halogen, hydroxy, trifluoromethyl, methoxy, ethoxy, methyl, or ethyl.

4. A compound according to claim 1, wherein $R_4$, $R_5$, $R_6$, $R_7$, and $R_8$ independently of each other represent hydrogen or fluoro.

5. A compound according to claim 1, wherein at least three of $R_4$, $R_5$, $R_6$, $R_7$, or $R_8$ represent hydrogen.

6. A compound according to claim 1, wherein $R_5$, $R_7$, and $R_8$ represent hydrogen, or, wherein $R_4$, $R_5$, $R_7$, and $R_8$ represent hydrogen.

7. A compound according to claim 1, wherein $R_1$ is methyl and $R_2$ is chloro.

8. A compound according to claim 1, wherein $R_3$ represents $C_{1-4}$alkyl, or $C_{1-4}$hydroxyalkyl, each of which are optionally substituted with one or more, same or different substituents selected from the group consisting of hydroxy, mercapto, —NH$_2$, carboxy, CONH$_2$, nitro, oxo, —S(O)$_2$NH$_2$, $C_{1-2}$hydroxyalkyl, $C_{1-2}$alkoxy, $C_{1-2}$alkoxycarbonyl, $C_{1-2}$ureido, $C_{1-2}$thioureido, $C_{1-2}$alkylcarbonyloxy, $C_{1-2}$alkoxycarbonyloxy, $C_{1-2}$alkoxysulfonyloxy, $C_{1-2}$alkoxycarbamoyl, $C_{1-2}$aminocarbonyl, $C_{1-2}$alkylthio, $C_{1-2}$amino, $C_{1-2}$imino, $C_{1-2}$aminosulfonyl, $C_{1-2}$aminocarbonyloxy, $C_{1-2}$alkylsulfonylamino, $C_{1-2}$alkoxyimino, $C_{1-2}$alkylcarbonylamino, $C_{1-2}$alkylsulfonyl, or 5- or 6-membered $C_{2-5}$heterocycloalkyl comprising 1-3 heteroatoms selected from O or N, the last 20 of which are optionally further substituted with one or more, same or different substituents selected from the group consisting of hydroxy, —NH$_2$, carboxy, CONH$_2$, oxo, or $C_{1-3}$alkyl.

9. A compound according to claim 1, wherein $R_3$ represents $C_{1-3}$alkyl or $C_{1-3}$hydroxyalkyl, each of which are optionally substituted with one or more, same or different substituents selected from the group consisting of hydroxy, —NH$_2$, carboxy, CONH$_2$, oxo, —S(O)$_2$NH$_2$, $C_{1-2}$hydroxyalkyl, $C_{1-2}$alkoxy, $C_{1-2}$alkoxycarbonyl, $C_{0-2}$ureido, $C_{1-2}$aminocarbonyl, $C_{1-2}$amino, $C_{1-2}$alkylsulfonylamino, or 5- or 6-membered $C_{2-5}$heterocycloalkyl comprising 1-3 heteroatoms selected from O or N, the last 8 of which are optionally further substituted with one or more, same or different substituents selected from the group consisting of hydroxy or $C_{1-2}$alkyl.

10. A compound according to claim 1, wherein $R_3$ represents methyl, ethyl, propyl, all of which are substituted with one, two, three, or four, same or different substituents selected from the group consisting of hydroxy, CONH$_2$, oxo, methylsulfonylamino, —S(O)$_2$NH$_2$, tetrahydropyranyl, [1,3]-dioxolanyl the latter two optionally substituted with methyl or ethyl.

11. A compound according to claim 1, wherein $R_3$ is 2-hydroxyethyl, carbamoylmethyl, 2,3-dihydroxypropyl, 2-(methylsulfonylamino)ethyl, sulfonylaminopropyl, 2,2-dimethyl-[1,3]dioxolan-4-ylmethyl, 2-(tetrahydro-pyran-2-yloxy)-ethyl, 3-(tetrahydro-pyran-2-yloxy)-propyl.

12. A compound according to claim 1 of general formula Ia.

13. A compound according to claim 1 of general formula Ib.

14. A compound according to claim 1 selected from the group consisting of [2-Chloro-4-(2,4-difluoro-phenylamino)-phenyl]-(2-methyl-5-{1-[2-(tetrahydro-pyran-2-yloxy)-ethyl]-1H-[1,2,3]triazol-4-yl}-phenyl)-methanone (compound 101), [2-Chloro-4-(2,4-difluoro-phenylamino)-phenyl]-{5-[1-(2-hydroxy-ethyl)-1H-[1,2,3]triazol-4-yl]-2-methyl-phenyl}-methanone (compound 102), [2-Chloro-4-(2,4-difluoro-phenylamino)-phenyl]-(2-methyl-5-{1-[3-(tetrahydro-pyran-2-yloxy)-propyl]-1H-[1,2,3]triazol-4-yl}-phenyl)-methanone (compound 103), [2-Chloro-4-(2,4-difluoro-phenylamino)-phenyl]-{5-[1-(3-hydroxy-propyl)-1H-[1,2,3]triazol-4-yl]-2-methyl-phenyl}-methanone (compound 104), [2-Chloro-4-(2,4-difluoro-phenylamino)-phenyl]-{5-[1-(2,2-dimethyl-[1,3]dioxolan-4-ylmethyl)-1H-[1,2,3]-triazol-4-yl]-2-methyl-phenyl}-methanone (compound 105), [2-Chloro-4-(2,4-difluoro-phenylamino)-phenyl]-{5-[1-(2,3-dihydroxy-propyl)-1H-[1,2,3]triazol-4-yl]-2-methyl-phenyl}-methanone (compound 106), 2-(4-{3-[2-Chloro-4-(2,4-difluoro-phenylamino)-benzoyl]-4-methyl-phenyl}-[1,2,3]triazol-1-yl)-acetamide (compound 107), 3-(4-{3-[2-Chloro-4-(2,4-difluoro-phenylamino)-benzoyl]-4-methyl-phenyl}-[1,2,3]triazol-1-yl)-propane-1-sulfonic acid amide (compound 108), N-[2-(4-{3-[2-Chloro-4-(2,4-difluoro-phenylamino)-benzoyl]-4-methyl-phenyl}-[1,2,3]triazol-1-yl)-ethyl]-methanesulfonamide (compound 109), [2-Chloro-4-(4-fluoro-phenylamino)-phenyl]-(2-methyl-5-{1-[2-(tetrahydro-pyran-2-yloxy)-ethyl]-1H-[1,2,3]triazol-4-yl}-phenyl)-methanone (compound 121), [2-Chloro-4-(4-fluoro-phenylamino)-phenyl]-{5-[1-(2-hydroxy-ethyl)-1H-[1,2,3]triazol-4-yl]-2-methyl-phenyl}-methanone (compound 122), [2-Chloro-4-(4-fluoro-phenylamino)-phenyl]-{5-[1-(2,2-dimethyl-[1,3]dioxolan-4-ylmethyl)-1H-[1,2,3]-triazol-4-yl]-2-methyl-phenyl}-methanone (compound 123), [2-Chloro-4-(4-fluoro-phenylamino)-phenyl]-{5-[1-(2,3-dihydroxy-propyl)-1H-[1,2,3]triazol-4-yl]-2-methyl-phenyl]-methanone (compound 124), 2-(4-{3-[2-Chloro-4-(4-fluoro-phenylamino)-benzoyl]-4-methyl-phenyl}-[1,2,3]triazol-1-yl)-acetamide (compound 125), [2-Chloro-4-(4-fluoro-phenylamino)-phenyl]-{5-[4-(2-hydroxy-ethyl)-[1,2,3]triazol-1-yl]-2-methyl-phenyl}-methanone (compound 127), and [2-Chloro-4-(2,4-difluoro-phenylamino)-phenyl]-{5-[4-(2-hydroxy-ethyl)-[1,2,3]triazol-1-yl]-2-methyl-phenyl]-methanone (compound 128).

15. A pharmaceutical composition comprising a compound according to claim 1 or a pharmaceutically acceptable salt or ester thereof together with a pharmaceutically acceptable vehicle or excipient.

16. A composition according to claim 15 further comprising another active component selected from the group consisting of glucocorticoids, vitamin D analogues, anti-histamines, platelet activating factor (PAF) antagonists, anticolergenic agents, methyl xanthines, β-adregenic agents, COX-2 inhibitors, salicylates, indomethacin, flufenamate, naproxen, timegadine, gold salts, peniciliamine, serum cholesterol reducing agents, retinoids, zinc salts and salicylazosulfapyridin.

17. A pharmaceutical composition comprising a compound according to claim 14 or a pharmaceutically acceptable salt or ester thereof together with a pharmaceutically acceptable vehicle or excipient.

18. A compound according to claim 1 selected from the group consisting of [2-Chloro-4-(2,4-difluoro-phenylamino)-phenyl]-{5-[4-(2-hydroxy-ethyl)-[1,2,3]triazol-1-yl]-2-methyl-phenyl}-methanone (compound 128), and {5-[4-(1-Amino-1-methyl-ethyl)-[1,2,3]triazol-1-yl]-2-methyl-phenyl}-[2-chloro-4-(2,4-difluoro-phenylamino)-phenyl]-methanone (compound 131).

\* \* \* \* \*